US012648765B2

(12) United States Patent
Tsubota et al.

(10) Patent No.: US 12,648,765 B2
(45) Date of Patent: Jun. 9, 2026

(54) ENDOSCOPE PUNCTURE NEEDLE

(71) Applicant: OLYMPUS CORPORATION, Hachioji (JP)

(72) Inventors: Miho Tsubota, Tokyo (JP); Hirofumi Eto, Akiruno-shi (JP); Shuntaro Hattori, Hirosaki (JP); Hiroyuki Morishita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1208 days.

(21) Appl. No.: 17/526,650

(22) Filed: Nov. 15, 2021

(65) Prior Publication Data

US 2022/0071609 A1     Mar. 10, 2022

Related U.S. Application Data

(63) Continuation-in-part of application No. PCT/JP2020/019451, filed on May 15, 2020.

(30) Foreign Application Priority Data

May 17, 2019   (WO) ................. PCT/JP2019/019665

(51) Int. Cl.
    *A61B 10/04*        (2006.01)
    *A61B 10/02*        (2006.01)
(52) U.S. Cl.
    CPC .......... *A61B 10/04* (2013.01); *A61B 10/0266* (2013.01); *A61B 2010/045* (2013.01)
(58) Field of Classification Search
    CPC ................ A61B 10/04; A61B 10/0266; A61B 2010/045

(Continued)

(56) References Cited

U.S. PATENT DOCUMENTS 9,198,686 B2 * 12/2015 Motai .............. A61B 17/32053
2015/0250493 A1 * 9/2015 Umar .............. A61B 17/32053
                                              606/133

(Continued)

FOREIGN PATENT DOCUMENTS

CN        102791208 A      11/2012
CN        109069737 A      12/2018

(Continued)

OTHER PUBLICATIONS

Jun. 28, 2024 Office Action issued in Chinese Patent Application No. 202080034272.7.

(Continued)

*Primary Examiner* — Alex M Valvis
*Assistant Examiner* — Chanel J Jhin
(74) *Attorney, Agent, or Firm* — Oliff PLC

(57)                    ABSTRACT

An endoscope puncture needle including a tubular portion that includes first and second needle tip portions at a distal end thereof. The first needle tip portion includes a first needle tip at a distal end, and first and second blade surfaces extending towards the first needle tip. The second needle tip portion includes a second needle tip at a distal end, and third and fourth blade surfaces extending towards the second needle tip. The first blade surface and the third blade surface face in directions approaching each other, and the second blade surface and the fourth blade surface face in directions approaching each other.

21 Claims, 35 Drawing Sheets

(58) Field of Classification Search
    USPC ........................................................ 600/564
    See application file for complete search history.

(56)                    References Cited

U.S. PATENT DOCUMENTS

| | | | |
|---|---|---|---|
| 2016/0030017 | A1 | 2/2016 | Mcweeney et al. |
| 2018/0317895 | A1 | 11/2018 | Kadamus et al. |

FOREIGN PATENT DOCUMENTS

| | | | |
|---|---|---|---|
| CN | 109549690 | A | 4/2019 |
| EP | 2 520 237 | A1 | 11/2012 |
| JP | 2005-073798 | A | 3/2005 |
| JP | 2016-032630 | A | 3/2016 |
| JP | 2017-510329 | A | 4/2017 |
| WO | 2012/014773 | A1 | 2/2012 |
| WO | 2015/126926 | A1 | 8/2015 |

OTHER PUBLICATIONS

Jan. 30, 2024 Notice of Allowance issued in Japanese Patent Application No. 2023-110243.
Jul. 21, 2020 Search Report issued in International Patent Application No. PCT/JP2020/019451.
Dec. 9, 2024 Office Action issued in Chinese Patent Application No. 202080034272.7.

* cited by examiner

ENDOSCOPE PUNCTURE NEEDLE

This application is a continuation-in-part application of PCT International Application No. PCT/JP2020/019451, filed on May 15, 2020, which in turn claims priority to PCT International Application No. PCT/JP2019/019665, filed on May 17, 2019. The entire contents of both PCT International Applications are incorporated herein by reference.

TECHNICAL FIELD

The present disclosure relates to an endoscope puncture needle.

BACKGROUND

A test method called a biopsy, which includes collecting a small amount of body tissue and observing the body tissue with a microscope, is known. In a case where body tissue of a deep portion of an organ or the like is to be collected, it is difficult to make an observation using an optical endoscope. For this reason, endoscopic ultrasound guided fine needle aspiration (EUS-FNA), which acquires the ultrasound tomogram of the organ using an ultrasound endoscope or the like and inserts a puncture needle including a tubular needle tube into the organ under an ultrasound observation to collect tissue, is used. A puncture needle, which collects a large amount of body tissue, is required in the endoscopic ultrasound guided fine needle aspiration.

For example, an endoscopic puncture needle device that can take in tissue as a mass and cut out the tissue from peripheral tissue is known. A puncture needle including two sharp distal end portions can efficiently cut into body tissue.

But the puncture needle does not have a sufficient effect in terms of the collectability of collecting the cut-out body tissue into the puncture needle.

SUMMARY

According to an aspect of the present disclosure, an endoscope puncture needle includes a tubular portion that includes first and second needle tip portions at a distal end thereof. The first needle tip portion includes a first needle tip at a distal end, and first and second blade surfaces extending towards the first needle tip. The second needle tip portion includes a second needle tip at a distal end, and third and fourth blade surfaces extending towards the second needle tip. The first blade surface and the third blade surface face in directions approaching each other, and the second blade surface and the fourth blade surface face in directions approaching each other.

BRIEF DESCRIPTION OF DRAWINGS

FIG. 32 is a cross-sectional view taken along a central axis and seen in the same direction as FIG. 31.

FIG. 33 is a cross-sectional view taken along line A-A of the needle tube shown in FIG. 27.

FIG. 34 is a cross-sectional view taken along line B-B of the needle tube shown in FIG. 27.

DESCRIPTION OF EMBODIMENTS

Figure 1:
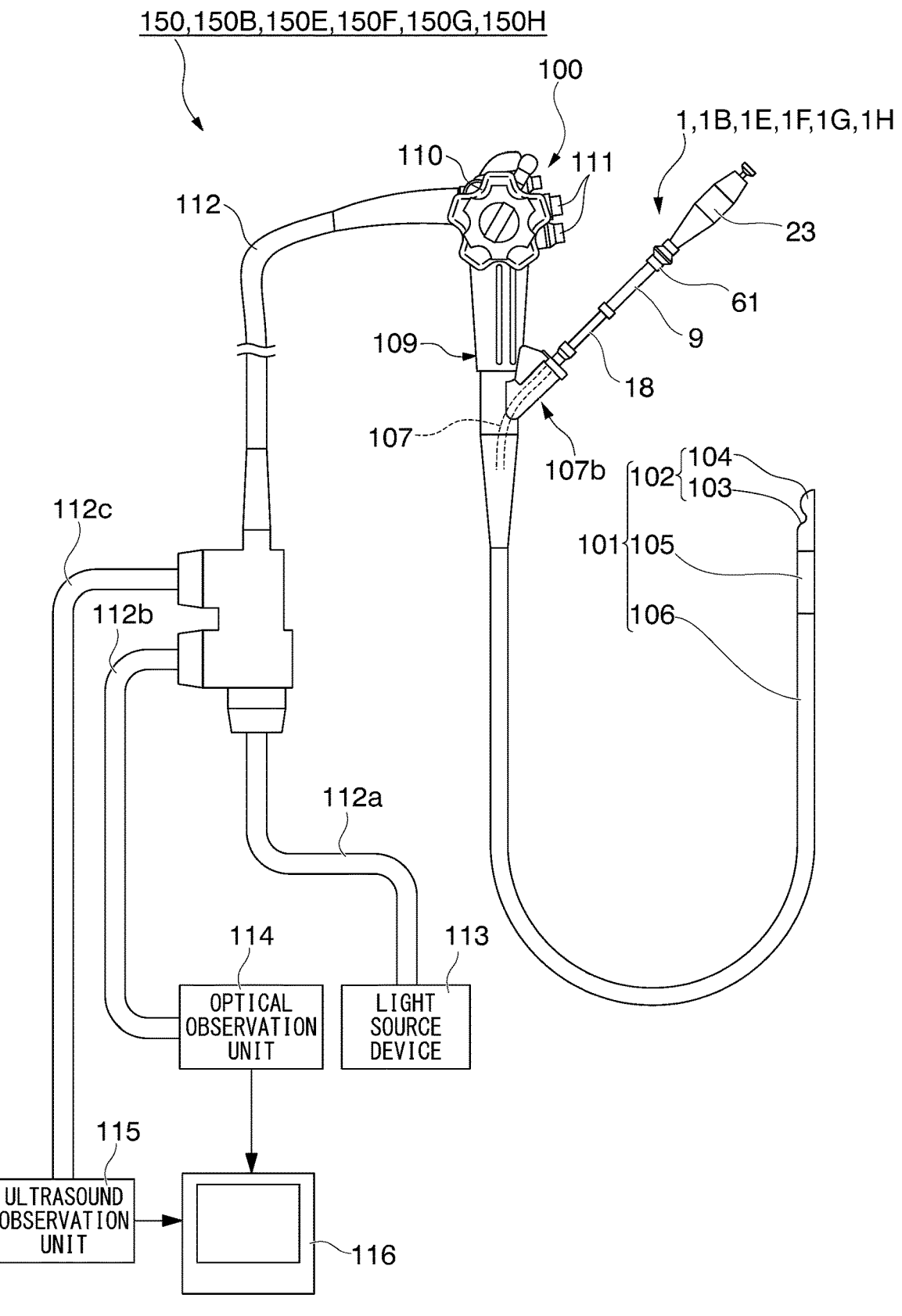
FIG. 1 is a diagram showing the entire biopsy system including an endoscope puncture needle according to an exemplary embodiment.

A biopsy system 150 including an endoscope puncture needle 1 according to an exemplary embodiment of the present disclosure will be described with reference to FIGS. 1 to 10. FIG. 1 is a diagram showing the entire biopsy system 150 including the endoscope puncture needle 1 according to this embodiment.

[Biopsy System 150]

As shown in FIG. 1, the biopsy system 150 is medical equipment that is used to collect body tissue required for a biopsy. The biopsy system 150 includes an ultrasound endoscope 100 and an endoscope puncture needle 1 (hereinafter, simply referred to as a "puncture needle 1".).

[Ultrasound Endoscope 100]

As shown in FIG. 1, the ultrasound endoscope 100 includes an insertion unit 101 that is to be inserted into a body from a distal end thereof, an operation unit 109 that is mounted on the proximal end of the insertion unit 101, a universal cord 112 of which one end is connected to the side portion of the operation unit 109, a light source device 113 that is connected to the other end of the universal cord 112 through a branch cable 112a, an optical observation unit 114 that is connected to the other end of the universal cord 112 through a branch cable 112b, and an ultrasound observation unit 115 that is connected to the other end of the universal cord 112 through a branch cable 112c.

The insertion unit 101 includes a hard distal end part 102, an active bendable part 105, and a flexible tube part 106 that are arranged in this order from the distal end side thereof.

The hard distal end part 102 is provided with an optical image pickup mechanism 103 that is used to make an optical observation and an ultrasound scanning mechanism 104 that is used to make an ultrasound observation.

The optical image pickup mechanism 103 includes an image pickup optical system of which the field of view is directed obliquely to the front side of the hard distal end part 102, an image sensor, such as a CCD or a CMOS, that detects the image of a subject incident through the image pickup optical system, a CPU that controls the operation of the image sensor, and the like.

The ultrasound scanning mechanism 104 includes an ultrasound oscillator (not shown) that emits and receives ultrasound. The ultrasound scanning mechanism 104 receives reflected waves, which are ultrasound emitted from the ultrasound oscillator and reflected by an object to be observed, by the ultrasound oscillator and outputs signals, which are based on the ultrasound received by the ultrasound oscillator, to the ultrasound observation unit 115.

The active bendable part 105 is a tubular member that is formed of a plurality of tubular joints arranged and connected to each other in the direction of the center line of the insertion unit 101. The active bendable part 105 is an active bendable part that is bent in a predetermined direction in a case where an angle wire (not shown) fixed to the distal end of the active bendable part 105 and extending up to the operation unit 109 is operated to be pulled by the operation unit 109. The active bendable part 105 of this embodiment can be bent in two directions along the scanning direction of ultrasound.

The flexible tube part 106 is a tubular member that is softly formed so as to be capable of guiding the hard distal end part 102 to a desired position in lumen tissue or a body cavity. A channel 107 and a pipe line (not shown), which is used for air/water supply, suction, and the like, are provided in each of the active bendable part 105 and the flexible tube part 106.

As shown in FIG. 1, the channel 107 is a tubular portion into which the puncture needle 1 can be inserted. The distal end of the channel 107 is opened at the distal end of the hard distal end part 102, and the proximal end of the channel 107 is opened on the side surface of the distal end portion of the operation unit 109.

As shown in FIG. 1, the operation unit 109 has an outer surface that is formed so as to be capable of being held by the hand of an operator using the ultrasound endoscope 100. The operation unit 109 includes a bending operation mechanism 110 that is used to pull the angle wire to bend the active bendable part 105 or to pull an elevating wire to operate an elevator 108, and a plurality of switches 111 that are used for air supply, water supply, or suction through the pipe line.

The light source device 113 is a device that emits illumination light used to pick up an image by the optical image pickup mechanism 103.

The optical observation unit 114 is adapted to display a video, which is picked up by the image sensor of the optical image pickup mechanism 103, on a monitor 116.

The ultrasound observation unit 115 is adapted to receive signals output from the ultrasound scanning mechanism 104, to generate an image on the basis of the signals, and to display the image on the monitor 116.

[Puncture Needle 1]

Figure 2:
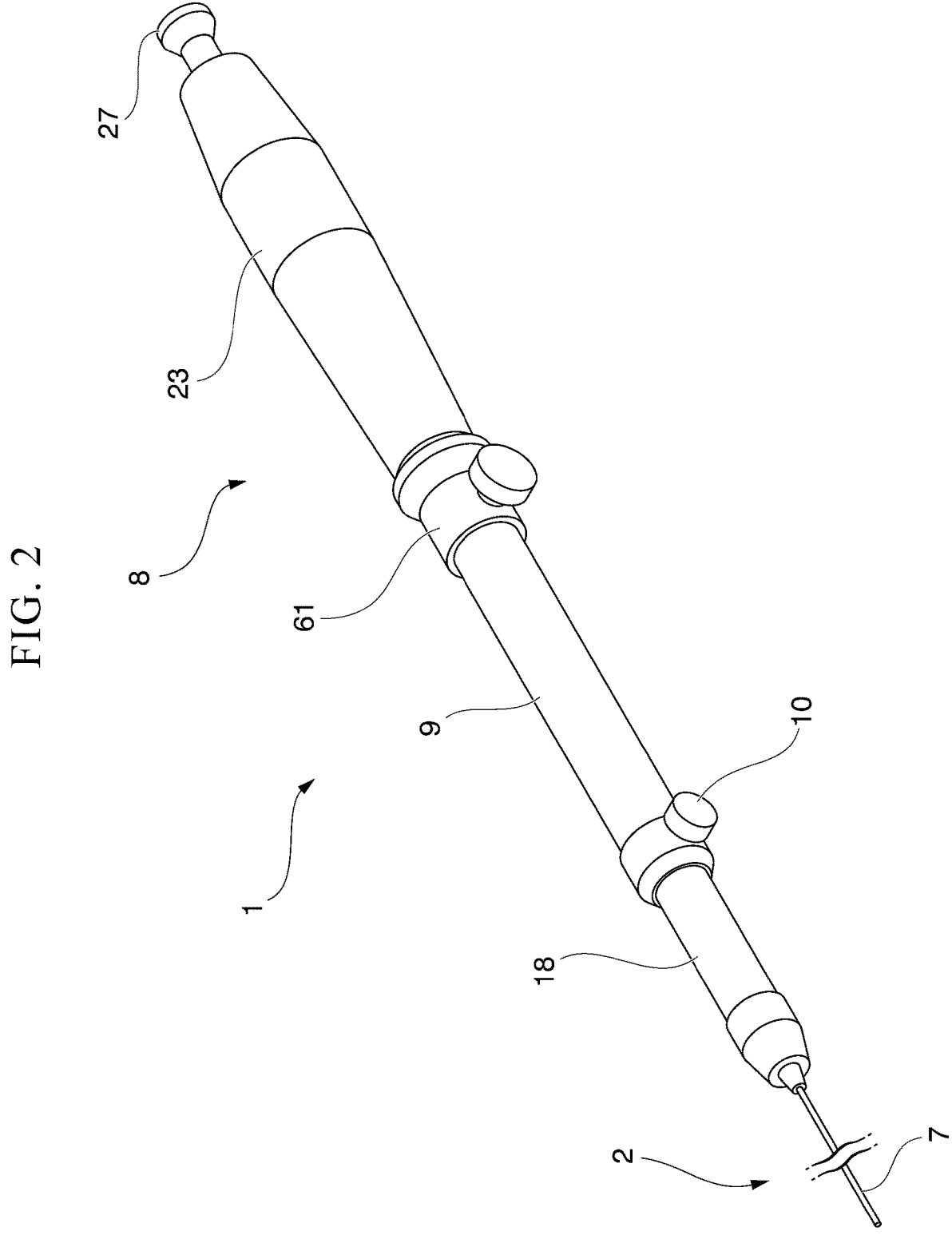
FIG. 2 is a perspective view of the endoscope puncture needle.
Figure 3:
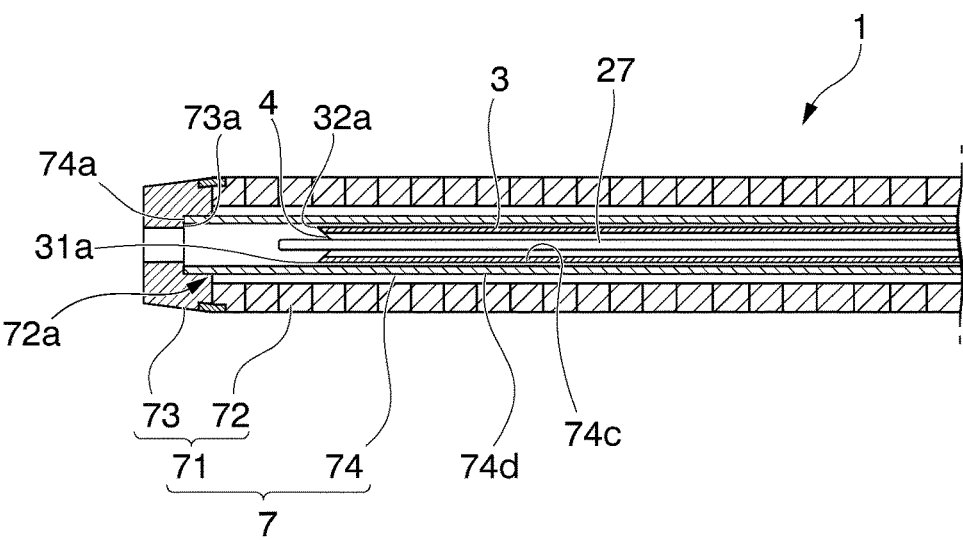
FIG. 3 is a longitudinal sectional view showing the cross section of a distal end portion of the endoscope puncture needle taken along the longitudinal axis of the endoscope puncture needle.

FIG. 2 is a perspective view of the puncture needle 1. FIG. 3 is a longitudinal sectional view showing the cross section of the distal end portion of the puncture needle 1 taken along the longitudinal axis of the puncture needle 1.

As shown in FIG. 2, the puncture needle 1 includes an insertion body 2, an operation unit 8, and a stylet 27.

[Insertion Body 2]

The insertion body 2 is an elongated member that can be inserted into the channel 107 of the ultrasound endoscope 100. As shown in FIGS. 2 and 3, the insertion body 2 includes a needle tube 3 and a sheath 7.

Figure 4:
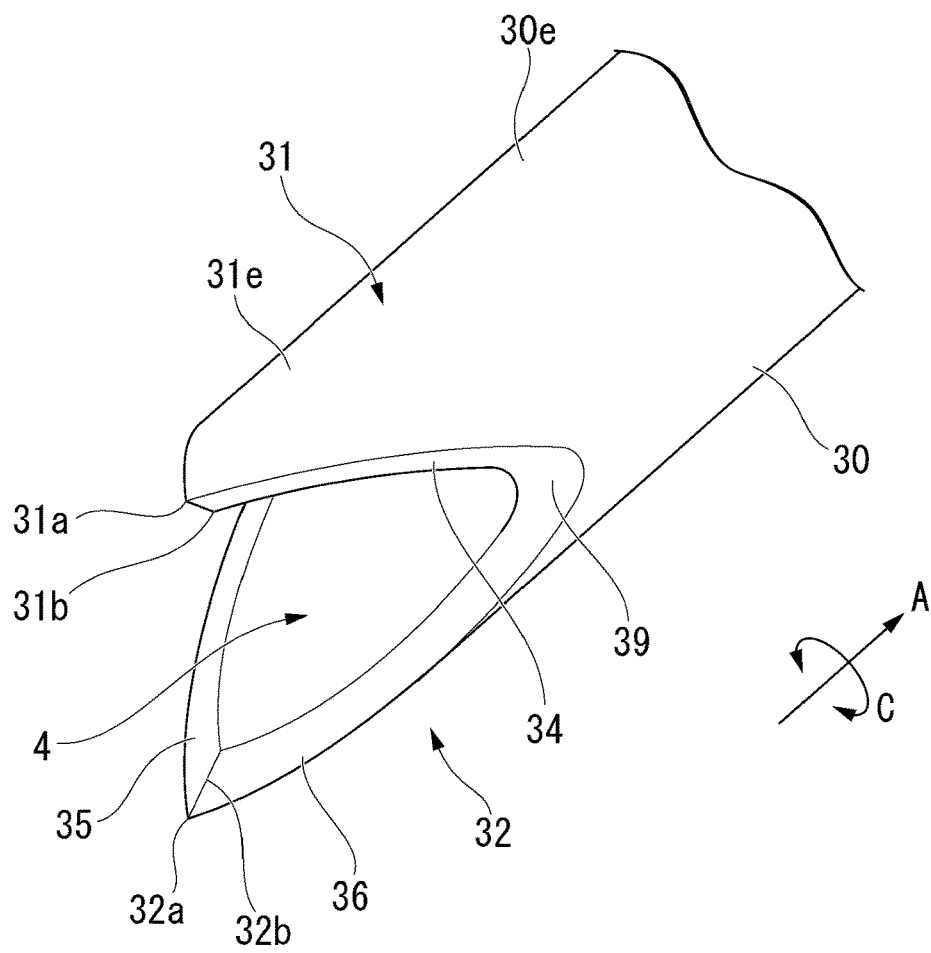
FIG. 4 is a perspective view of a needle tube included in the endoscope puncture needle.
Figure 5:
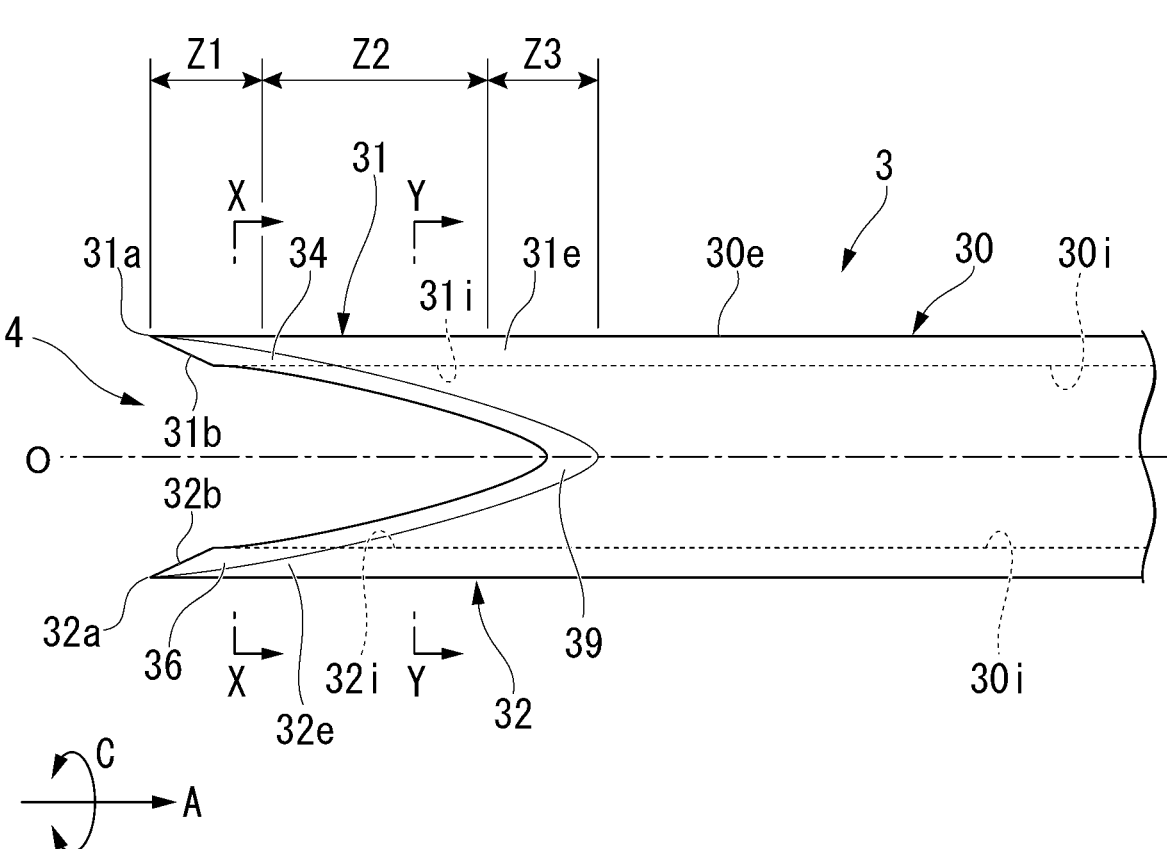
FIG. 5 is a side view of the needle tube.
Figure 6:
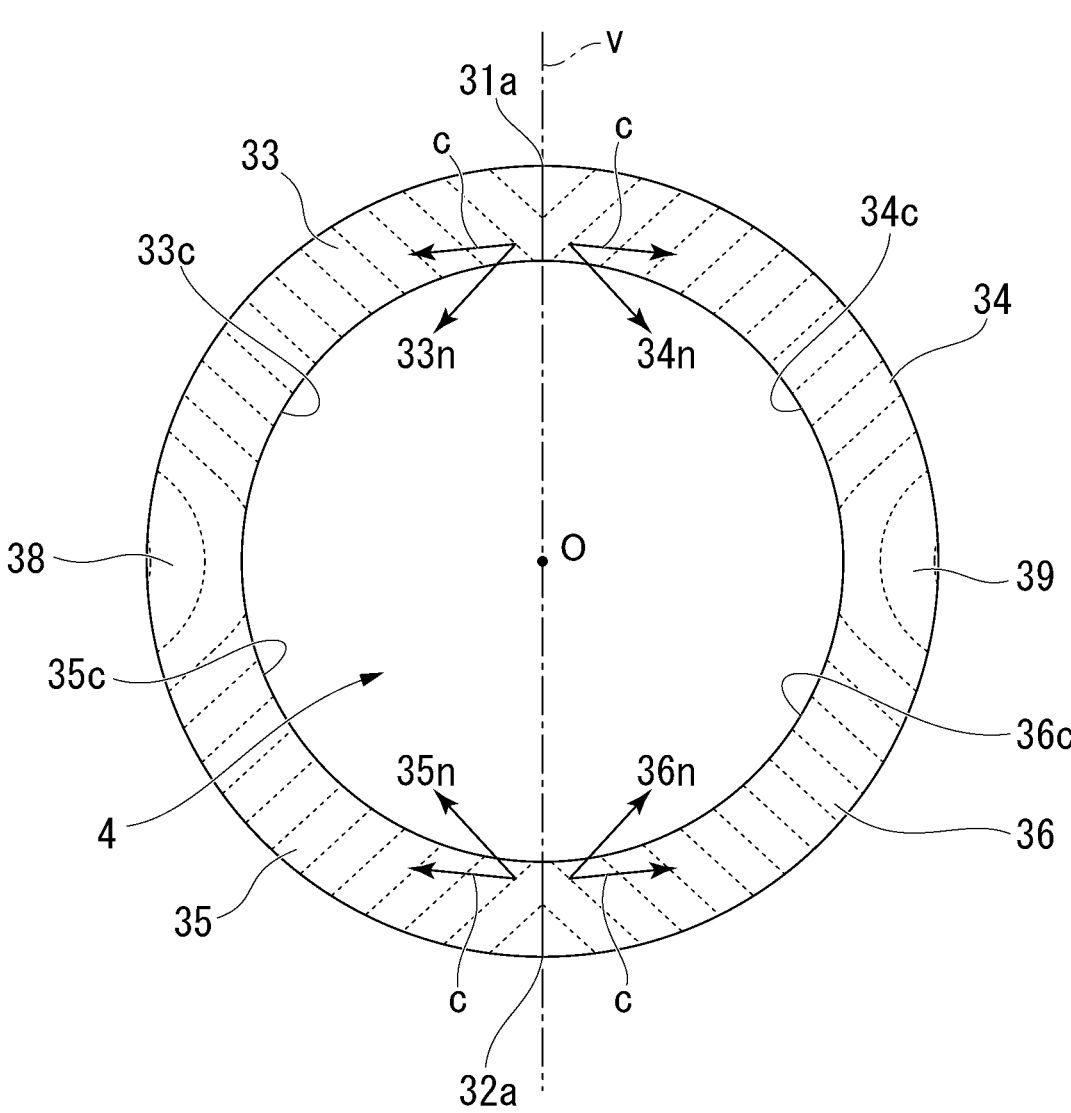
FIG. 6 is a front view of the needle tube seen from a distal end in an axial direction, and is a diagram in which cross sections are arranged at regular intervals in the direction of a longitudinal axis and which schematically shows a change in the orientation of the cross section of each blade surface.
Figures 7, 8:
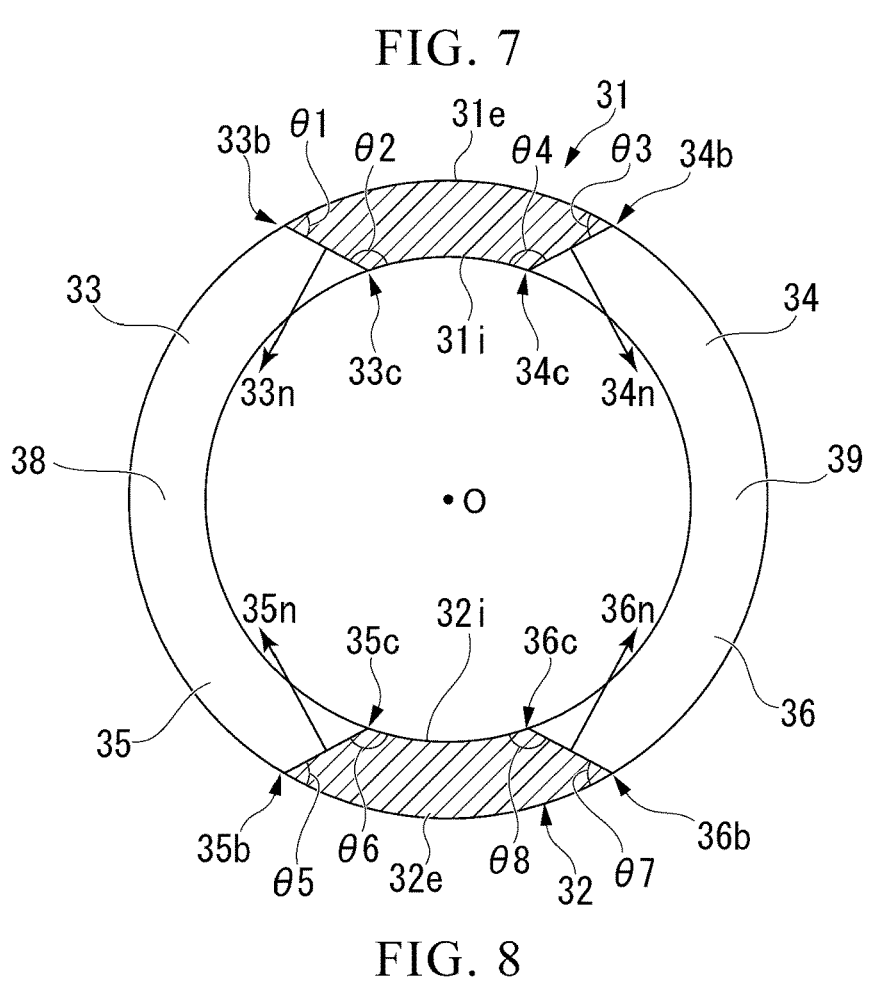
FIG. 7 is a cross-sectional view of the needle tube in a cross section taken along line X-X shown in FIG. 5.
FIG. 8 is a cross-sectional view of the needle tube in a cross section taken along line Y-Y shown in FIG. 5.

FIG. 4 is a perspective view of the needle tube 3. FIG. 5 is a side view of the needle tube 3. FIG. 6 is a front view of the needle tube 3 seen from a distal end in an axial direction A, and is a diagram in which cross sections are arranged at regular intervals in the direction of a longitudinal axis and which schematically shows a change in the orientation of the cross section of each blade surface. A one-dot chain line shown in FIG. 6 indicates a line of intersection between cross sections, which are arranged at regular intervals in the axial direction A and are perpendicular to the axial direction A, and a first blade surface 33, a second blade surface 34, a third blade surface 35, and a fourth blade surface 36. FIG. 7 is a cross-sectional view of the needle tube 3 in a cross section taken along line X-X shown in FIG. 5. FIG. 8 is a cross-sectional view of the needle tube 3 in a cross section taken along line Y-Y shown in FIG. 5.

As shown in FIG. 4, the needle tube 3 includes a tubular portion 30 having a tubular shape, and a first needle tip portion 31 and a second needle tip portion 32 provided at the distal end of the tubular portion 30. The needle tube 3 can be operated to advance and retreat in the sheath 7 by the operation unit 8. An opening 4, which serves as an entrance through which tissue punctured by the first needle tip portion 31 and the second needle tip portion 32 enters the inside of the needle tube 3, is formed at the distal end of the needle tube 3. The first needle tip portion 31 and the second needle tip portion 32 of the needle tube 3 can protrude and retract from an opening formed at the distal end portion of the sheath 7.

It is preferable that the material of the needle tube 3 is a material having flexibility and elasticity, which allows a member to be easily restored to a straight state even though the member is bent by an external force. For example, alloy materials, such as a stainless alloy, a nickel-titanium alloy, and a cobalt-chromium alloy, can be employed as the material of the needle tube 3.

As shown in FIGS. 4 to 6, the first needle tip portion 31 includes a first blade surface 33 and a second blade surface 34 and the first blade surface 33 and the second blade surface 34 extend toward a sharp first needle tip 31a. In a front view seen in a direction along the axial direction A of the needle tube 3, the first blade surface 33 and the second blade surface 34 have shapes symmetric with respect to a straight line V passing through the first needle tip 31a and a second needle tip 32a as shown in FIG. 6. Each of the first blade surface

33 and the second blade surface 34 may be a flat surface, or may be worked into a slightly curved surface.

An outer peripheral surface 31e of the first needle tip portion 31 is a curved surface continuous with an outer peripheral surface 30e of the tubular portion 30, and has the same diameter and curvature as the outer peripheral surface 30e. Further, an inner peripheral surface 31i of the first needle tip portion 31 is a curved surface continuous with an inner peripheral surface 30i of the tubular portion 30, and has the same diameter and curvature as the inner peripheral surface 30i. For example, a part of the tubular portion 30 is cut off, so that the first blade surface 33 and the second blade surface 34 of the first needle tip portion 31 are formed.

As shown in FIGS. 4 to 6, the second needle tip portion 32 includes a third blade surface 35 and a fourth blade surface 36 and the third blade surface 35 and the fourth blade surface 36 extend toward the sharp second needle tip 32a. The first needle tip 31a and the second needle tip 32a are disposed at positions symmetric with respect to a central axis O extending in the axial direction A of the needle tube 3. In a front view seen in a direction along the axial direction A of the needle tube 3, the third blade surface 35 and the fourth blade surface 36 have shapes symmetric with respect to the straight line V passing through the first needle tip 31a and the second needle tip 32a as shown in FIG. 6. Each of the third blade surface 35 and the fourth blade surface 36 may be a flat surface, or may be worked into a slightly curved surface.

An outer peripheral surface 32e of the second needle tip portion 32 is a curved surface continuous with the outer peripheral surface 30e of the tubular portion 30, and has the same diameter and curvature as the outer peripheral surface 30e. Further, an inner peripheral surface 32i of the second needle tip portion 32 is a curved surface continuous with the inner peripheral surface 30i of the tubular portion 30, and has the same diameter and curvature as the inner peripheral surface 30i. For example, a part of the tubular portion 30 is cut off, so that the third blade surface 35 and the fourth blade surface 36 of the second needle tip portion 32 are formed.

As shown in FIGS. 4 and 5, the first needle tip portion 31 and the second needle tip portion 32 form the opening 4 that is surrounded by the first blade surface 33, the second blade surface 34, the third blade surface 35, and the fourth blade surface 36. The opening 4 communicates with the internal space of the tubular portion 30 having a tubular shape.

As shown in FIGS. 4 to 6, the first blade surface 33 and the third blade surface 35 are connected to each other at a first proximal end 38 of the edge of the opening 4. The second blade surface 34 and the fourth blade surface 36 are connected to each other at a second proximal end 39 of the edge of the opening 4.

As shown in FIG. 5, a distal end region 21 that includes the first needle tip 31a and the second needle tip 32a, a proximal end region Z3 that includes the first proximal end 38 and the second proximal end 39, and an intermediate region Z2 that is positioned between the distal end region Z1 and the proximal end region Z3 and is connected to the distal end region Z1 and the proximal end region Z3 are defined at the first needle tip portion 31 and the second needle tip portion 32.

(First Blade Surface 33 and Second Blade Surface 34 of First Needle Tip Portion 31)

As shown in FIGS. 4 and 7, a line of intersection (first inner line 33c of intersection) between the first blade surface 33 and the inner peripheral surface 31i of the first needle tip portion 31 defines a part of the contour of the opening 4. A line of intersection (second inner line 34c of intersection)

between the second blade surface 34 and the inner peripheral surface 31i of the first needle tip portion 31 defines a part of the contour of the opening 4.

As shown in FIG. 7, in a front view seen in a direction along the axial direction A of the needle tube 3 (tubular portion 30), a first facing direction (normal vector 33n) of the first blade surface 33 in the distal end region z1 is directed to the third blade surface 35 in the distal end region Z1 as compared to a direction orthogonal to the straight line V passing through the first needle tip 31a and the second needle tip 32a. Likewise, in the front view, a second facing direction (normal vector 34n) of the second blade surface 34 in the distal end region Z1 is directed to the fourth blade surface 36 in the distal end region Z1 as compared to the direction orthogonal to the straight line V passing through the first needle tip 31a and the second needle tip 32a.

Further, as shown in FIG. 8, a normal vector 33n of the first blade surface 33 in the intermediate region Z2 is also directed to the third blade surface 35 in the intermediate region Z2 as compared to the direction orthogonal to the straight line V as in the distal end region Z1. Furthermore, a normal vector 34n of the second blade surface 34 in the intermediate region Z2 is also directed to the fourth blade surface 36 in the intermediate region Z2 as compared to the direction orthogonal to the straight line V as in the distal end region z1.

Preferably, as shown in FIG. 8, the normal vector 33n of the first blade surface 33 in the intermediate region Z2 is directed to a direction that forms an acute angle with respect to the straight line V connecting the first needle tip 31a to the second needle tip 32a. Further, the normal vector 34n of the second blade surface 34 in the intermediate region Z2 is directed to a direction that forms an acute angle with respect to the straight line V connecting the first needle tip 31a to the second needle tip 32a.

Preferably, as shown in FIGS. 6 and 7, the normal vector 33n of the first blade surface 33 and the normal vector 34n of the second blade surface 34 are directed to a direction, which approaches the central axis O, in the distal end region Z1 as compared to a circumferential direction C of the tubular portion 30.

As shown in FIG. 5, a line of intersection (first distal end line 31b of intersection) between the first blade surface 33 and the second blade surface 34 extends up to the first needle tip 31a from the distal end of the inner peripheral surface 31i of the first needle tip portion 31. Preferably, the first distal end line 31b of intersection is positioned on the straight line V in a front view seen in a direction along the axial direction A of the needle tube 3.

A line of intersection (first outer line 33b of intersection) at which the first blade surface 33 and the outer peripheral surface 31e intersect with each other is a first outer edge 33b including an edge in the circumferential direction of the tubular portion 30. As shown in FIGS. 6 to 8, an angle θ1 formed between the first blade surface 33 and the outer peripheral surface 31e at the first outer edge 33b is an acute angle in the distal end region Z1 in a front view seen in a direction along the axial direction A of the needle tube 3, and the angle θ1 is increased as approaching the intermediate region z2 and is an obtuse angle in the intermediate region z2.

A line of intersection (first inner line 33c of intersection) at which the first blade surface 33 and the inner peripheral surface 31i intersect with each other is a first inner edge 33c including an edge in the circumferential direction of the tubular portion 30. As shown in FIGS. 7 and 8, an angle θ2 formed between the first blade surface 33 and the inner peripheral surface 31i at the first inner edge 33c is an obtuse angle in the distal end region Z1 in a front view seen in a direction along the axial direction A of the needle tube 3, and is an acute angle in the intermediate region z2.

A line of intersection (second outer line 34b of intersection) at which the second blade surface 34 and the outer peripheral surface 31e intersect with each other is a second outer edge 34b including an edge in the circumferential direction of the tubular portion 30. As shown in FIGS. 7 and 8, an angle θ3 formed between the second blade surface 34 and the outer peripheral surface 31e at the second outer edge 34b is an acute angle in the distal end region 21 in a front view seen in a direction along the axial direction A of the needle tube 3, and the angle θ3 is increased as approaching the intermediate region Z2 and is an obtuse angle in the intermediate region Z2.

A line of intersection (second inner line 34c of intersection) at which the second blade surface 34 and the inner peripheral surface 31i intersect with each other is a second inner edge 34c including an edge in the circumferential direction of the tubular portion 30. As shown in FIGS. 7 and 8, an angle θ4 formed between the second blade surface 34 and the inner peripheral surface 31i at the second inner edge 34c is an obtuse angle in the distal end region Z1 in a front view seen in a direction along the axial direction A of the needle tube 3, and is an acute angle in the intermediate region z2.

(Third Blade Surface 35 and Fourth Blade Surface 36 of Second Needle Tip Portion 32)

As shown in FIGS. 4 and 7, a line of intersection (third inner line 35c of intersection) between the third blade surface 35 and the inner peripheral surface 32l of the second needle tip portion 32 defines a part of the contour of the opening 4. A line of intersection (fourth inner line 36c of intersection) between the fourth blade surface 36 and the inner peripheral surface 32i of the second needle tip portion 32 defines a part of the contour of the opening 4.

As shown in FIG. 7, in a front view seen in a direction along the axial direction A of the needle tube 3, a third facing direction (normal vector 35n) of the third blade surface 35 in the distal end region Z1 is directed to the first blade surface 33 in the distal end region Z1 as compared to a direction orthogonal to the straight line V passing through the first needle tip 31a and the second needle tip 32a. Likewise, in the front view, a fourth facing direction (normal vector 36n) of the fourth blade surface 36 in the distal end region Z1 is directed to the second blade surface 34 in the distal end region Z1 as compared to the direction orthogonal to the straight line V passing through the first needle tip 31a and the second needle tip 32a.

Further, as shown in FIG. 8, the normal vector 35n of the third blade surface 35 in the intermediate region Z2 is also directed to the first blade surface 33 in the intermediate region Z2 as compared to the direction orthogonal to the straight line Vas in the distal end region Z1. Furthermore, the normal vector 36n of the fourth blade surface 36 in the intermediate region Z2 is also directed to the second blade surface 34 in the intermediate region Z2 as compared to the direction orthogonal to the straight line V as in the distal end region Z1.

Preferably, as shown in FIGS. 6 to 8, the normal vector 35n of the third blade surface 35 in the intermediate region Z2 is directed to a direction that forms an acute angle with respect to the straight line V connecting the first needle tip 31a to the second needle tip 32a. Further, the normal vector 36n of the fourth blade surface 36 in the intermediate region Z2 is directed to a direction that forms an acute angle with respect to the straight line V connecting the first needle tip 31a to the second needle tip 32a.

Preferably, as shown in FIGS. 6 and 7, the normal vector 35n of the third blade surface 35 and the normal vector 36n of the fourth blade surface 36 are directed to a direction, which approaches the central axis O, in the distal end region 21 as compared to the circumferential direction C of 30 of the tubular portion.

As shown in FIG. 5, a line of intersection (second distal end line 32b of intersection) between the third blade surface 35 and the fourth blade surface 36 extends up to the second needle tip 32a from the distal end of the inner peripheral surface 32i of the second needle tip portion 32. Preferably, the second distal end line 32b of intersection is positioned on the straight line V in a front view seen in a direction along the axial direction A of the needle tube 3.

A line of intersection (third outer line 35b of intersection) at which the third blade surface 35 and the outer peripheral surface 32e intersect with each other is a third outer edge 35b including an edge in the circumferential direction of the tubular portion 30. As shown in FIGS. 6 to 8, an angle θ5 formed between the third blade surface 35 and the outer peripheral surface 32e at the third outer edge 35b is an acute angle in the distal end region Z1 in a front view seen in a direction along the axial direction A of the needle tube 3, and the angle θ5 is increased as approaching the intermediate region Z2 and is an obtuse angle in the intermediate region Z2.

A line of intersection (third inner line 35c of intersection) at which the third blade surface 35 and the inner peripheral surface 32i intersect with each other is a third inner edge 35c including an edge in the circumferential direction of the tubular portion 30. As shown in FIGS. 7 and 8, an angle θ6 formed between the third blade surface 35 and the inner peripheral surface 32i at the third inner edge 35c is an obtuse angle in the distal end region Z1 in a front view seen in a direction along the axial direction A of the needle tube 3, and is an acute angle in the intermediate region Z2.

A line of intersection (fourth outer line 36b of intersection) at which the fourth blade surface 36 and the outer peripheral surface 32e intersect with each other is a fourth outer edge 36b including an edge in the circumferential direction of the tubular portion 30. As shown in FIGS. 7 and 8, an angle θ7 formed between the fourth blade surface 36 and the outer peripheral surface 32e at the fourth outer edge 36b is an acute angle in the distal end region Z1 in a front view seen in a direction along the axial direction of the needle tube 3, and the angle θ7 is increased as approaching the intermediate region Z2 and is an obtuse angle in the intermediate region Z2.

A line of intersection (fourth inner line 36c of intersection) at which the fourth blade surface 36 and the inner peripheral surface 32i intersect with each other is a fourth inner edge 36c including an edge in the circumferential direction of the tubular portion 30. As shown in FIGS. 7 and 8, an angle θ8 formed between the fourth blade surface 36 and the inner peripheral surface 32i at the fourth inner edge 36c is an obtuse angle in the distal end region Z1 in a front view seen in a direction along the axial direction A of the needle tube 3, and is an acute angle in the intermediate region Z2.

As shown in FIG. 3, the sheath 7 preferably includes an outer sheath 71 and an inner sheath 74.

The outer sheath 71 includes a coil body 72 of which strands made of, for example, metal are wound in the shape of a coil about a longitudinal axis as a central axis thereof and a tubular distal end tip 73 that is fixed to the distal end of the coil body 72.

The coil body 72 includes a distal end and a proximal end, and has an outer diameter between the distal end and the proximal end that allows the coil body to be inserted into the channel 107 and an internal space 72a that extends along the longitudinal axis. In consideration of the ease of bending or the restoring force of the coil body 72, stainless steel, a shape memory alloy, a super-elastic alloy, or the like is appropriately selected as the material of the strand of the coil body 72 and a circular cross-sectional shape, a rectangular cross-sectional shape, or the like is appropriately selected as the shape of the strand of the coil body 72.

The distal end tip 73 is a tubular member that is fixed to the distal end surface of the coil body 72 and in which a through-hole into which the needle tube 3 can be inserted is formed.

The inner sheath 74 is, for example, a tubular member that includes a distal end 74a and a proximal end and is made of a resin. The inner sheath 74 is provided in the internal space 72a of the coil body 72 so as to be substantially coaxial with the central axis of the coil body 72. Further, the inner sheath 74 includes an inner peripheral surface 74c and an outer peripheral surface 74d, the inner peripheral surface 74c forms an insertion passage into which the needle tube 3 can be inserted, and the outer peripheral surface 74d is disposed over the strands adjacent to the coil body 72 between the distal end 74a and the proximal end of the inner sheath 74 in the internal space 72a of the coil body 72. The outer peripheral surface 74d covers a gap between the strands, which is generated in a case where the coil body 72 is bent, from the inside of the coil body 72 between the distal end 74a and the proximal end of the inner sheath 74. For this reason, the inner sheath 74 functions as a cover member for the coil body 72. The distal end 74a of the inner sheath 74 is fixed to the distal end tip 73. The proximal end of the inner sheath 74 extends up to the operation unit 109.

The inner sheath 74 can slide with respect to the outer sheath 71 at a portion of the total length of the inner sheath 74 that is closer to a proximal side than a portion where the distal end 74a of the inner sheath 74 and the distal end tip 73 are fixed to each other.

The sheath 7 has a double structure formed of the coil-shaped outer sheath 71 and the inner sheath 74 made of a resin, but may be formed of only one of them.

[Operation Unit 8]

As shown in FIG. 2, the operation unit 8 includes an operation body 9 that is provided at the proximal end portion of the sheath 7, a mounting adapter 18 that is connected to the operation body 9, and a needle slider 23 that is connected to the proximal end portion of the needle tube 3 on the proximal end side of the operation body 9.

The operation body 9 has a cavity into which the needle tube 3 and the sheath 7 can be inserted. The mounting adapter 18 is mounted on the distal end side of the operation body 9. The proximal end side of the operation body 9 is inserted into the needle slider 23 that is formed in a tubular shape. Grooves, protruding portions (not shown), or the like formed on outer peripheral surfaces of the operation body 9 and the mounting adapter 18 and the operation body 9 and the needle slider 23 are engaged with each other, so that the operation body 9 and the mounting adapter 18 and the operation body 9 and the needle slider 23 can slide in an axis direction while the relative rotation thereof about an axis is suppressed.

The needle slider 23 can be moved to a second position where the needle slider 23 is in contact with a stopper 61 being in contact with an increased-diameter portion of the operation body 9 from a first position where the needle slider 23 is locked to the operation body 9. The distal end of the needle tube 3 is adapted to be capable of protruding and retracting from the distal end of the sheath 7 while an operator moves the needle slider 23 between the first position and the second position.

The mounting adapter 18 is movably connected to the operation body 9 so as to be capable of adjusting the protruding length of the sheath 7 from the distal end of the channel 107 of the ultrasound endoscope 100. The distal end portion of the mounting adapter 18 can be attached to and detached from a proximal end cap 107b of the ultrasound endoscope 100.

The needle slider 23 is fixed to the proximal end of the needle tube 3. Further, the needle slider 23 is connected to the operation body 9 so as to be movable relative to the operation body 9. Since the proximal end side of the needle tube 3 protrudes from the proximal end of the sheath 7 and is fixed to the needle slider 23, the needle tube 3 can be caused to protrude and retract from the distal end of the sheath 7 in a case where the needle slider 23 slides with respect to the operation body 9.

The movement of the needle slider 23 is restricted by the stopper 61 as shown in FIG. 2 so that the needle slider 23 can be advanced with respect to the operation body 9 only to a position where the needle slider 23 and the stopper 61 are in contact with each other. The fixing position of the stopper 61 with respect to the operation body 9 is adjusted, so that the maximum protruding length of the needle tube 3 from the sheath 7 can be adjusted.

A state in which the needle slider 23 is present at a position where the needle slider 23 is moved to the limit on the proximal end side of the operation body 9 is an initial state in which the use of the puncture needle 1 is not yet started. In the initial state, the distal end of the needle tube 3 is present in the sheath 7.

[Stylet 27]

The stylet 27 is mounted on the proximal end portion of the needle slider 23. The stylet 27 is a needle-shaped member that is to be inserted into the needle tube 3. The distal end of the stylet 27 is not limited to the shape of a needle, and may have an end surface formed along a surface intersecting with the longitudinal axis of the stylet 27 or may have a curved surface, such as a hemispherical surface.

Figure 9:
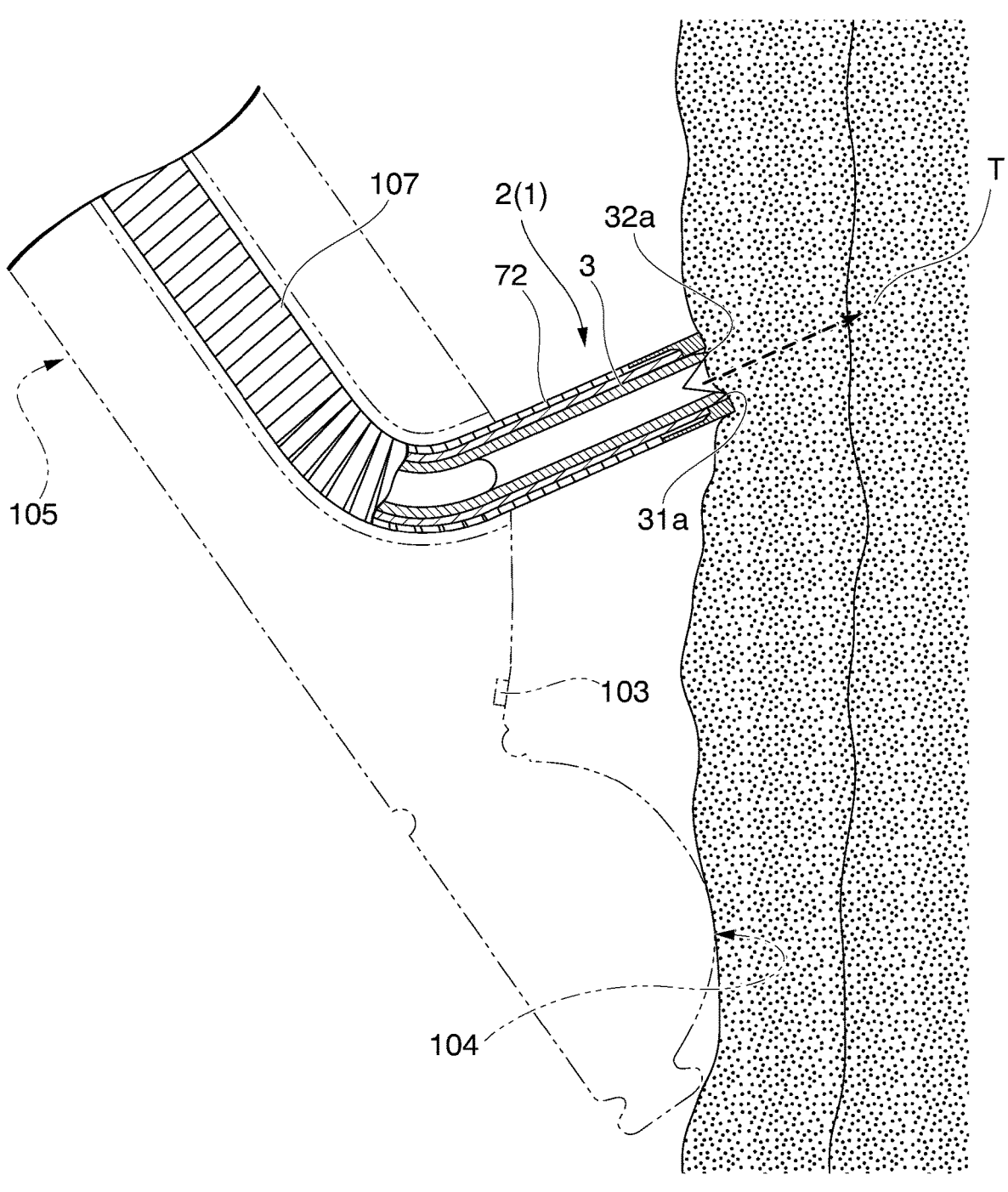
FIG. 9 is a diagram illustrating the action of the endoscope puncture needle.

Next, the action of the biopsy system 150 of this embodiment will be described. FIG. 9 is a diagram illustrating the action of the puncture needle 1. A treatment for a biopsy in which the needle tube 3 of the puncture needle 1 is inserted into a lesion present in a body as target tissue and cells or the like of the lesion are collected through the inside of the needle tube 3 will be described below by way of example. An object to which the puncture needle 1 according to the embodiment is to be applied is not limited to puncture for a biopsy to the pancreatic head.

First, an operator inserts the insertion unit 101 of the ultrasound endoscope 100 shown in FIG. 1 into a body, and appropriately bends the active bendable part 105 to introduce the distal end portion of the insertion unit 101 to the vicinity of target tissue (the pancreatic head in this embodiment) while making an observation by the optical image pickup mechanism 103. After the introduction, the operator determines a portion, which is to be subjected to a biopsy, on the basis of the observation results obtained from the optical image pickup mechanism 103 and the ultrasound scanning mechanism 104. For example, in a case where the operator is to perform a biopsy for the pancreatic head, the operator moves the insertion unit 101 while maintaining a state in which the active bendable part 105 is bent so that the optical image pickup mechanism 103 and the ultrasound scanning mechanism 104 provided in the insertion unit 101 of the ultrasound endoscope 100 reach the duodenum.

In a case where the operator is to perform a biopsy for the pancreatic head using the ultrasound endoscope 100, the operator needs to bend the active bendable part 105 in order to capture a portion to be punctured by the puncture needle 1 in the field of view of the ultrasound endoscope 100. Particularly, in a case where a biopsy for the pancreatic head is to be performed as in this embodiment, the active bendable part 105 is bent up to the extent close to the limit of performance of the active bendable part 105 of the ultrasound endoscope 100.

Next, the operator inserts the insertion body 2 of the puncture needle 1 into the channel 107 from the proximal end cap 107b that is provided on the operation unit 109 of the ultrasound endoscope 100 shown in FIG. 1. Then, the operator connects the mounting adapter 18 of the operation unit 109 to the proximal end cap 107b. Accordingly, the operation unit 8 of the puncture needle 1 is fixed to the ultrasound endoscope 100 not to be rotated relative to the operation unit 109.

After that, the operator loosens a fixing screw 10 (see FIG. 2), and appropriately adjusts the protruding length of the sheath 7 from the distal end of the insertion unit 101 of the ultrasound endoscope 100 to an appropriate length by causing the mounting adapter 18 and the operation body 9 to slide relative to each other while observing the sheath 7 and the inside of the body by the optical image pickup mechanism 103 and the ultrasound scanning mechanism 104. After the adjustment, the operator tightens the fixing screw 10 to fix the protruding length of the sheath 7. In this case, the distal end of the coil body 72 is positioned in the observation field of view of an observation optical system of the ultrasound endoscope 100, and the needle slider 23 is moved to the first position.

Next, the operator advances the needle tube 3 with respect to the coil body 72. In this case, the coil body 72 of the outer sheath 71 is bent by the active bendable part 105, so that a gap is generated between the strands forming the coil body 72. However, in this embodiment, the inner sheath 74 is disposed in the internal space of the coil body 72 of the outer sheath 71 and a gap between the strands of the coil body 72 is covered with the inner sheath 74 from the inside of the coil body 72. As a result, the needle tube 3 moving in the inner sheath 74 is less likely to be caught by the gap of the strands of the coil body 72 even though the insertion body 2 is bent at the position of the active bendable part 105.

Next, the operator moves the stopper 61 while considering a distance to target tissue T, which is an object to be subjected to a biopsy, on the basis of the observation results obtained from the ultrasound scanning mechanism 104; and fixes the stopper 61 to the operation body 9 at a desired position to adjust the maximum protruding length of the needle tube 3 from the sheath 7.

Next, the operator advances the needle slider 23 to the distal end side of the operation unit 8. In a case where the needle tube 3 protrudes from the sheath 7, the operator pulls the stylet 27 back into the needle tube 3 as shown in FIG. 9. Accordingly, the needle tube 3 can puncture tissue by the sharp needle tips (the first needle tip 31a and the second needle tip 32a) of the needle tube 3.

After that, in a case where the operator further advances the needle slider 23 to the distal end side of the operation unit 8 in a state in which the distal end of the sheath 7 is in contact with the intestinal wall, the needle tips (the first needle tip 31*a* and the second needle tip 32*a*) of the needle tube 3 protrude from the distal end of the sheath 7, puncture tissue, and are pushed to the target tissue T that is an object to be subjected to a biopsy as shown in FIG. 9. In this case, the stylet 27 is disposed in the needle tube 3 in order to prevent the tissue, which is not an object to be subjected to a biopsy, from entering the needle tube 3.

The operator can acquire the position information of the distal end portion of the needle tube 3, which is inserted into the tissue, by the ultrasound scanning mechanism 104. For this reason, the operator can observe an ultrasound image, which is the image of the distal end portion of the needle tube 3 acquired by the ultrasound scanning mechanism 104, using the ultrasound observation unit 115 shown in FIG. 1. The operator can cause the needle tips (the first needle tip 31*a* and the second needle tip 32*a*) of the needle tube 3 to reach the target tissue T, which is an object to be subjected to a biopsy, with reference to the image of the distal end portion of the needle tube 3 that is clearly displayed by the ultrasound observation unit 115.

Figure 10:
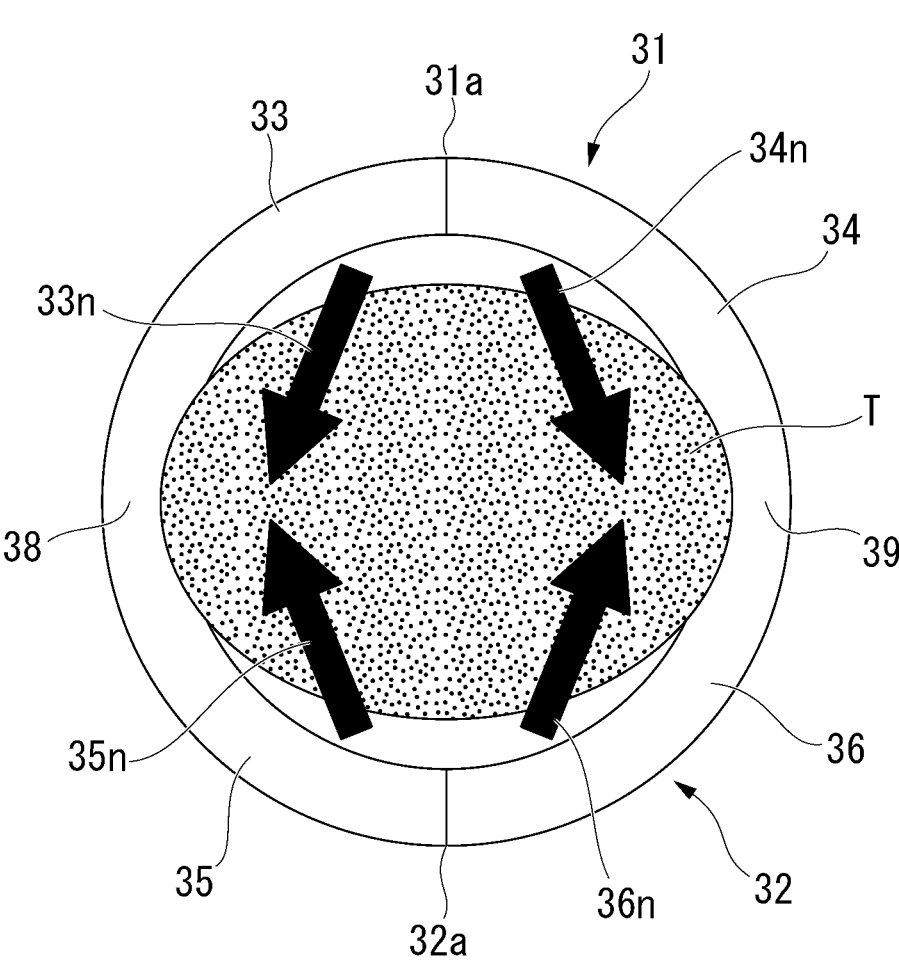
FIG. 10 is a diagram showing target tissue in a case where a needle slider is advanced to the distal end side of an operation unit.

FIG. 10 is a diagram showing the target tissue T in a case where the needle slider 23 is advanced to the distal end side of the operation unit 8. The normal vector 33*n* of the first blade surface 33 and the normal vector 34*n* of the second blade surface 34 are directed to a direction, which approaches the central axis O, at the first needle tip 31*a* as compared to the circumferential direction C of 30 of the tubular portion. Further, the normal vector 35*n* of the third blade surface 35 and the normal vector 36*n* of the fourth blade surface 36 are directed to a direction, which approaches the central axis O, at the second needle tip 32*a* as compared to the circumferential direction C of 30 of the tubular portion. For this reason, the needle tube 3 can allow the cut-out target tissue T to be suitably moved into the needle tube 3.

In a case where the operator further advances the needle slider 23 to the distal end side of the operation unit 8, the target tissue T is cut out by the first outer edge 33*b*, the second outer edge 34*b*, the third outer edge 35*b*, and the fourth outer edge 36*b*. Since the first outer edge 33*b*, the second outer edge 34*b*, the third outer edge 35*b*, and the fourth outer edge 36*b* have acute angles in the distal end region Z1, the target tissue T can be suitably cut out.

In order to suck the tissue into the needle tube 3, the operator pulls the stylet 27 out of the insertion body 2 and the operation unit 8. Accordingly, a through-hole, which extends up to the proximal end of the needle slider 23 from the distal end of the needle tube 3, is formed. The operator connects a syringe or the like to a port provided at the proximal end of the needle slider 23 to suck the tissue present in the needle tube 3, and sucks cells or the like of the target tissue T from the distal end of the needle tube 3 to collect the cells or the like of the target tissue T.

In a case where the required amount of cells or the like can be collected, the operator retreats the needle slider 23 to the proximal end side of the operation unit 8 to pull the needle tube 3 out of the tissue and houses the distal end of the needle tube 3 in the sheath 7. In a case where the needle tube 3 is pulled out of the tissue, the operator removes the mounting adapter 18 from the proximal end cap 107*b* of the operation unit 109 of the ultrasound endoscope 100 and removes the puncture needle 1 from the channel 107.

Finally, the operator removes the ultrasound endoscope 100 from a patient and ends a series of treatments.

According to the biopsy system 150 including the puncture needle 1 according to this embodiment, punctureability into body tissue is high (the puncture needle 1 easily cuts into the body tissue) and it is easy to collect the cut-out body tissue (a sample required for diagnosis) into the puncture needle 1. The normal vector 33*n* of the first blade surface 33 and the normal vector 34*n* of the second blade surface 34 in the distal end region Z1 are directed to the third blade surface 35 and the fourth blade surface 36 in the distal end region Z1, respectively, as compared to a direction that is orthogonal to the straight line V passing through the first needle tip 31*a* and the second needle tip 32*a*. Further, in the front view, the normal vector 35*n* of the third blade surface 35 and the normal vector 36*n* of the fourth blade surface 36 in the distal end region Z1 are directed to the first blade surface 33 and the second blade surface 34 in the distal end region Z1 as compared to a direction that is orthogonal to the straight line V passing through the first needle tip 31*a* and the second needle tip 32*a*. For this reason, the puncture needle 1 can allow the target tissue T to be suitably moved into the needle tube 3.

Further, the first outer edge 33*b*, the second outer edge 34*b*, the third outer edge 35*b*, and the fourth outer edge 36*b* of the puncture needle 1 have acute angles in the distal end region Z1 and the target tissue T can be suitably cut out in a case where the operator further advances the needle slider 23 to the distal end side of the operation unit 8.

The above embodiment of the present disclosure has been described in detail above with reference to the drawings, but specific configuration is not limited to this embodiment and also includes design changes and the like without departing from the scope of the present disclosure. Further, components shown in the above-mentioned embodiment and a modification example can be appropriately combined.

The outer peripheral surface 31*e* of the first needle tip portion 31 and the outer peripheral surface 32*e* of the second needle tip portion 32 are not worked in the embodiment, but aspects of the first needle tip portion and the second needle tip portion are not limited thereto.

Figure 11:
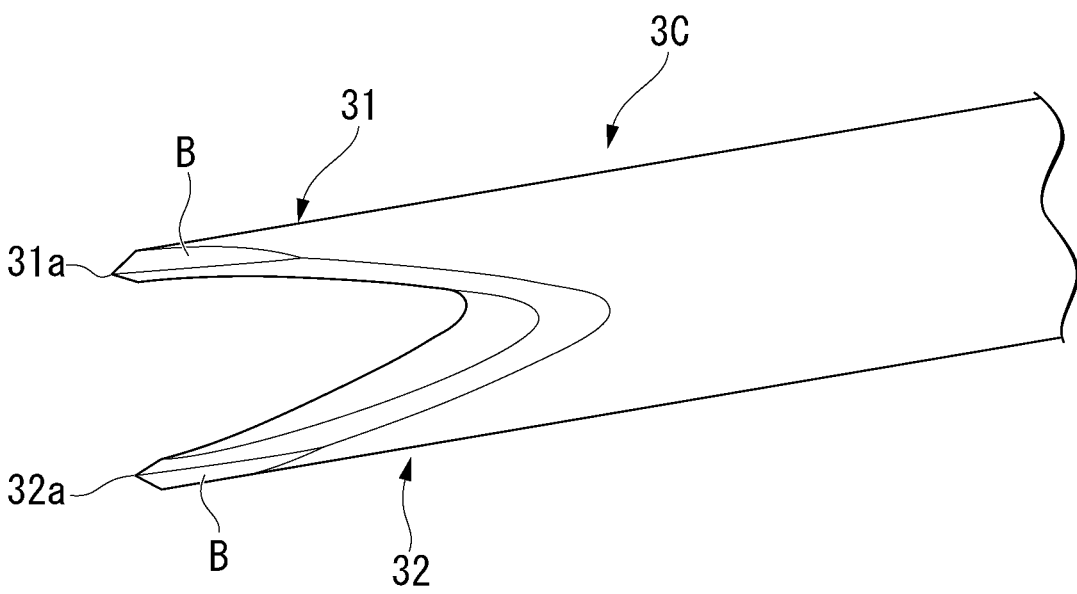
FIG. 11 is a perspective view showing a modification example of the endoscope puncture needle.

Back cutting B is performed on the outer peripheral surfaces of a first needle tip portion 31 and a second needle tip portion 32 of a needle tube 3C that is a modification example of the needle tube 3 shown in FIG. 11. The first needle tip portion 31 and the second needle tip portion 32 have higher insertability into body tissue. That is, needle tips 31*a* and 32*a* are easily inserted into the surface of body tissue. Further, since the needle tips 31*a* and 32*a* are less likely to be in contact with the inner surface of the sheath 7, the needle tube 3C has high operability.

Figure 12:
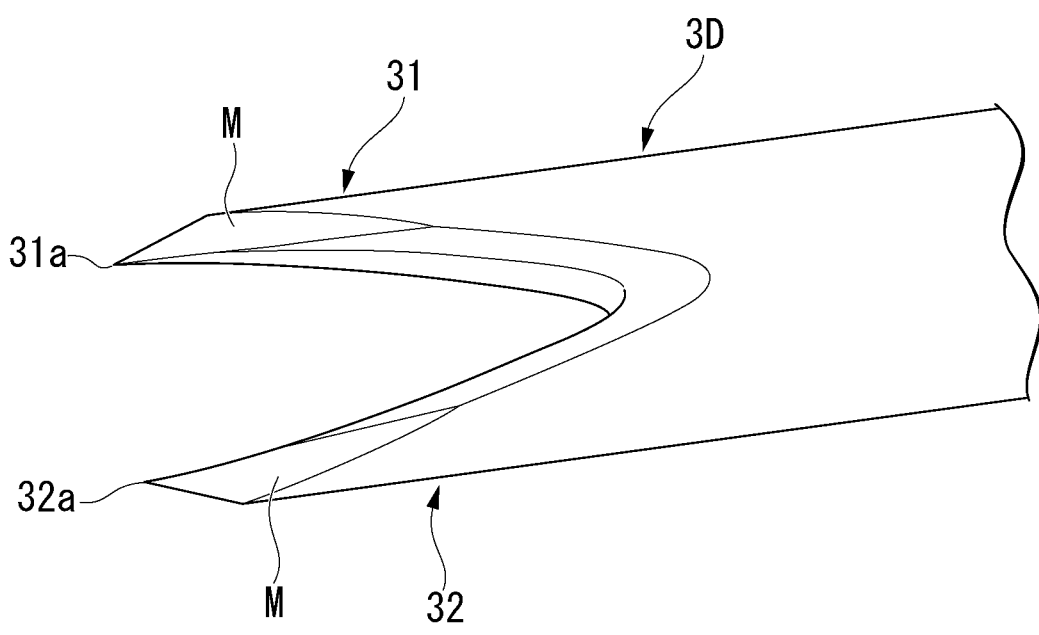
FIG. 12 is a perspective view showing a modification example of the endoscope puncture needle.

A cut surface M, which is formed by conical cutting centered on inner peripheral surfaces (31*i* and 32*l*) as an axis, is formed on at least a part of the outer peripheral surface of a needle tube 3D, which is a modification example of the needle tube 3 shown in FIG. 12, in the distal end region Z1. The first needle tip portion 31 and the second needle tip portion 32 have higher insertability into body tissue. That is, needle tips 31*a* and 32*a* are easily inserted into the surface of body tissue. Further, since the needle tips 31*a* and 32*a* are less likely to be in contact with the inner surface of the sheath 7, the needle tube 3D has high operability. A curvature radius of the active bendable part 105 of the endoscope 100 when being bent to the maximum degree is small, thus a curvature radius of the channel 107 enters a small state. In this state, the endoscope puncture needle 1 passing through the channel 107 is also bent to be in a small curvature radius. When the endoscope puncture needle 1 passes through the channel 107 when the activate bendable part 105 is bent to the maximum degree, the sheath 7 is bent in a state in which the needle tube is accommodated in the sheath 7 (inner sheath 74). The needle tube 3C shown in FIG. 11 and the needle tube 3D shown in FIG. 12 are configured such that the needle tips 31a, 32a are formed in the inner peripheral surface of the needle tubes respectively, thus it is impossible that the needle tips 31a, 32a puncture into the inner peripheral surface of the bent sheath 7 (inner sheath 74) and get stuck thereto.

A biopsy system 150B including an endoscope puncture needle 1B according to another exemplary embodiment of the present disclosure will be described with reference to FIGS. 13 to 17. In the following description, components common to the already described components will be denoted by the same reference numerals and the repeated description thereof will be omitted.

[Biopsy System 150B]

The biopsy system 150B is medical equipment that is used to collect tissue in a body during a biopsy. The biopsy system 150B includes an ultrasound endoscope 100 and an endoscope puncture needle 1B (hereinafter, simply referred to as a "puncture needle 1B".). The puncture needle 1B includes an insertion body 2B, an operation unit 8, and a stylet 27.

[Insertion Body 2B]

The insertion body 2B is an elongated member that can be inserted into a channel 107 of the ultrasound endoscope 100. The insertion body 2B includes a needle tube 3B and a sheath 7.

Figure 13:
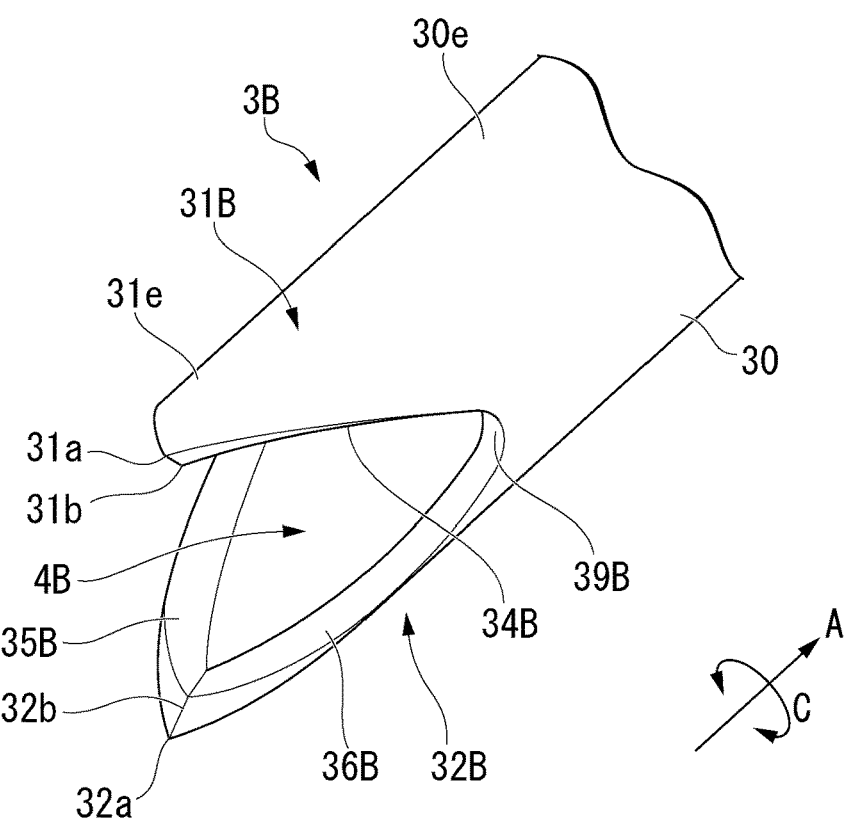
FIG. 13 is a perspective view of a needle tube included in an endoscope puncture needle according to an exemplary embodiment.
Figure 14:
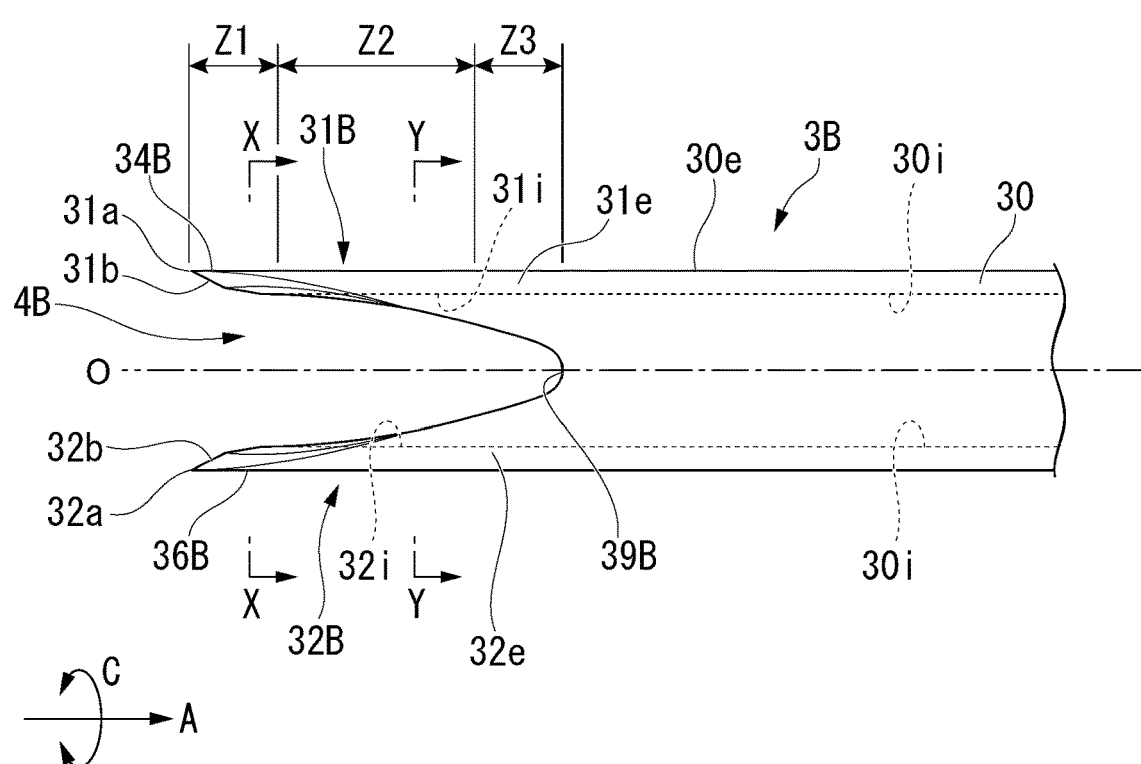
FIG. 14 is a side view of the needle tube.
Figure 15:
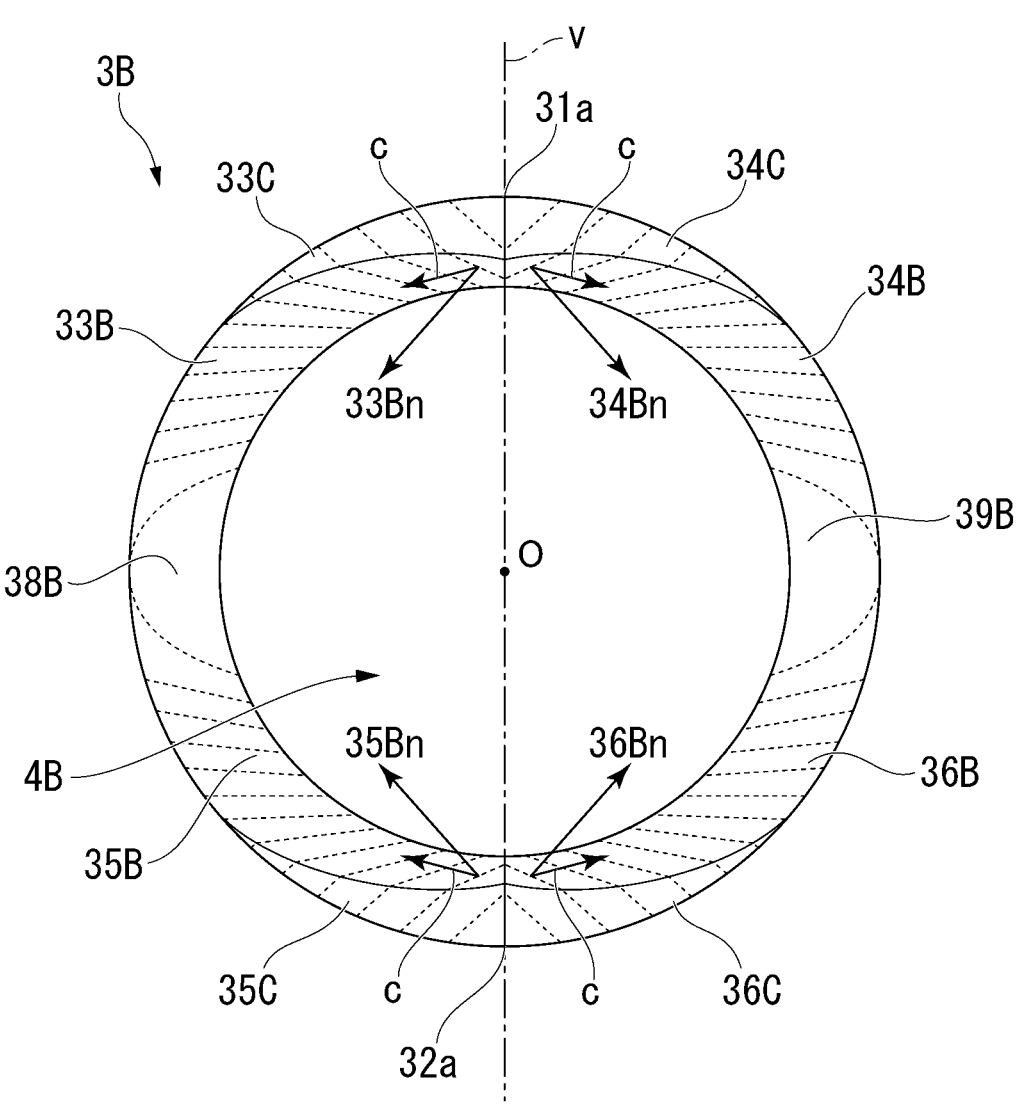
FIG. 15 is a front view of the needle tube seen from a distal end in an axial direction, and is a diagram in which cross sections are arranged at regular intervals in the direction of a longitudinal axis and which schematically shows a change in the orientation of the cross section of each blade surface.
Figure 16:
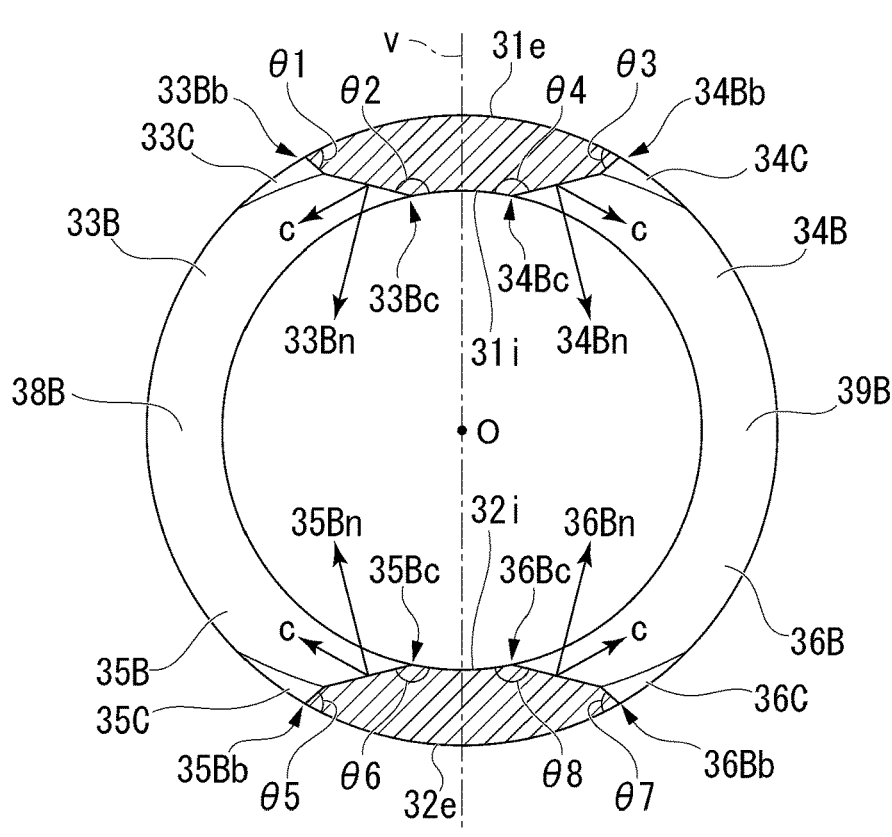
FIG. 16 is a cross-sectional view of the needle tube in a cross section taken along line X-X shown in FIG. 14.
Figure 17:
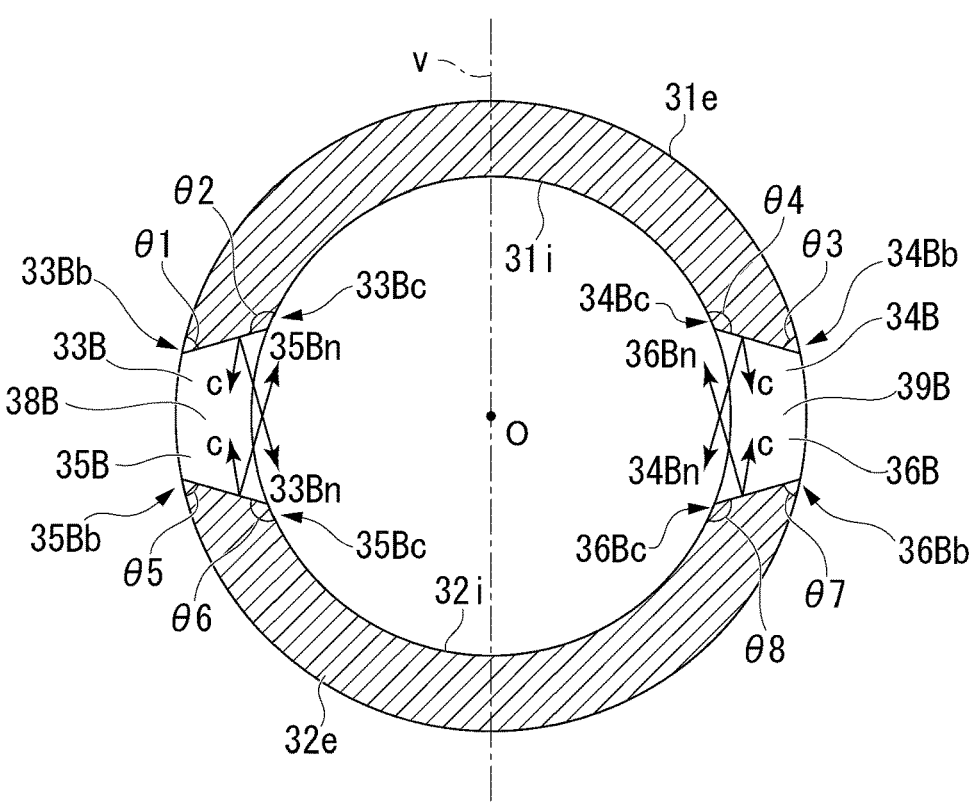
FIG. 17 is a cross-sectional view of the needle tube in a cross section taken along line Y-Y shown in FIG. 14.

FIG. 13 is a perspective view of the needle tube 3B. FIG. 14 is a side view of the needle tube 3B. FIG. 15 is a front view of the needle tube 3B seen from a distal end in an axial direction A, and is a diagram in which cross sections are arranged at regular intervals in the direction of a longitudinal axis and which schematically shows a change in the orientation of the cross section of each blade surface. A one-dot chain line shown in FIG. 15 indicates a line of intersection between cross sections, which are arranged at regular intervals in the axial direction A and are perpendicular to the axial direction A, and a first blade surface 33B, a second blade surface 34B, a third blade surface 35B, and a fourth blade surface 36B. FIG. 16 is a cross-sectional view of the needle tube 3B in a cross section taken along line X-X shown in FIG. 14. FIG. 17 is a cross-sectional view of the needle tube 3B in a cross section taken along line Y-Y shown in FIG. 14.

As shown in FIG. 13, the needle tube 3B includes a tubular portion 30 having a tubular shape, and a first needle tip portion 31B and a second needle tip portion 32B provided at the distal end of the tubular portion 30. The needle tube 3B can be operated to advance and retreat in the sheath 7 by the operation unit 8. An opening 4B, which serves as an entrance through which tissue punctured by the first needle tip portion 31B and the second needle tip portion 32B enters the inside of the needle tube 3B, is formed at the distal end of the needle tube 3B. The first needle tip portion 31B and the second needle tip portion 32B of the needle tube 3B can protrude and retract from an opening formed at the distal end portion of the sheath 7.

As shown in FIGS. 13 and 15, the first needle tip portion 31B includes a first blade surface 33B and a second blade surface 34B and the first blade surface 33B and the second blade surface 34B extend toward a sharp first needle tip 31a. In a front view seen in a direction along the axial direction A of the needle tube 3B (tubular portion 30), the first blade surface 33B and the second blade surface 34B have shapes symmetric with respect to a straight line V passing through the first needle tip 31a and a second needle tip 32a as shown in FIG. 15. Each of the first blade surface 33B and the second blade surface 34B may be a flat surface, or may be worked into a slightly curved surface.

An outer peripheral surface 31e of the first needle tip portion 31B is a curved surface continuous with an outer peripheral surface 30e of the tubular portion 30, and has the same diameter and curvature as the outer peripheral surface 30e. Further, an inner peripheral surface 31i of the first needle tip portion 31B is a curved surface continuous with an inner peripheral surface 30i of the tubular portion 30, and has the same diameter and curvature as the inner peripheral surface 30i. For example, a part of the tubular portion 30 is cut off, so that the first blade surface 33B and the second blade surface 34B of the first needle tip portion 31B are formed.

As shown in FIG. 13, the second needle tip portion 32B includes a third blade surface 35B and a fourth blade surface 36B and the third blade surface 35B and the fourth blade surface 36B extend toward the sharp second needle tip 32a. The first needle tip 31a and the second needle tip 32a are disposed at positions symmetric with respect to a central axis O extending in the axial direction A of the needle tube 3B. In a front view seen in a direction along the axial direction A of the needle tube 3B, the third blade surface 35B and the fourth blade surface 36B have shapes symmetric with respect to the straight line V passing through the first needle tip 31a and the second needle tip 32a as shown in FIG. 15. Each of the third blade surface 35B and the fourth blade surface 36B may be a flat surface, or may be worked into a slightly curved surface.

An outer peripheral surface 32e of the second needle tip portion 32B is a curved surface continuous with the outer peripheral surface 30e of the tubular portion 30, and has the same diameter and curvature as the outer peripheral surface 30e. Further, an inner peripheral surface 32l of the second needle tip portion 32B is a curved surface continuous with the inner peripheral surface 30i of the tubular portion 30, and has the same diameter and curvature as the inner peripheral surface 30i. For example, a part of the tubular portion 30 is cut off, so that the third blade surface 35B and the fourth blade surface 36B of the second needle tip portion 32B are formed.

As shown in FIGS. 13 to 15, the first needle tip portion 31B and the second needle tip portion 32B form the opening 4B that is surrounded by the first blade surface 33B, the second blade surface 34B, the third blade surface 35B, and the fourth blade surface 36B. The opening 4B communicates with the internal space of the tubular portion 30 having a tubular shape.

As shown in FIGS. 13 to 15, the first blade surface 33B and the third blade surface 35B are connected to each other at a first proximal end 38B of the opening 4B. The second blade surface 34B and the fourth blade surface 36B are connected to each other at a second proximal end 39B of the opening 4B.

As shown in FIG. 14, a distal end region Z1 that includes the first needle tip 31a and the second needle tip 32a, a proximal end region 23 that includes the first proximal end 38B and the second proximal end 39B, and an intermediate region 22 that is positioned between the distal end region Z1 and the proximal end region 23 and is connected to the distal end region Z1 and the proximal end region 23 are defined at the first needle tip portion 31B and the second needle tip portion 32B.

(First Blade Surface 33B and Second Blade Surface 34B of First Needle Tip Portion 31B)

As shown in FIGS. 13 and 16, a line of intersection (first inner line 33Bc of intersection) between the first blade surface 33B and the inner peripheral surface 31$i$ of the first needle tip portion 31B defines a part of the contour of the opening 4B. A line of intersection (second inner line 34Bc of intersection) between the second blade surface 34B and the inner peripheral surface 31$i$ of the first needle tip portion 31B defines a part of the contour of the opening 4B.

As shown in FIG. 16, in a front view seen in a direction along the axial direction A of the needle tube 3B, a normal vector 33Bn of the first blade surface 33B in the distal end region Z1 is directed to the third blade surface 35B in the distal end region Z1 as compared to a direction orthogonal to the straight line V passing through the first needle tip 31$a$ and the second needle tip 32$a$. Likewise, in the front view, a normal vector 34Bn n of the second blade surface 34B in the distal end region Z1 is directed to the fourth blade surface 36B in the distal end region Z1 as compared to the direction orthogonal to the straight line V passing through the first needle tip 31$a$ and the second needle tip 32$a$.

Further, as shown in FIG. 17, a normal vector 33Bn of the first blade surface 33B in the intermediate region Z2 is also directed to the third blade surface 35B in the intermediate region Z2 as compared to the direction orthogonal to the straight line V as in the distal end region Z1. Furthermore, a normal vector 34Bn of the second blade surface 34B in the intermediate region Z2 is also directed to the fourth blade surface 36B in the intermediate region Z2 as compared to the direction orthogonal to the straight line V as in the distal end region Z1.

Preferably, as shown in FIG. 17, the normal vector 33Bn of the first blade surface 33B in the intermediate region Z2 is directed to a direction that forms an acute angle with respect to the straight line V connecting the first needle tip 31$a$ to the second needle tip 32$a$. Further, the normal vector 34Bn of the second blade surface 34B in the intermediate region 22 is directed to a direction that forms an acute angle with respect to the straight line V connecting the first needle tip 31$a$ to the second needle tip 32$a$.

Preferably, as shown in FIGS. 15 and 16, the normal vector 33Bn of the first blade surface 33B is directed to a direction, which approaches the central axis O, in the distal end region Z1 as compared to a circumferential direction C of the tubular portion 30.

As shown in FIG. 14, a line of intersection (first distal end line 31$b$ of intersection) between the first blade surface 33B and the second blade surface 34B extends up to the first needle tip 31$a$ from the distal end of the inner peripheral surface 31$i$ of the first needle tip portion 31B. The first distal end line 31$b$ of intersection is positioned on the straight line V in a front view seen in a direction along the axial direction A of the needle tube 3B.

The first blade surface 33B further includes a first cutting blade surface 33C on the distal end side thereof in the distal end region Z1. A normal vector of the first cutting blade surface 33C is directed to a direction that forms an acute angle with respect to the straight line V, and the normal vector 33Bn of the first blade surface 33B is directed to a direction that forms an acute angle with respect to the straight line V smaller than the angle between the normal vector of the first cutting blade surface 33C and the straight line V. As shown in FIGS. 13 to 16, a ridge line at which the first blade surface 33B and the first cutting blade surface 33C intersect with each other extends toward the intermediate region 22 from the first distal end line 31$b$ of intersection.

The second blade surface 34B further includes a second cutting blade surface 34C on the distal end side thereof in the distal end region Z1. A normal vector of the second cutting blade surface 34C is directed to a direction that forms an acute angle with respect to the straight line V, and the normal vector 34Bn of the second blade surface 34B is directed to a direction that forms an acute angle with respect to the straight line V smaller than the angle between the normal vector of the second cutting blade surface 34C and the straight line V. As shown in FIGS. 13 to 16, a ridge line at which the second blade surface 34B and the second cutting blade surface 34C intersect with each other extends toward the intermediate region Z2 from the first distal end line 31$b$ of intersection.

A line of intersection (first outer line 33Bb of intersection) at which the first blade surface 33B and the outer peripheral surface 31$e$ intersect with each other is a first outer edge 33Bb including an edge in the circumferential direction of the tubular portion 30. As shown in FIGS. 16 and 17, an angle θ1 formed between the first blade surface 33B and the outer peripheral surface 31$e$ at the first outer edge 33Bb is an acute angle in the distal end region Z1 and the intermediate region Z2 in a front view seen in a direction along the axial direction A of the needle tube 3B.

A line of intersection (first inner line 33Bc of intersection) at which the first blade surface 33B and the inner peripheral surface 31$i$ intersect with each other is a first inner edge 33Bc including an edge in the circumferential direction of the tubular portion 30. As shown in FIGS. 16 and 17, an angle θ2 formed between the first blade surface 33B and the inner peripheral surface 31$i$ at the first inner edge 33Bc is an obtuse angle in the distal end region z1 and the intermediate region Z2.

A line of intersection (second outer line 34Bb of intersection) at which the second blade surface 34B and the outer peripheral surface 31$e$ intersect with each other is a second outer edge 34Bb including an edge in the circumferential direction of the tubular portion 30. As shown in FIGS. 16 and 17, an angle θ3 formed between the second blade surface 34B and the outer peripheral surface 31$e$ at the second outer edge 34Bb is an acute angle in the distal end region Z1 and the intermediate region Z2.

A line of intersection (second inner line 34Bc of intersection) at which the second blade surface 34B and the inner peripheral surface 31$i$ intersect with each other is a second inner edge 34Bc including an edge in the circumferential direction of the tubular portion 30. As shown in FIGS. 16 and 17, an angle θ4 formed between the second blade surface 34B and the inner peripheral surface 31$i$ at the second inner edge 34Bc is an obtuse angle in the distal end region Z1 and the intermediate region Z2.

(Third Blade Surface 35B and Fourth Blade Surface 36B of Second Needle Tip Portion 32B)

As shown in FIGS. 13 and 16, a line of intersection (third inner line 35Bc of intersection) between the third blade surface 35B and the inner peripheral surface 32$l$ of the second needle tip portion 32B defines a part of the contour of the opening 4B. A line of intersection (fourth inner line 36Bc of intersection) between the fourth blade surface 36B and the inner peripheral surface 32$i$ of the second needle tip portion 32B defines a part of the contour of the opening 4B.

In a front view seen in a direction along the axial direction A of the needle tube 3B, a normal vector 35Bn of the third blade surface 35B in the distal end region Z1 is directed to the first blade surface 33B in the distal end region Z1 as compared to a direction orthogonal to the straight line V passing through the first needle tip 31$a$ and the second needle tip 32a. Likewise, in the front view, a normal vector 36Bn of the fourth blade surface 36B in the distal end region 21 is directed to the second blade surface 34B in the distal end region 21 as compared to the direction orthogonal to the straight line V passing through the first needle tip 31a and the second needle tip 32a.

Further, the normal vector 35Bn of the third blade surface 35B in the intermediate region z2 is also directed to the first blade surface 33B in the intermediate region Z2 as compared to the direction orthogonal to the straight line Vas in the distal end region Z1. Furthermore, the normal vector 36Bn of the fourth blade surface 36B in the intermediate region Z2 is also directed to the second blade surface 34B in the intermediate region Z2 as compared to the direction orthogonal to the straight line V as in the distal end region Z1.

Preferably, as shown in FIGS. 15 to 17, the normal vector 35Bn of the third blade surface 35B in the intermediate region Z2 is directed to a direction that forms an acute angle with respect to the straight line V connecting the first needle tip 31a to the second needle tip 32a. Further, the normal vector 36Bn of the fourth blade surface 36B in the intermediate region Z2 is directed to a direction that forms an acute angle with respect to the straight line V connecting the first needle tip 31a to the second needle tip 32a.

Preferably, as shown in FIGS. 15 and 16, the normal vector 35Bn of the third blade surface 35B is directed to a direction, which approaches the central axis O, in the distal end region Z1 as compared to the circumferential direction C of the tubular portion 30.

As shown in FIG. 14, a line of intersection (second distal end line 32b of intersection) between the third blade surface 35B and the fourth blade surface 36B extends up to the second needle tip 32a from the distal end of the inner peripheral surface 32i of the second needle tip portion 32B. The second distal end line 32b of intersection is positioned on the straight line V in a front view seen in a direction along the axis of the needle tube 3B.

The third blade surface 35B further includes a third cutting blade surface 35C on the distal end side thereof in the distal end region Z1. A normal vector of the third cutting blade surface 35C is directed to a direction that forms an acute angle with respect to the straight line V, and the normal vector 35Bn of the third blade surface 35B is directed to a direction that forms an acute angle with respect to the straight line V smaller than the angle between the normal vector of the third cutting blade surface 35C and the straight line V. As shown in FIGS. 13 to 16, a ridge line at which the third blade surface 35B and the third cutting blade surface 35C intersect with each other extends toward the intermediate region Z2 from the second distal end line 32b of intersection.

The fourth blade surface 36B further includes a fourth cutting blade surface 36C on the distal end side thereof in the distal end region Z1. A normal vector of the fourth cutting blade surface 36C is directed to a direction that forms an acute angle with respect to the straight line V, and the normal vector 36Bn of the fourth blade surface 36B is directed to a direction that forms an acute angle with respect to the straight line V smaller than the angle between the normal vector of the fourth cutting blade surface 36C and the straight line V. As shown in FIGS. 13 to 16, a ridge line at which the fourth blade surface 36B and the fourth cutting blade surface 36C intersect with each other extends toward the intermediate region 22 from the second distal end line 32b of intersection.

A line of intersection (third outer line 35Bb of intersection) at which the third blade surface 35B and the outer peripheral surface 32e intersect with each other is a third outer edge 35Bb including an edge in the circumferential direction of the tubular portion 30. As shown in FIGS. 16 and 17, an angle θ5 formed between the third blade surface 35B and the outer peripheral surface 32e at the third outer edge 35Bb is an acute angle in the distal end region Z1 and the intermediate region Z2.

The line of intersection (third inner line 35Bc of intersection) at which the third blade surface 35B and the inner peripheral surface 32i intersect with each other is a third inner edge 35Bc including an edge in the circumferential direction of the tubular portion 30. As shown in FIGS. 16 and 17, an angle θ6 formed between the third blade surface 35B and the inner peripheral surface 32i at the third inner edge 35Bc is an obtuse angle in the distal end region Z1 and the intermediate region Z2.

A line of intersection (fourth outer line 36Bb of intersection) at which the fourth blade surface 36B and the outer peripheral surface 32e intersect with each other is a fourth outer edge 36Bb including an edge in the circumferential direction of the tubular portion 30. As shown in FIGS. 16 and 17, an angle θ7 formed between the fourth blade surface 36B and the outer peripheral surface 32e at the fourth outer edge 36Bb is an acute angle in the distal end region Z1 and the intermediate region Z2.

The line of intersection (fourth inner line 36Bc of intersection) at which the fourth blade surface 36B and the inner peripheral surface 32i intersect with each other is a fourth inner edge 36Bc including an edge in the circumferential direction of the tubular portion 30. As shown in FIGS. 16 and 17, an angle θ8 formed between the fourth blade surface 36B and the inner peripheral surface 32i at the fourth inner edge 36Bc is an obtuse angle in the distal end region 21 and the intermediate region Z2.

According to the biopsy system 150B including the puncture needle 1B according to this embodiment, punctureability into body tissue is high (the puncture needle 1B easily cuts into the body tissue) and it is easy to collect the cut-out body tissue (a sample required for diagnosis) into the puncture needle 1B. The normal vector 33Bn of the first blade surface 33B and the normal vector 34Bn of the second blade surface 34B in the distal end region Z1 are directed to the third blade surface 35B and the fourth blade surface 36B in the distal end region Z1, respectively, as compared to a direction that is orthogonal to the straight line V passing through the first needle tip 31a and the second needle tip 32a. Further, in the front view, the normal vector 35Bn of the third blade surface 35B and the normal vector 36Bn of the fourth blade surface 36B in the distal end region Z1 are directed to the first blade surface 33B and the second blade surface 34B in the distal end region Z1 as compared to a direction that is orthogonal to the straight line V passing through the first needle tip 31a and the second needle tip 32a. For this reason, the puncture needle 1B can allow the cut-out target tissue T to be suitably moved into the needle tube 3B.

Further, the first outer edge 33Bb, the second outer edge 34Bb, the third outer edge 35Bb, and the fourth outer edge 36Bb of the puncture needle 1B have acute angles in the distal end region Z1 and the intermediate region Z2, and more target tissue T can be cut out in a case where the operator further advances the needle slider 23 to the distal end side of the operation unit 8.

An embodiment of the present disclosure has been described in detail above with reference to the drawings, but specific configuration is not limited to this embodiment and also includes design changes and the like without departing from the scope of the present disclosure. Further, components shown in the above-mentioned embodiment and a modification example can be appropriately combined.

A biopsy system 150E including an endoscope puncture needle 1E according to another exemplary embodiment of the present disclosure will be described with reference to FIGS. 18 to 22. In the following description, components common to the already described components will be denoted by the same reference numerals and the repeated description thereof will be omitted. The endoscope puncture needle 1E further includes a fifth blade surface 41 and a sixth blade surface 42 as compared to the endoscope puncture needle 1 according to the embodiment described above with respect to FIGS. 1-10.

[Biopsy System 150E]

The biopsy system 150E is medical equipment that is used to collect tissue in a body during a biopsy. The biopsy system 150E includes an ultrasound endoscope 100 and an endoscope puncture needle 1E (hereinafter, simply referred to as a "puncture needle 1E".). The puncture needle 1E includes an insertion body 2E, an operation unit 8, and a stylet 27.

[Insertion Body 2E]

The insertion body 2E is an elongated member that can be inserted into a channel 107 of the ultrasound endoscope 100. The insertion body 2E includes a needle tube 3E and a sheath 7.

Figure 18:
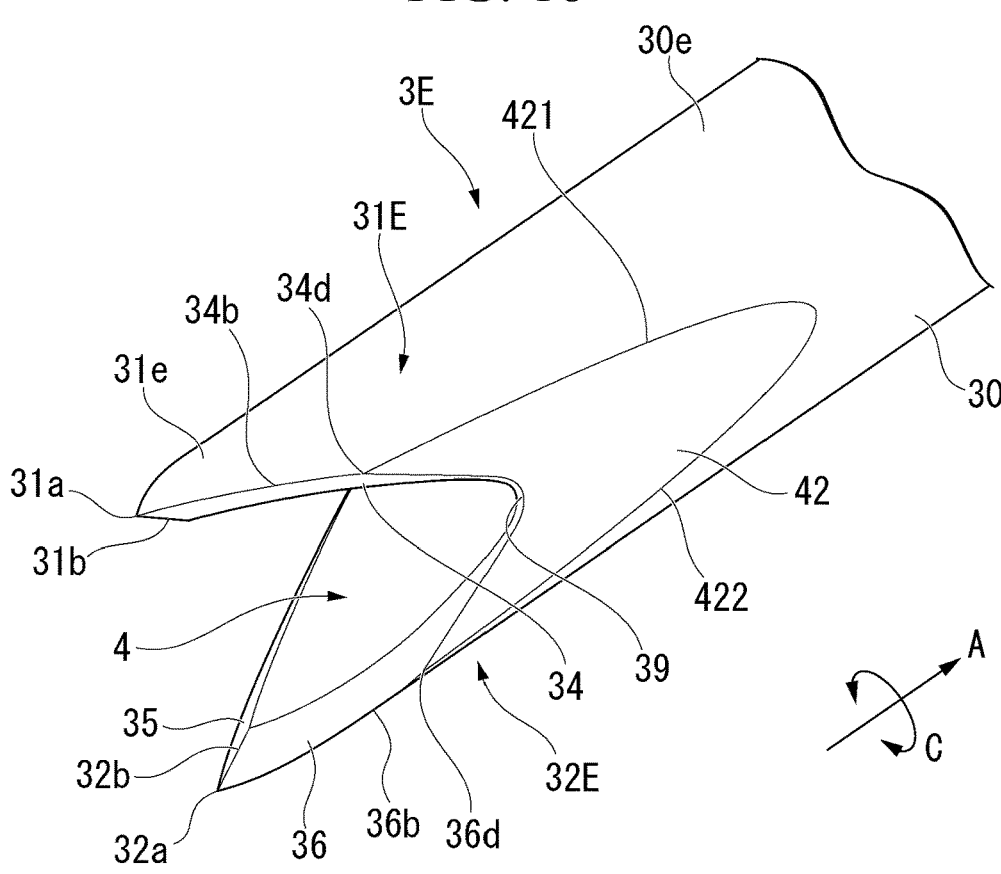
FIG. 18 is a perspective view of a needle tube included in an endoscope puncture needle according to an exemplary embodiment.
Figure 19:
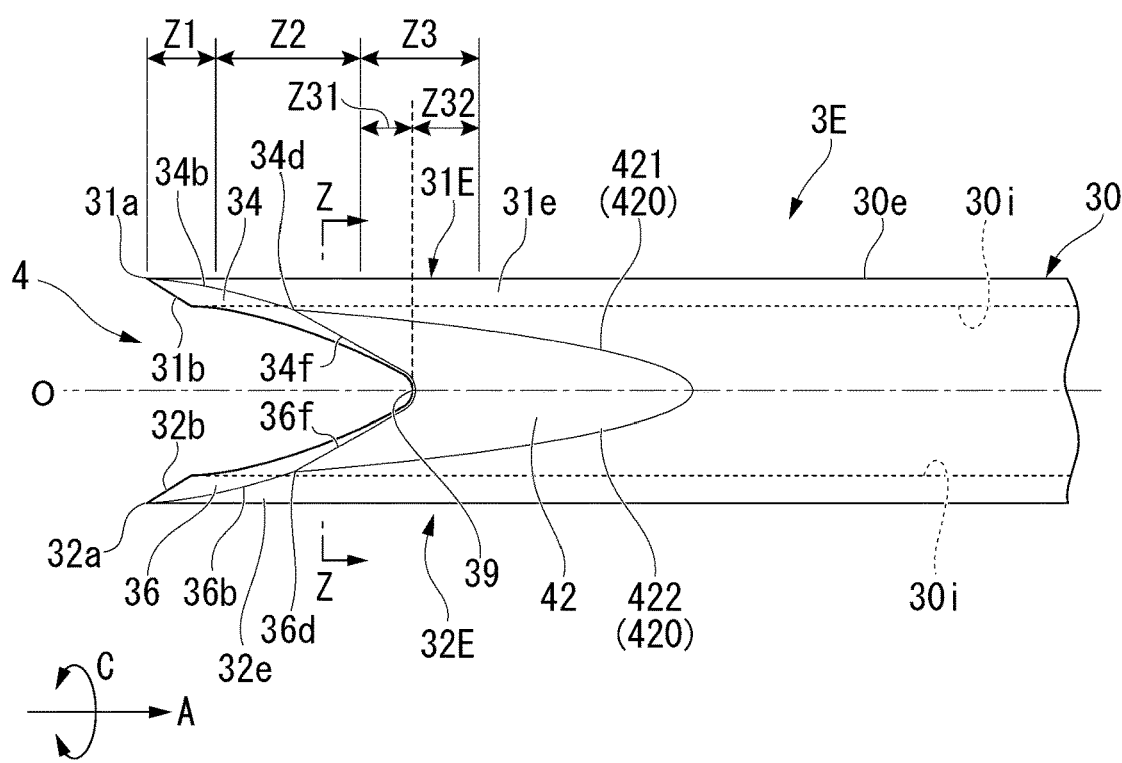
FIG. 19 is a side view of the needle tube.
Figures 20, 21:
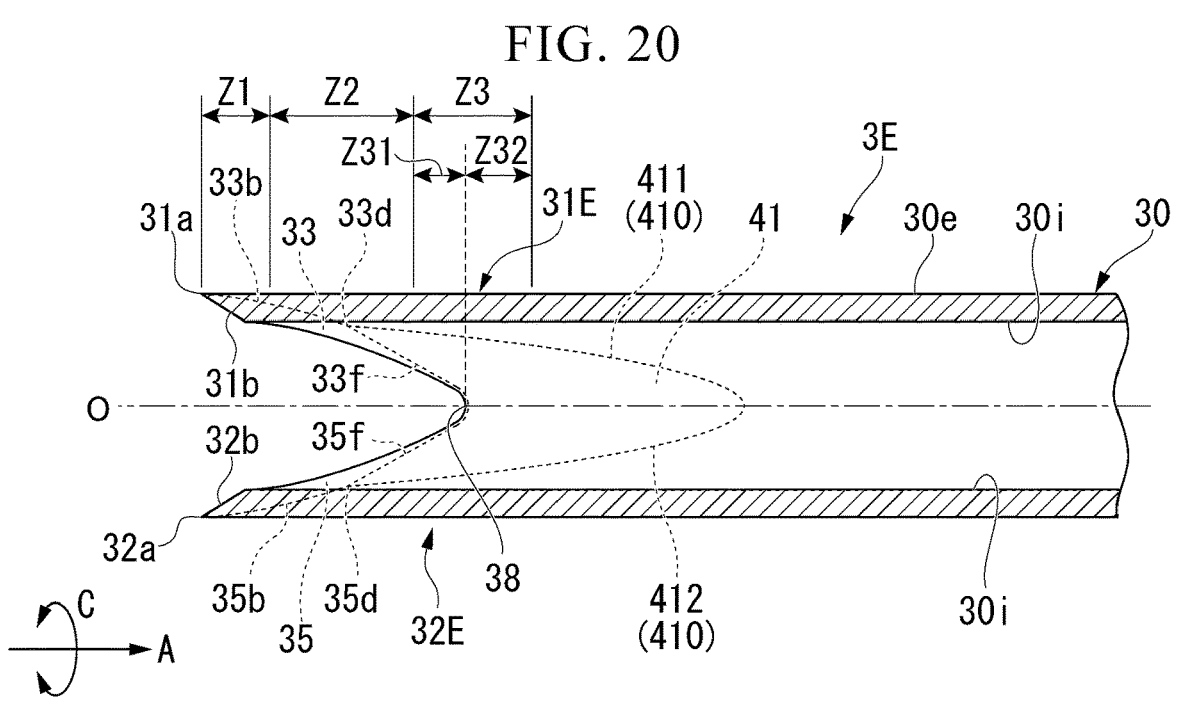
FIG. 20 is a cross-sectional view taken along a central axis of the needle tube and seen in the same direction as FIG. 19.
FIG. 21 is a front view of the needle tube seen from a distal end in an axial direction, and is a diagram in which cross sections are arranged at regular intervals in the direction of a longitudinal axis and which schematically shows a change in the orientation of the cross section of each blade surface.
Figures 22, 23:
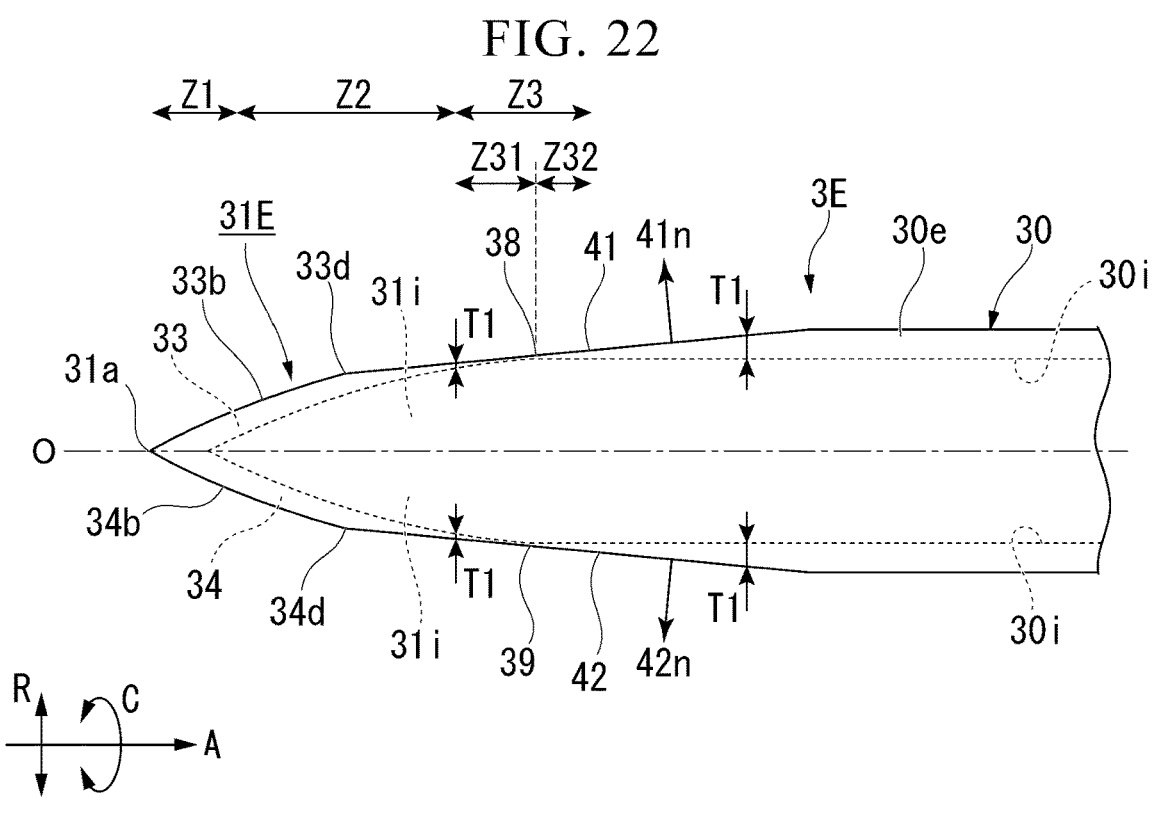
FIG. 22 is a plan view seen in a direction that is a radial direction of the needle tube and is horizontal with respect to a straight line V.
FIG. 23 is a cross-sectional view taken along a central axis and seen in the same direction as FIG. 22.
Figure 24:
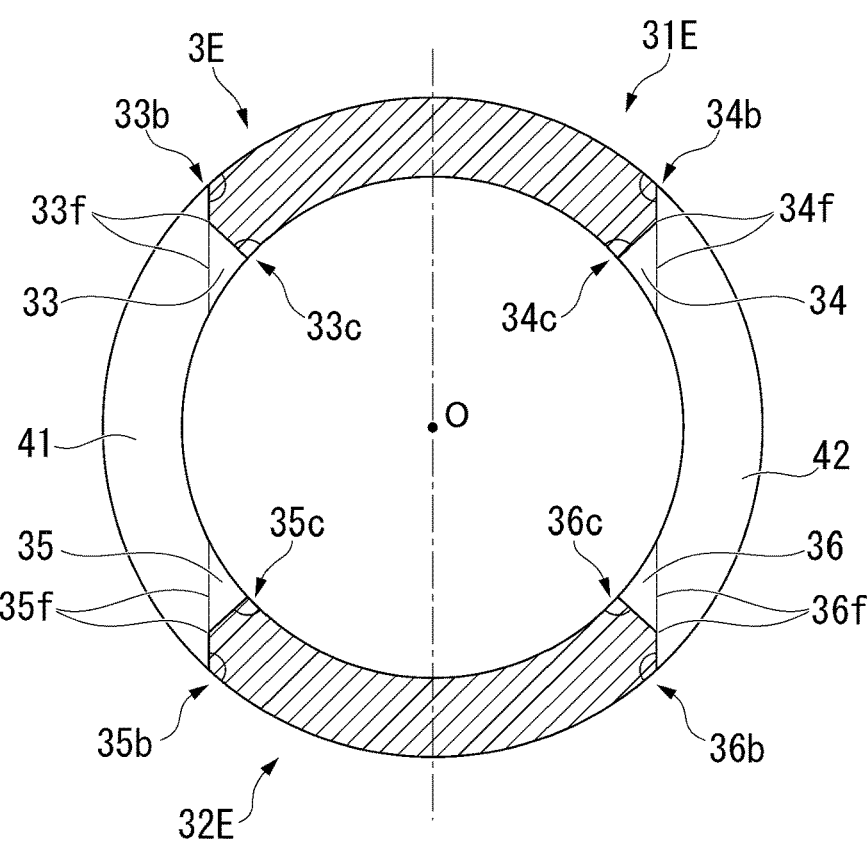
FIG. 24 is a cross-sectional view of the needle tube in a cross section taken along line Z-Z shown in FIG. 19.

FIG. 18 is a perspective view of the needle tube 3E. FIG. 19 is a side view of the needle tube 3E. FIG. 20 is a cross-sectional view taken along a central axis O of the needle tube 3E and seen in the same direction as FIG. 19. FIG. 21 is a front view of the needle tube 3E seen from a distal end in an axial direction A, and is a diagram in which cross sections are arranged at regular intervals in the direction of a longitudinal axis and which schematically shows a change in the orientation of the cross section of each blade surface. A one-dot chain line shown in FIG. 21 indicates a line of intersection between cross sections, which are arranged at regular intervals in the axial direction A and are perpendicular to the axial direction A, and a first blade surface 33, a second blade surface 34, a third blade surface 35, a fourth blade surface 36, a fifth blade surface 41, and a sixth blade surface 42. FIG. 22 is a plan view seen in a direction that is a radial direction R of the needle tube 3E and is horizontal with respect to a straight line V. FIG. 23 is a cross-sectional view taken along the central axis O and seen in the same direction as FIG. 22. FIG. 24 is a cross-sectional view of the needle tube 3E in a cross section taken along line Z-Z shown in FIG. 19.

As shown in FIG. 18, the needle tube 3E includes a tubular portion 30 having a tubular shape, and a first needle tip portion 31E and a second needle tip portion 32E provided at the distal end of the tubular portion 30. The needle tube 3E can be operated to advance and retreat in the sheath 7 by the operation unit 8. An opening 4, which serves as an entrance through which tissue punctured by the first needle tip portion 31E and the second needle tip portion 32E enters the inside of the needle tube 3E, is formed at the distal end of the needle tube 3E. The first needle tip portion 31E and the second needle tip portion 32E of the needle tube 3E can protrude and retract from an opening formed at the distal end portion of the sheath 7.

As shown in FIGS. 18 to 22, the first needle tip portion 31E includes the first blade surface 33 and the second blade surface 34 and the first blade surface 33 and the second blade surface 34 extend toward a sharp first needle tip 31a.

An outer peripheral surface 31e of the first needle tip portion 31E is a curved surface continuous with an outer peripheral surface 30e of the tubular portion 30, and has the same diameter and curvature as the outer peripheral surface 30e. Further, an inner peripheral surface 31i of the first needle tip portion 31E is a curved surface continuous with an inner peripheral surface 30i of the tubular portion 30, and has the same diameter and curvature as the inner peripheral surface 30i. For example, a part of the tubular portion 30 is cut off, so that the first blade surface 33 and the second blade surface 34 of the first needle tip portion 31E are formed.

As shown in FIGS. 18 to 21 and FIG. 23, the second needle tip portion 32E includes the third blade surface 35 and the fourth blade surface 36 and the third blade surface 35 and the fourth blade surface 36 extend toward a sharp second needle tip 32a. The first needle tip 31a and the second needle tip 32a are disposed at positions symmetric with respect to the central axis O extending in the axial direction A of the needle tube 3E.

An outer peripheral surface 32e of the second needle tip portion 32E is a curved surface continuous with the outer peripheral surface 30e of the tubular portion 30, and has the same diameter and curvature as the outer peripheral surface 30e. Further, an inner peripheral surface 32i of the second needle tip portion 32E is a curved surface continuous with the inner peripheral surface 30i of the tubular portion 30, and has the same diameter and curvature as the inner peripheral surface 30i. For example, a part of the tubular portion 30 is cut off, so that the third blade surface 35 and the fourth blade surface 36 of the second needle tip portion 32E are formed.

As shown in FIGS. 18 to 23, the first needle tip portion 31E and the second needle tip portion 32E form the edge of the opening 4 that is surrounded by the first blade surface 33, the second blade surface 34, the third blade surface 35, and the fourth blade surface 36. The opening 4 communicates with the internal space of the tubular portion 30 having a tubular shape.

As shown in FIGS. 18 to 23, the first blade surface 33 and the third blade surface 35 are connected to each other at a first proximal end 38 of the edge of the opening 4. The second blade surface 34 and the fourth blade surface 36 are connected to each other at a second proximal end 39 of the edge of the opening 4.

As shown in FIG. 19, a distal end region Z1 that includes the first needle tip 31a and the second needle tip 32a, a proximal end region Z3 that includes the first proximal end 38 and the second proximal end 39, and an intermediate region Z2 that is positioned between the distal end region Z1 and the proximal end region Z3 and is connected to the distal end region Z1 and the proximal end region z3 are defined at the first needle tip portion 31E and the second needle tip portion 32E. Further, a region of the proximal end region Z3, which is positioned closer to the distal end side than the first proximal end 38 and the second proximal end 39 in the axial direction A, is defined as a first proximal end region Z31 and a region of the proximal end region Z3, which is positioned closer to the proximal end side than the first proximal end 38 and the second proximal end 39 in the axial direction A, is defined as a second proximal end region Z32.

The first needle tip portion 31E and the second needle tip portion 32E include a fifth blade surface 41 and a sixth blade surface 42 on the outer peripheral surface 31e of the first needle tip portion 31E and the outer peripheral surface 32e of the second needle tip portion 32E.

(Fifth Blade Surface 41 and Sixth Blade Surface 42)

The fifth blade surface 41 is a blade surface that is formed on the outer peripheral surface 31e of the first needle tip portion 31E and the outer peripheral surface 32e of the second needle tip portion 32E. As shown in FIGS. 22 and 23, the fifth blade surface 41 is an inclined surface inclined with respect to the central axis O, and a distance between the fifth blade surface 41 and the central axis O is gradually reduced toward the first needle tip 31a and the second needle tip 32a from the proximal end side of the needle tube 3E. The fifth blade surface 41 includes a first outer intersection 33d (see FIG. 22) that is an intersection between the fifth blade surface 41 and a first outer line 33b of intersection (first outer edge), and a third outer intersection 35d (see FIG. 23) that is an intersection between the fifth blade surface 41 and a third outer line 35b of intersection (third outer edge). As shown in FIGS. 20 and 22, the first outer line 33b of intersection is a line of intersection that is formed by the first blade surface 33 and the outer peripheral surface 31e of the first needle tip portion 31E. As shown in FIGS. 20 and 23, the third outer line 35b of intersection is a line of intersection that is formed by the third blade surface 35 and the outer peripheral surface 32e of the second needle tip portion 32E. The fifth blade surface 41 and the first outer line 33b of intersection intersect with each other at the first outer intersection 33d, and the fifth blade surface 41 and the third outer line 35b of intersection intersect with each other at the third outer intersection 35d.

As shown in FIG. 24, a line of intersection at which the fifth blade surface 41 and the first blade surface 33 intersect with each other is defined as a first intermediate edge 33f. A line of intersection at which the fifth blade surface 41 and the third blade surface 35 intersect with each other is defined as a third intermediate edge 35f. As shown in FIG. 20, the first intermediate edge 33f and the third intermediate edge 35f are connected to each other at the first proximal end 38.

As shown in FIGS. 21 to 23, in the first proximal end region Z31, a thickness T1 between the fifth blade surface 41 and the inner peripheral surface 31i of the first needle tip portion 31E is reduced toward the first proximal end 38 from the first outer intersection 33d. Further, in the first proximal end region Z31, a thickness T1 between the fifth blade surface 41 and the inner peripheral surface 32l of the second needle tip portion 32E is reduced toward the first proximal end 38 from the third outer intersection 35d.

As shown in FIGS. 21 to 23, in the second proximal end region Z32, the thickness T1 between the fifth blade surface 41 and the inner peripheral surface 31i of the first needle tip portion 31E is increased toward the proximal end side of the needle tube 3E from the first proximal end 38. Likewise, in the second proximal end region Z32, the thickness T1 between the fifth blade surface 41 and the inner peripheral surface 32i of the second needle tip portion 32E is increased toward the proximal end side of the needle tube 3E from the first proximal end 38. That is, the thicknesses T1 between the fifth blade surface 41 and the inner peripheral surfaces 31i and 32i are reduced toward the first proximal end 38 from the proximal end of the fifth blade surface 41.

As shown in FIG. 20, in a side view seen in a direction orthogonal to the central axis O and the straight line V, the first outer intersection 33d and the third outer intersection 35d of the fifth blade surface 41 are formed at positions symmetric with respect to the central axis O extending in the axial direction A of the needle tube 3E. As shown in FIGS. 22 and 23, the first outer intersection 33d and the third outer intersection 35d are positioned at the distal end of the fifth blade surface 41.

A line of intersection, which is formed by the fifth blade surface 41 and the outer peripheral surface 31e of the first needle tip portion 31E, is defined as a fifth line 410 of intersection. As shown in FIG. 20, an interval between a first portion 411, which is connected to the first outer intersection 33d, and a third portion 412, which is connected to the third outer intersection 35d, of the fifth line 410 of intersection is gradually reduced toward the proximal end of the fifth blade surface 41 from the distal end of the fifth blade surface 41.

As shown in FIG. 23, a first proximal end edge 38e of which the distal end is the first proximal end 38 is formed in the second proximal end region Z32. The first proximal end edge 38e is a sharp blade that is formed by the fifth blade surface 41 and the inner peripheral surfaces 31i and 32i. The thickness T1 at the first proximal end 38 is set to be small, so that a resistance force, which is applied to the first proximal end 38 from tissue in a case where the body tissue is punctured by the needle tube 3E, can be reduced. Further, distal end angles formed between the fifth blade surface 41 and the inner peripheral surfaces 31i and 32i are set to be small at the first proximal end 38, so that the first proximal end edge 38e is formed.

The sixth blade surface 42 is a blade surface that is formed on the outer peripheral surface 31e of the first needle tip portion 31E and the outer peripheral surface 32e of the second needle tip portion 32E. As shown in FIGS. 22 and 23, the sixth blade surface 42 is an inclined surface inclined with respect to the central axis O, and a distance between the sixth blade surface 42 and the central axis O is gradually reduced toward the first needle tip 31a and the second needle tip 32a from the proximal end side of the needle tube 3E. The sixth blade surface 42 includes a second outer intersection 34d (see FIG. 22) that is an intersection between the sixth blade surface 42 and a second outer line 34b of intersection (second outer edge), and a fourth outer intersection 36d (see FIG. 23) that is an intersection between the sixth blade surface 42 and a fourth outer line 36b of intersection (fourth outer edge). As shown in FIGS. 19 and 22, the second outer line 34b of intersection is a line of intersection that is formed by the second blade surface 34 and the outer peripheral surface 31e of the first needle tip portion 31E. As shown in FIGS. 19 and 23, the fourth outer line 36b of intersection is a line of intersection that is formed by the fourth blade surface 36 and the outer peripheral surface 32e of the second needle tip portion 32E. The sixth blade surface 42 and the second outer line 34b of intersection intersect with each other at the second outer intersection 34d, and the sixth blade surface 42 and the fourth outer line 36b of intersection intersect with each other at the fourth outer intersection 36d.

As shown in FIG. 24, a line of intersection at which the sixth blade surface 42 and the first blade surface 33 intersect with each other is defined as a second intermediate edge 34f. A line of intersection at which the sixth blade surface 42 and the fourth blade surface 36 intersect with each other is defined as a fourth intermediate edge 36f. As shown in FIG. 19, the second intermediate edge 34f and the fourth intermediate edge 36f are connected to each other at the second proximal end 39.

As shown in FIGS. 21 to 23, in the first proximal end region Z31, a thickness T1 between the sixth blade surface 42 and the inner peripheral surface 31i of the first needle tip portion 31E is reduced toward the second proximal end 39 from the second outer intersection 34d. Likewise, in the first proximal end region Z31, the thickness T1 is reduced toward the second proximal end 39 from the fourth outer intersection 36d.

As shown in FIGS. 21 to 23, in the second proximal end region Z32, the thickness T1 between the sixth blade surface 42 and the inner peripheral surface 31*i* of the first needle tip portion 31E is increased toward the proximal end side from the second proximal end 39. Likewise, in the second proximal end region Z32, a thickness T1 between the sixth blade surface 42 and the inner peripheral surface 32*i* of the second needle tip portion 32E is increased toward the proximal end side from the second proximal end 39. That is, the thicknesses T1 between the sixth blade surface 42 and the inner peripheral surfaces 31*i* and 32*i* are reduced toward the second proximal end 39 from the proximal end of the sixth blade surface 42.

As shown in FIG. 19, in a side view seen in a direction orthogonal to the central axis O and the straight line V, the second outer intersection 34*d* and the fourth outer intersection 36*d* of the sixth blade surface 42 are formed at positions symmetric with respect to the central axis O extending in the axial direction A of the needle tube 3E. As shown in FIGS. 22 and 23, the first outer intersection 33*d* and the third outer intersection 35*d* are positioned at the distal end of the sixth blade surface 42.

A line of intersection, which is formed by the sixth blade surface 42 and the outer peripheral surface 31*e* of the first needle tip portion 31E, is defined as a sixth line 420 of intersection. As shown in FIG. 19, an interval between a second portion 421, which is connected to the second outer intersection 34*d*, and a fourth portion 422, which is connected to the fourth outer intersection 36*d*, of the sixth line of intersection is gradually reduced toward the proximal end of the sixth blade surface 42 from the distal end of the sixth blade surface 42.

As shown in FIG. 23, a second proximal end edge 39*e* of which the distal end is the second proximal end 39 is formed in the second proximal end region Z32. The second proximal end edge 39*e* is a sharp blade that is formed by the sixth blade surface 42 and the inner peripheral surfaces 31*i* and 32*l*. Since the thickness T1 at the second proximal end 39 is to be small, a resistance force, which is applied to the second proximal end 39 from tissue in a case where the body tissue is punctured by the needle tube 3E, can be reduced. Further, distal end angles formed between the sixth blade surface 42 and the inner peripheral surfaces 31*i* and 32*i* are set to be small at the second proximal end 39, so that the second proximal end edge 39*e* is formed.

For example, the outer peripheral surface 30*e* of the tubular portion 30 of the needle tube 3E is cut, so that the fifth blade surface 41 and the sixth blade surface 42 are formed. It is desired that the first outer intersection 33*d* and the second outer intersection 34*d* are formed at positions symmetric with respect to the straight line V passing through the first needle tip 31*a* and the second needle tip 32*a* as shown in FIG. 21 in a front view seen in a direction along the axial direction A of the needle tube 3E (tubular portion 30). Likewise, it is desired that the third outer intersection 35*d* and the fourth outer intersection 36*d* are formed at positions symmetric with respect to the straight line V passing through the first needle tip 31*a* and the second needle tip 32*a* in the front view. The fifth blade surface 41 and the sixth blade surface 42 are not limited to the flat surfaces, and may be formed in curved surfaces.

According to the biopsy system 150E including the puncture needle 1E according to this embodiment, not only the first outer edge 33*b*, the second outer edge 34*b*, the third outer edge 35*b*, and the fourth outer edge 36*b* but also the first proximal end edge 38*e* and the second proximal end edge 39*e* cut into body tissue. Accordingly, it is easy to collect the body tissue (a sample required for diagnosis).

According to the biopsy system 150E including the puncture needle 1E according to this embodiment, punctureability into body tissue is high (the puncture needle 1E easily cuts into the body tissue) and it is easy to collect the cut-out body tissue (a sample required for diagnosis) into the puncture needle 1E. Since the first proximal end 38 and the second proximal end 39 of the needle tube 3E are thinner and sharper than those of the needle tube 3 of the embodiment described above with respect to FIGS. 1-10, the needle tube 3E has higher punctureability in addition to collectability.

An embodiment of the present disclosure has been described in detail above with reference to the drawings, but specific configuration is not limited to this embodiment and also includes design changes and the like without departing from the scope of the present disclosure. Further, components shown in the above-mentioned embodiment and a modification example can be appropriately combined.

Figure 25:
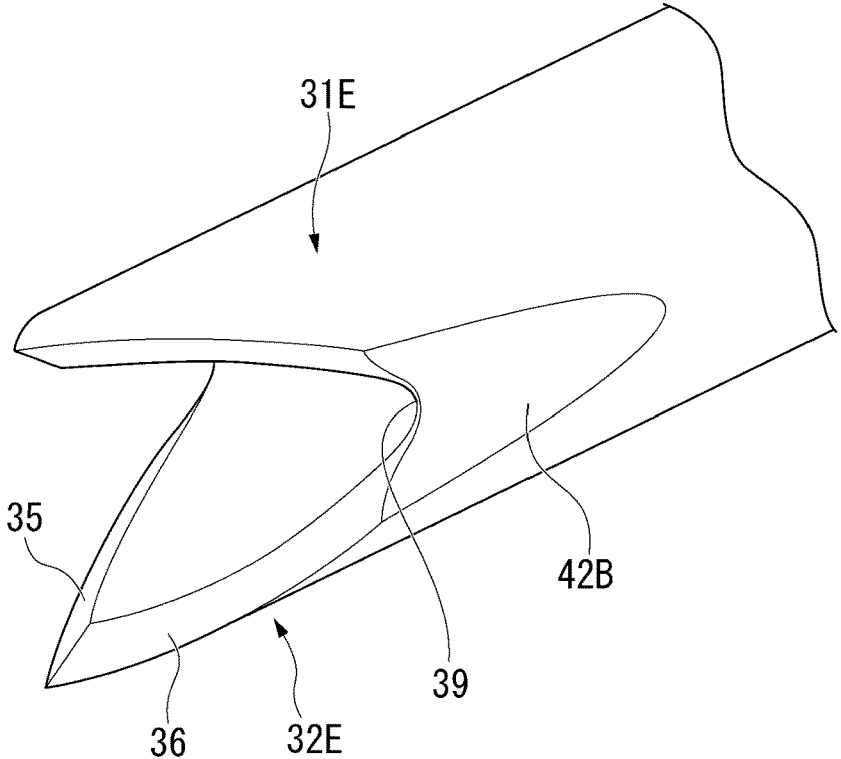
FIG. 25 is a perspective view showing a modification example of a sixth blade surface of the needle tube.

The fifth blade surface 41 and the sixth blade surface 42 are formed of flat surfaces in the embodiment, but the fifth blade surface 41 and the sixth blade surface 42 are not limited thereto. FIG. 25 is a perspective view showing a sixth blade surface 42B that is a modification example of the sixth blade surface 42. The sixth blade surface 42B is worked into a curved surface by an end mill. In a case where the sixth blade surface 42B is provided as in the embodiment, a second proximal end edge 39*e* of which the distal end is the second proximal end 39 is formed. Further, a thickness T1 between the sixth blade surface 42B and the inner peripheral surface 31*i* of the first needle tip portion 31E is increased toward the proximal end side from the second proximal end 39. The same applies to the fifth blade surface 41.

A biopsy system 150F including an endoscope puncture needle 1F according to another exemplary embodiment of the present disclosure will be described with reference to FIGS. 26 to 35. In the following description, components common to the already described components will be denoted by the same reference numerals and the repeated description thereof will be omitted. The endoscope puncture needle 1F further includes a seventh blade surface 43 and an eighth blade surface 44 as compared to the endoscope puncture needle 1 according to the embodiment described above with respect to FIGS. 1-10.

[Biopsy System 150F]

The biopsy system 150F is medical equipment that is used to collect tissue in a body during a biopsy. The biopsy system 150F includes an ultrasound endoscope 100 and an endoscope puncture needle 1F (hereinafter, simply referred to as a "puncture needle 1F".). The puncture needle 1F includes an insertion body 2F, an operation unit 8, and a stylet 27.

[Insertion Body 2F]

The insertion body 2F is an elongated member that can be inserted into a channel 107 of the ultrasound endoscope 100. The insertion body 2F includes a needle tube 3F and a sheath 7.

Figure 26:
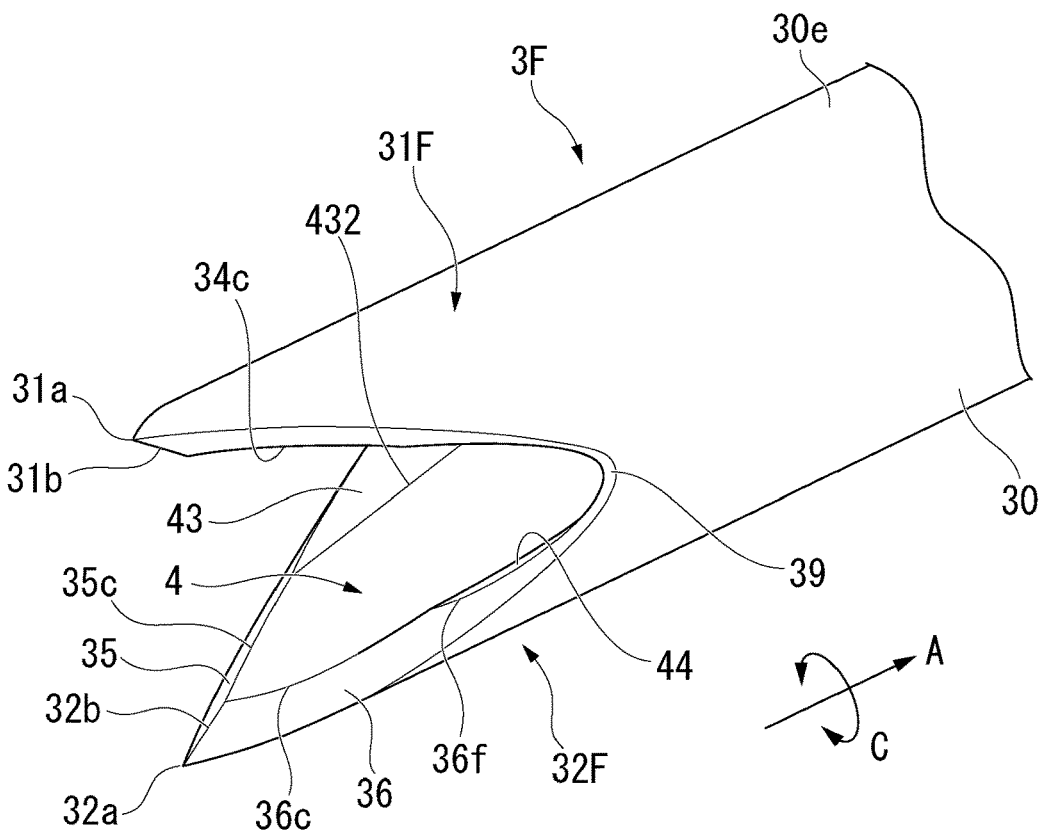
FIG. 26 is a perspective view of a needle tube included in an endoscope puncture needle according to an exemplary embodiment.
Figure 27:
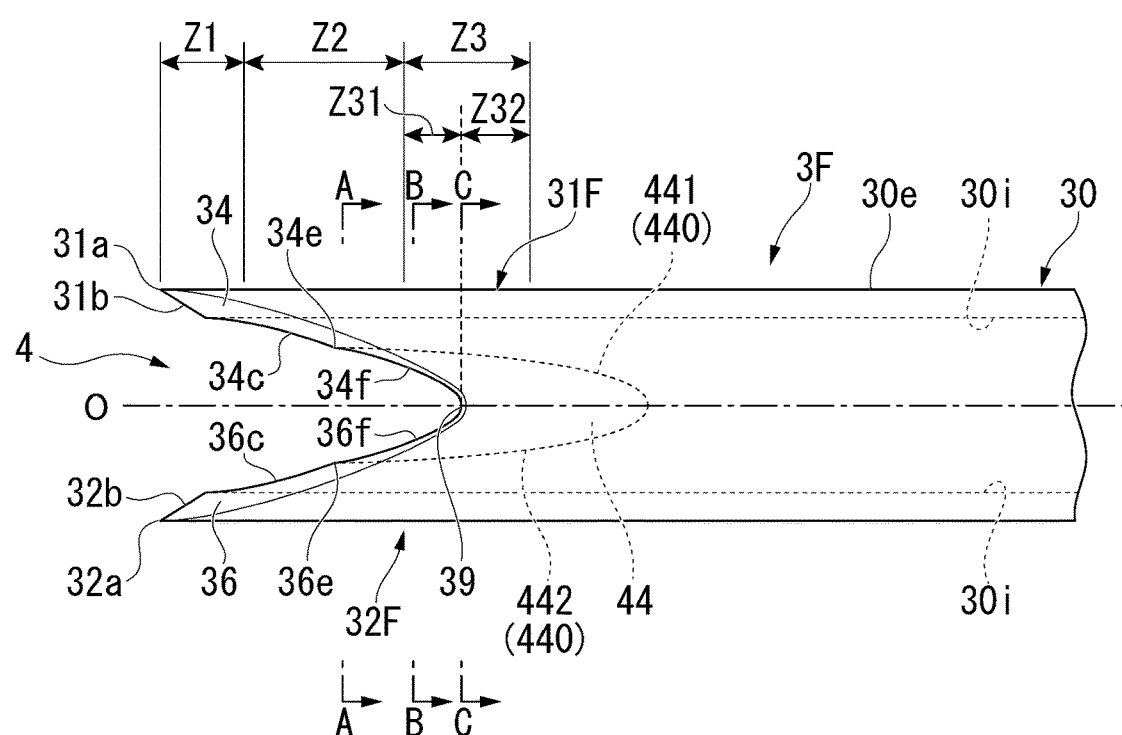
FIG. 27 is a side view of the needle tube.
Figure 28:
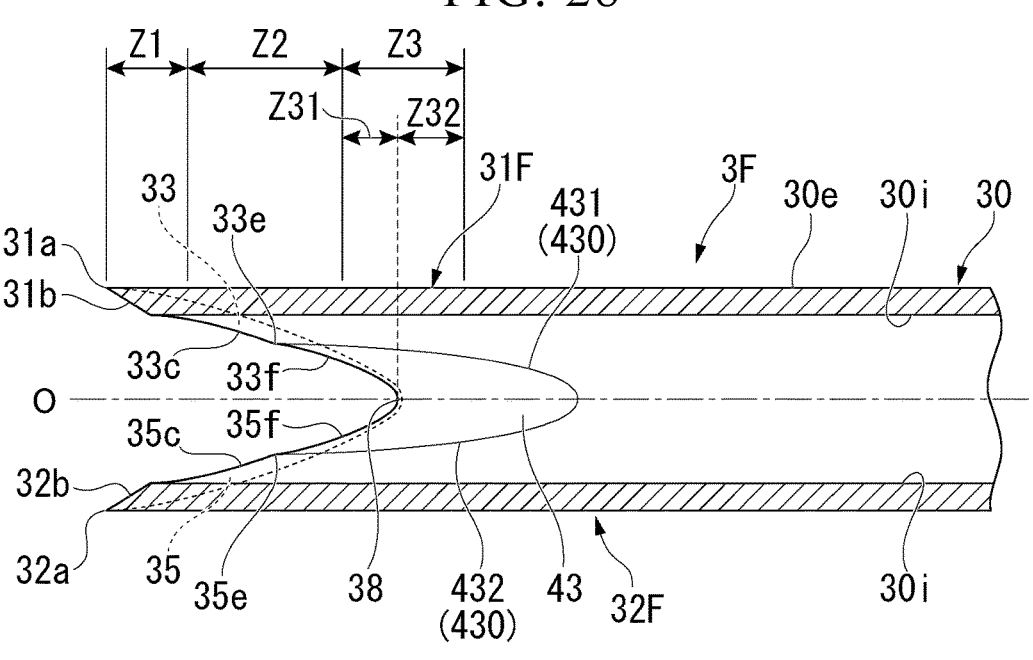
FIG. 28 is a cross-sectional view taken along a central axis of the needle tube and seen in the same direction as FIG. 27.
Figure 29:
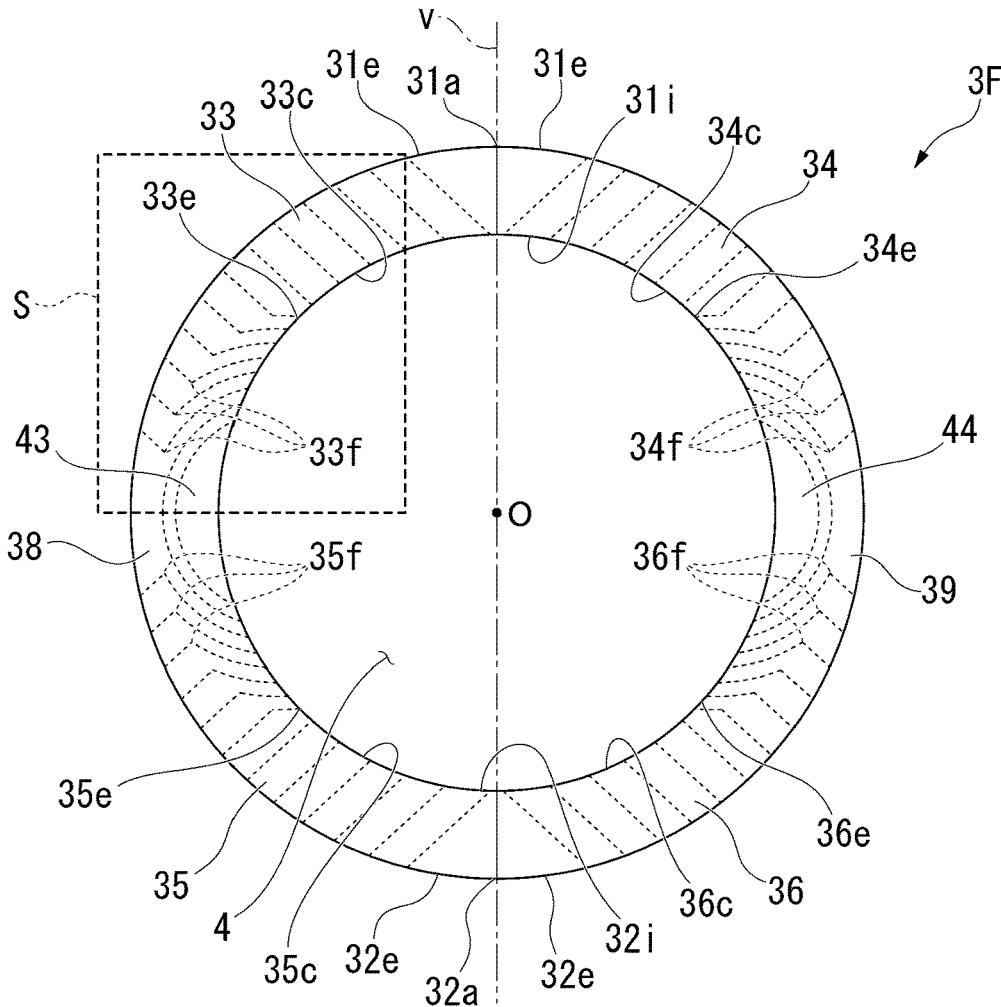
FIG. 29 is a front view of the needle tube seen from a distal end in an axial direction, and is a diagram in which cross sections are arranged at regular intervals in the direction of a longitudinal axis and which schematically shows a change in the orientation of the cross section of each blade surface.
Figure 30:
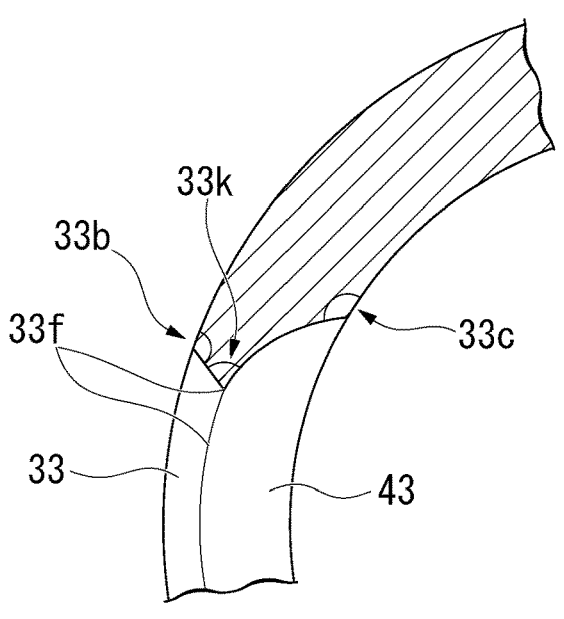
FIG. 30 is a cross-sectional view taken along line B-B of the needle tube shown in FIG. 27 and is an enlarged cross-sectional view of a region S shown in FIG. 29.
Figure 31:
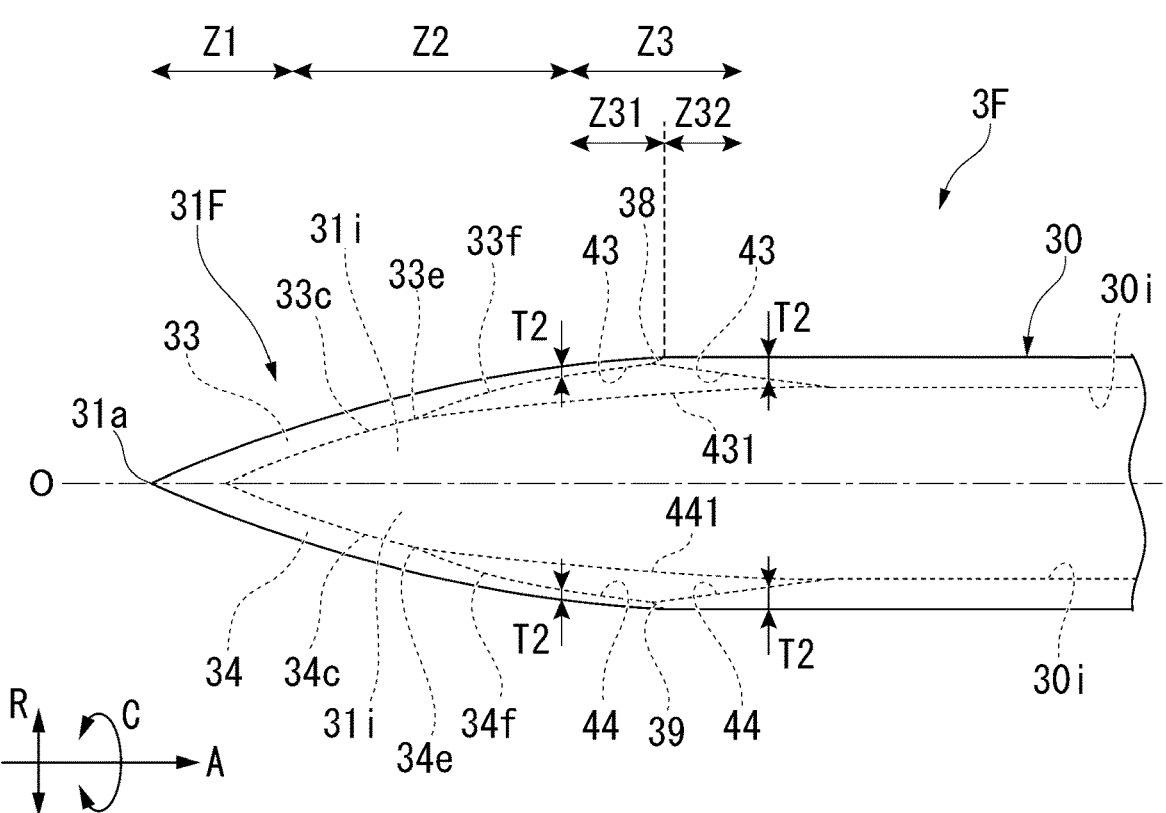
FIG. 31 is a plan view seen in a direction that is a radial direction of the needle tube and is horizontal with respect to a straight line V.
Figures 32, 33:
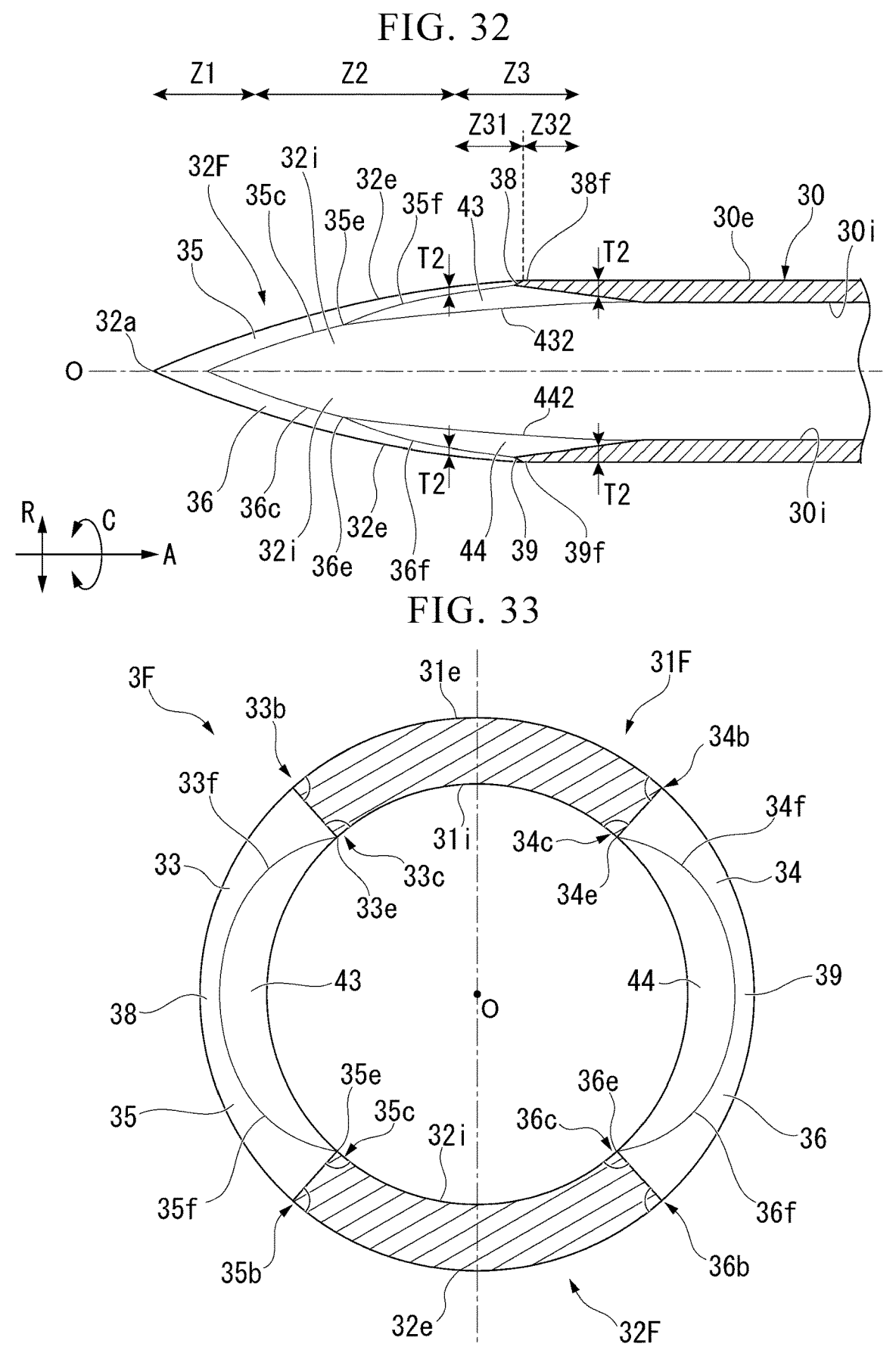

FIG. 26 is a perspective view of the needle tube 3F. FIG. 27 is a side view of the needle tube 3F. FIG. 28 is a cross-sectional view taken along a central axis O of the needle tube 3F and seen in the same direction as FIG. 27. FIG. 29 is a front view of the needle tube 3F seen from a distal end in an axial direction A, and is a diagram in which cross sections are arranged at regular intervals in the direction of a longitudinal axis and which schematically shows a change in the orientation of the cross section of each blade surface. A one-dot chain line shown in FIG. 29 indicates a line of intersection between cross sections, which are arranged at regular intervals in the axial direction A and are perpendicular to the axial direction A, and a first blade surface 33, a second blade surface 34, a third blade surface 35, a fourth blade surface 36, a seventh blade surface 43, and an eighth blade surface 44. FIG. 30 is a cross-sectional view taken along line B-B of the needle tube 3F shown in FIG. 27 and is an enlarged cross-sectional view of a region S shown in FIG. 29. FIG. 31 is a plan view seen in a direction that is a radial direction R of the needle tube 3F and is horizontal with respect to a straight line V. FIG. 32 is a cross-sectional view taken along the central axis O and seen in the same direction as FIG. 31.

Figure 34:
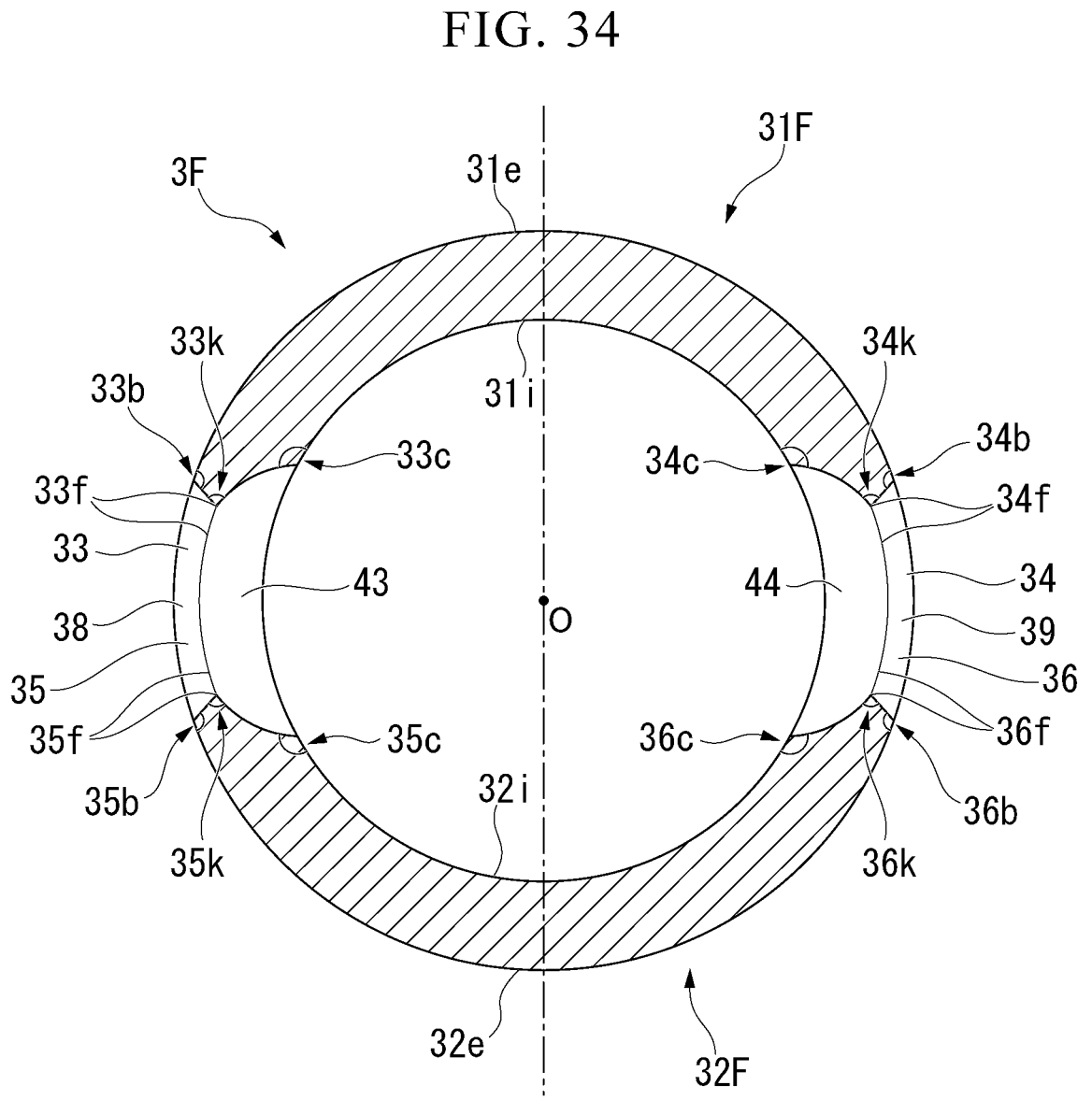
Figure 35:
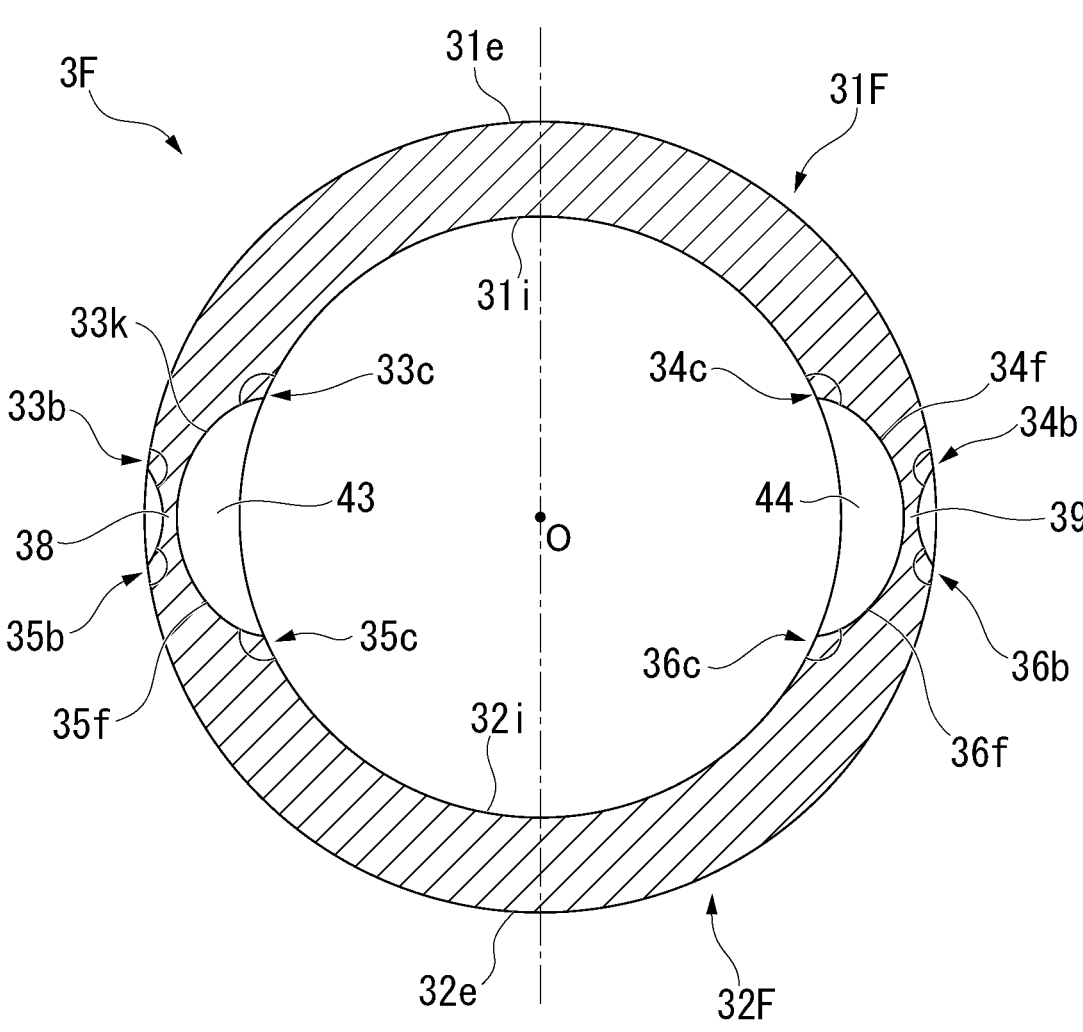
FIG. 35 is a cross-sectional view taken along line C-C of the needle tube shown in FIG. 27.

FIG. 33 is a cross-sectional view taken along line A-A of the needle tube 3F shown in FIG. 27. FIG. 34 is a cross-sectional view taken along line B-B of the needle tube 3F shown in FIG. 27. FIG. 35 is a cross-sectional view taken along line C-C of the needle tube 3F shown in FIG. 27. Line A-A passes through a first inner intersection 33e, a second inner intersection 34e, a third inner intersection 35e, and a fourth inner intersection 36e to be described later. Line C-C passes through a first proximal end 38 and a second proximal end 39.

As shown in FIG. 26, the needle tube 3F includes a tubular portion 30 having a tubular shape, and a first needle tip portion 31F and a second needle tip portion 32F provided at the distal end of the tubular portion 30. The needle tube 3F can be operated to advance and retreat in the sheath 7 by the operation unit 8. An opening 4, which serves as an entrance through which tissue punctured by the first needle tip portion 31F and the second needle tip portion 32F enters the inside of the needle tube 3F, is formed at the distal end of the needle tube 3F. The first needle tip portion 31F and the second needle tip portion 32F of the needle tube 3F can protrude and retract from an opening formed at the distal end portion of the sheath 7.

As shown in FIGS. 26 to 31, the first needle tip portion 31F includes the first blade surface 33 and the second blade surface 34 and the first blade surface 33 and the second blade surface 34 extend toward a sharp first needle tip 31a.

An outer peripheral surface 31e of the first needle tip portion 31F is a curved surface continuous with an outer peripheral surface 30e of the tubular portion 30, and has the same diameter and curvature as the outer peripheral surface 30e. Further, an inner peripheral surface 31i of the first needle tip portion 31F is a curved surface continuous with an inner peripheral surface 30i of the tubular portion 30, and has the same diameter and curvature as the inner peripheral surface 30i. For example, a part of the tubular portion 30 is cut off, so that the first blade surface 33 and the second blade surface 34 of the first needle tip portion 31F are formed.

As shown in FIGS. 26 to 29 and FIG. 32, the second needle tip portion 32F includes the third blade surface 35 and the fourth blade surface 36 and the third blade surface 35 and the fourth blade surface 36 extend toward a sharp second needle tip 32a. The first needle tip 31a and the second needle tip 32a are disposed at positions symmetric with respect to the central axis O extending in the axial direction A of the needle tube 3F.

An outer peripheral surface 32e of the second needle tip portion 32F is a curved surface continuous with the outer peripheral surface 30e of the tubular portion 30, and has the same diameter and curvature as the outer peripheral surface 30e. Further, an inner peripheral surface 32l of the second needle tip portion 32F is a curved surface continuous with the inner peripheral surface 30i of the tubular portion 30, and has the same diameter and curvature as the inner peripheral surface 30i. For example, a part of the tubular portion 30 is cut off, so that the third blade surface 35 and the fourth blade surface 36 of the second needle tip portion 32F are formed.

As shown in FIGS. 26 to 32, the first needle tip portion 31F and the second needle tip portion 32F form the edge of the opening 4 that is surrounded by the first blade surface 33, the second blade surface 34, the third blade surface 35, and the fourth blade surface 36. The opening 4 communicates with the internal space of the tubular portion 30 having a tubular shape.

As shown in FIGS. 26 to 32, the first blade surface 33 and the third blade surface 35 are connected to each other at the first proximal end 38 of the edge of the opening 4. The second blade surface 34 and the fourth blade surface 36 are connected to each other at a second proximal end 39 of the edge of the opening 4.

As shown in FIG. 27, a distal end region Z1 that includes the first needle tip 31a and the second needle tip 32a, a proximal end region Z3 that includes the first proximal end 38 and the second proximal end 39, and an intermediate region Z2 that is positioned between the distal end region Z1 and the proximal end region Z3 and is connected to the distal end region Z1 and the proximal end region Z3 are defined at the first needle tip portion 31F and the second needle tip portion 32F. Further, a region of the proximal end region 23, which is positioned closer to the distal end side than the first proximal end 38 and the second proximal end 39 in the axial direction A, is defined as a first proximal end region Z31 and a region of the proximal end region Z3, which is positioned closer to the proximal end side than the first proximal end 38 and the second proximal end 39 in the axial direction A, is defined as a second proximal end region Z32.

The first needle tip portion 31F and the second needle tip portion 32F include a seventh blade surface 43 and an eighth blade surface 44 on the inner peripheral surface 31i of the first needle tip portion 31F and the inner peripheral surface 32l of the second needle tip portion 32F. The first needle tip portion 31F and the second needle tip portion 32F may include the fifth blade surface 41 and the sixth blade surface 42 described in the above embodiment (e.g., described with respect to FIGS. 18-24) in addition to the seventh blade surface 43 and the eighth blade surface 44, or may include the seventh blade surface 43 and the eighth blade surface 44 instead of the fifth blade surface 41 and the sixth blade surface 42 without including the fifth blade surface 41 and the sixth blade surface 42.

(Seventh Blade Surface 43 and Eighth Blade Surface 44)

The seventh blade surface 43 is a blade surface that is formed on the inner peripheral surface 31i of the first needle tip portion 31F and the inner peripheral surface 32l of the second needle tip portion 32F. As shown in FIG. 29, the seventh blade surface 43 includes the first inner intersection 33e (see FIG. 31) that is an intersection between the seventh blade surface 43 and a first inner line 33c of intersection (first inner edge), and the third inner intersection 35e (see FIG. 32) that is an intersection between the seventh blade surface 43 and a third inner line 35c of intersection (third inner edge). As shown in FIGS. 28 and 31, the first inner line 33c of intersection is a line of intersection that is formed by the first blade surface 33 and the inner peripheral surface 31i of the first needle tip portion 31F. As shown in FIGS. 28 and 32, the third inner line 35c of intersection is a line of intersection that is formed by the third blade surface 35 and the inner peripheral surface 32i of the second needle tip portion 32F. The seventh blade surface 43 and the first inner line 33c of intersection intersect with each other at the first inner intersection 33e, and the seventh blade surface 43 and the third inner line 35c of intersection intersect with each other at the third inner intersection 35e.

As shown in FIGS. 33 to 35, a line of intersection at which the seventh blade surface 43 and the first blade surface 33 intersect with each other is defined as a first intermediate edge 33f. A line of intersection at which the seventh blade surface 43 and the third blade surface 35 intersect with each other is defined as a third intermediate edge 35f. The first intermediate edge 33f and the third intermediate edge 35f are connected to each other at the first proximal end 38.

As shown in FIGS. 29 and 30, an angle 33k formed between the seventh blade surface 43 and the first blade surface 33 at the first intermediate edge 33f is reduced toward the proximal end of the needle tube 3F from the distal end of the needle tube 3F.

As shown in FIGS. 29 and 34, an angle 35k formed between the seventh blade surface 43 and the third blade surface 35 at the third intermediate edge 35f is reduced toward the proximal end from the distal end.

As shown in FIG. 29, the curvatures of curves, which are formed by the first intermediate edge 33f and the third intermediate edge 35f, are larger than the curvature of the inner peripheral surface 30i of the tubular portion 30 in a cross section perpendicular to the axial direction A.

As shown in FIGS. 29 to 32, in the first proximal end region Z31, a thickness T2 between the seventh blade surface 43 and the outer peripheral surface 31e of the first needle tip portion 31F is reduced toward the first proximal end 38 from the first inner intersection 33e. Likewise, in the first proximal end region Z31, the thickness T2 is reduced toward the first proximal end 38 from the third inner intersection 35e.

As shown in FIGS. 29 to 32, in the second proximal end region Z32, the thickness T2 between the seventh blade surface 43 and the outer peripheral surface 31e of the first needle tip portion 31F is increased toward the proximal end side of the needle tube 3F from the first proximal end 38. Likewise, in the second proximal end region Z32, a thickness T2 between the seventh blade surface 43 and the outer peripheral surface 32e of the second needle tip portion 32F is increased toward the proximal end side of the needle tube 3F from the first proximal end 38. That is, the thicknesses T1 between the seventh blade surface 43 and the outer peripheral surfaces 31e and 32e are reduced toward the first proximal end 38 from the proximal end of the seventh blade surface.

In a side view seen in a direction orthogonal to the central axis O and the straight line V, the first inner intersection 33e and the third inner intersection 35e are formed at positions symmetric with respect to the central axis O extending in the axial direction A of the needle tube 3F. As shown in FIGS. 31 and 32, the first inner intersection 33e and the third inner intersection 35e are positioned at the distal end of the seventh blade surface 43.

A line of intersection, which is formed by the seventh blade surface 43 and the inner peripheral surface 31i of the first needle tip portion 31F, is defined as a seventh line 430 of intersection. As shown in FIG. 28, an interval between a first portion 431, which is connected to the inner peripheral surface 31i, and a third portion 432, which is connected to the inner peripheral surface 32i, of the seventh line 430 of intersection is gradually reduced toward the proximal end of the seventh blade surface 43 from the distal end of the seventh blade surface 43.

As shown in FIG. 32, a first proximal end edge 38f of which the distal end is the first proximal end 38 is formed in the second proximal end region Z32. The first proximal end edge 38f is a sharp blade that is formed by the seventh blade surface 43 and the outer peripheral surfaces 31e and 32e. The thickness T2 at the first proximal end 38 is set to be small, so that a resistance force, which is applied to the first proximal end 38 from tissue in a case where the body tissue is punctured by the needle tube 3F, can be reduced. Further, distal end angles formed between the seventh blade surface 43 and the outer peripheral surfaces 31e and 32e are set to be small at the first proximal end 38, so that the first proximal end edge 38f is formed.

The eighth blade surface 44 is a blade surface that is formed on the inner peripheral surface 31i of the first needle tip portion 31F and the inner peripheral surface 32i of the second needle tip portion 32E. As shown in FIG. 29, the eighth blade surface 44 includes the second inner intersection 34e (see FIG. 31) that is an intersection between the eighth blade surface 44 and a second inner line 34c of intersection (second inner edge), and the fourth inner intersection 36e (see FIG. 32) that is an intersection between the eighth blade surface 44 and a fourth inner line 36c of intersection (fourth inner edge). As shown in FIGS. 27 and 31, the second inner line 34c of intersection is a line of intersection that is formed by the second blade surface 34 and the inner peripheral surface 31i of the first needle tip portion 31F. As shown in FIGS. 27 and 32, the fourth inner line 36c of intersection is a line of intersection that is formed by the fourth blade surface 36 and the inner peripheral surface 32l of the second needle tip portion 32F. The eighth blade surface 44 and the second inner line 34c of intersection intersect with each other at the second inner intersection 34e, and the eighth blade surface 44 and the fourth inner line 36c of intersection intersect with each other at the fourth inner intersection 36e.

As shown in FIGS. 33 to 35, a line of intersection at which the eighth blade surface 44 and the second blade surface 34 intersect with each other is a second intermediate edge 34f. A line of intersection at which the eighth blade surface 44 and the fourth blade surface 36 intersect with each other is a fourth intermediate edge 36f. The second intermediate edge 34f and the fourth intermediate edge 36f are connected to each other at the second proximal end 39.

As shown in FIGS. 29 and 34, an angle 34k formed between the eighth blade surface 44 and the second blade surface 34 at the second intermediate edge 34f is reduced toward the proximal end of the needle tube 3F from the distal end of the needle tube 3F.

As shown in FIGS. 29 and 34, an angle 36k formed between the eighth blade surface 44 and the fourth blade surface 36 at the fourth intermediate edge 36f is reduced toward the proximal end of the needle tube 3F from the distal end of the needle tube 3F.

As shown in FIG. 29, the curvatures of curves, which are formed by the second intermediate edge 34f and the fourth intermediate edge 36f, are larger than the curvature of the inner peripheral surface 30i of the tubular portion 30 in a cross section perpendicular to the axial direction A.

As shown in FIGS. 29 to 32, in the first proximal end region Z31, a thickness T2 between the eighth blade surface 44 and the outer peripheral surface 31e of the first needle tip portion 31F is reduced toward the second proximal end 39 from the second inner intersection 34e. Likewise, in the first proximal end region Z31, the thickness T2 is reduced toward the second proximal end 39 from the fourth inner intersection 36e.

As shown in FIGS. 29 to 32, in the second proximal end region Z32, the thickness T2 between the eighth blade surface 44 and the outer peripheral surface 31e of the first needle tip portion 31F is increased toward the proximal end side of the needle tube 3F from the second proximal end 39. Likewise, a thickness T2 between the eighth blade surface 44 and the outer peripheral surface 32e of the second needle tip portion 32F is increased toward the proximal end side of the needle tube 3F from the second proximal end 39. That is, the thicknesses T1 between the eighth blade surface 44 and the outer peripheral surfaces 31e and 32e are reduced toward the second proximal end 39 from the proximal end of the eighth blade surface.

In a side view seen in a direction orthogonal to the central axis O and the straight line V, the second inner intersection 34e and the fourth inner intersection 36e are formed at positions symmetric with respect to the central axis O extending in the axial direction A of the needle tube 3F. As shown in FIGS. 31 and 32, the second inner intersection 34e and the fourth inner intersection 36e are positioned at the distal end of the eighth blade surface 44.

A line of intersection, which is formed by the eighth blade surface 44 and the inner peripheral surface 31i of the first needle tip portion 31F, is defined as an eighth line 440 of intersection. As shown in FIG. 27, an interval between a first portion 441, which is connected to the inner peripheral surface 31i, and a third portion 442, which is connected to the inner peripheral surface 32i, of the eighth line 440 of intersection is gradually reduced toward the proximal end of the eighth blade surface 44 from the distal end of the eighth blade surface 44.

As shown in FIG. 32, a second proximal end edge 39f of which the distal end is the second proximal end 39 is formed in the second proximal end region Z32. The second proximal end edge 39f is a sharp blade that is formed by the eighth blade surface 44 and the outer peripheral surfaces 31e and 32e. The thickness T2 at the second proximal end 39 is set to be small, so that a resistance force, which is applied to the second proximal end 39 from tissue in a case where the body tissue is punctured by the needle tube 3F, can be reduced. Further, distal end angles formed between the eighth blade surface 44 and the outer peripheral surfaces 31e and 32e are set to be small at the second proximal end 39, so that the second proximal end edge 39f is formed.

For example, the inner peripheral surface 30i of the tubular portion 30 of the needle tube 3F is cut, so that the seventh blade surface 43 and the eighth blade surface 44 are formed. It is desired that the first inner intersection 33e and the second inner intersection 34e are formed at positions symmetric with respect to the straight line V passing through the first needle tip 31a and the second needle tip 32a as shown in FIG. 29 in a front view seen in a direction along the axial direction A of the needle tube 3F (tubular portion 30). Likewise, it is desired that the third inner intersection 35e and the fourth inner intersection 36e are formed at positions symmetric with respect to the straight line V passing through the first needle tip 31a and the second needle tip 32a in the front view.

According to the biopsy system 150F including the puncture needle 1F according to this embodiment, not only the first outer edge 33b, the second outer edge 34b, the third outer edge 35b, and the fourth outer edge 36b but also the first proximal end edge 38f and the second proximal end edge 39f cut into body tissue. Accordingly, it is easy to collect the body tissue (a sample required for diagnosis).

According to the biopsy system 150F including the puncture needle 1F according to this embodiment, insertability into body tissue is high and it is easy to collect the cut-out body tissue into the puncture needle 1F. Since the first proximal end 38 and the second proximal end 39 of the needle tube 3F are thinner and sharper than those of the needle tube 3 of the above embodiment (FIGS. 1-10), the needle tube 3F has higher punctureability in addition to collectability. As in the above embodiment (FIGS. 1-10), the normal vector 33n of the first blade surface 33 and the normal vector 34n of the second blade surface 34 in the distal end region 21 are directed to the third blade surface 35 and the fourth blade surface 36 in the distal end region Z1, respectively, as compared to a direction that is orthogonal to the straight line V passing through the first needle tip 31a and the second needle tip 32a. Further, in the front view, the normal vector 35n of the third blade surface 35 and the normal vector 36n of the fourth blade surface 36 in the distal end region 21 are directed to the first blade surface 33 and the second blade surface 34 in the distal end region z1 as compared to a direction that is orthogonal to the straight line V passing through the first needle tip 31a and the second needle tip 32a. For this reason, the puncture needle 1F can allow the target tissue T to be suitably moved into the needle tube 3.

Figure 36:
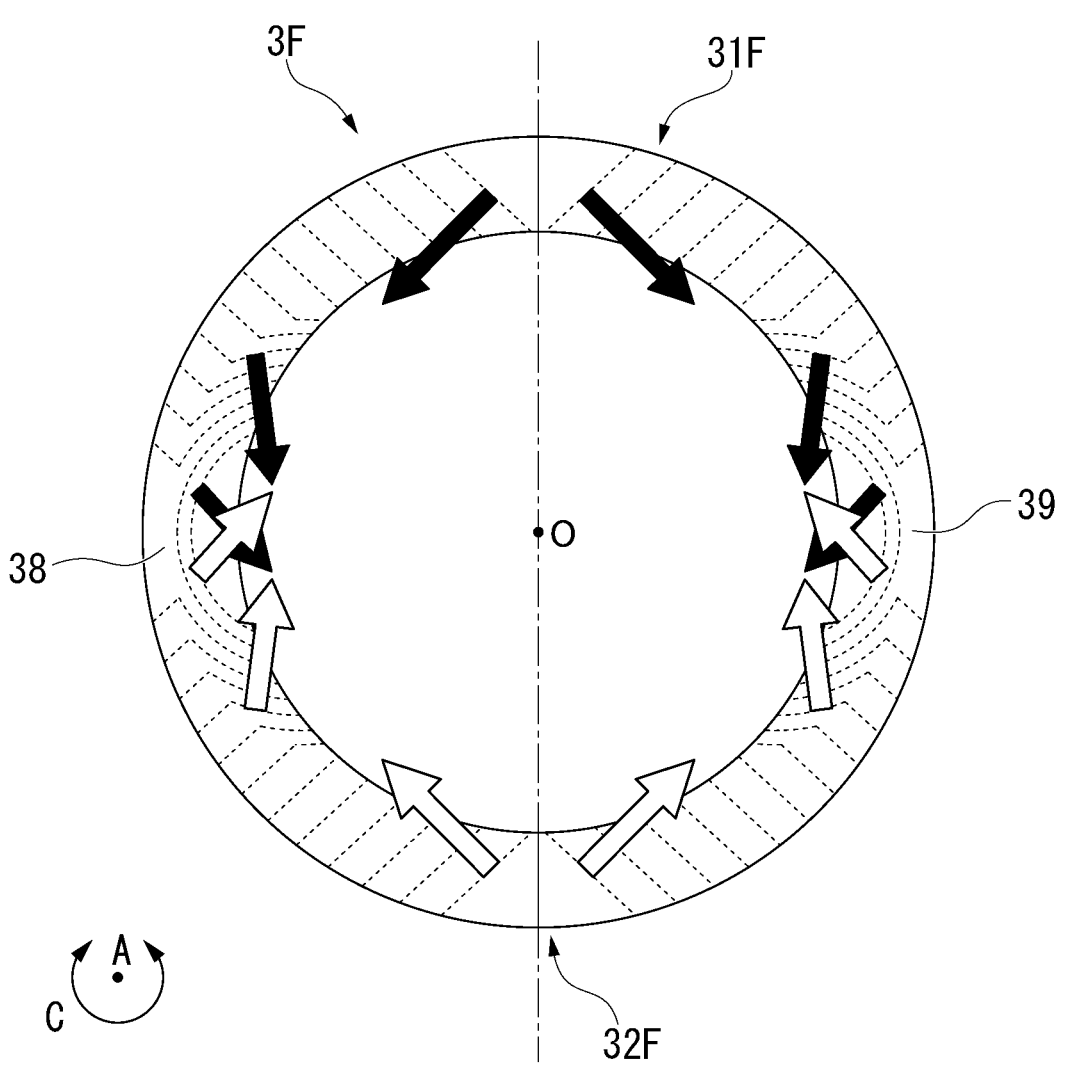
FIG. 36 is a diagram in which normals to blade surfaces, such as a first blade surface, which are main blade surfaces, are displayed by arrows in a cross section perpendicular to an axial direction A in a diagram shown in FIG. 29.

FIG. 36 is a diagram in which normals to blade surfaces, such as the first blade surface 33, which are main blade surfaces, are displayed by arrows in a cross section perpendicular to the axial direction A in the diagram shown in FIG. 29. In the needle tube 3F, the normals to the blade surfaces are directed to directions that further approach the central axis O toward the proximal end of the needle tube 3F from the distal end of the needle tube 3F as compared to the circumferential direction C of the tubular portion 30. As a result, the collectability of the needle tube 3F is higher than that of the needle tube 3 of the above embodiment (FIGS. 1-10).

This embodiment has been described in detail above with reference to the drawings, but specific configuration is not limited to this embodiment and also includes design changes and the like without departing from the scope of the present disclosure. Further, components shown in the above-mentioned embodiment and a modification example can be appropriately combined.

A biopsy system 150G including an endoscope puncture needle 1G according to another exemplary embodiment of the present disclosure will be described with reference to FIGS. 37 to 48. In the following description, components common to the already described components will be denoted by the same reference numerals and the repeated description thereof will be omitted. The endoscope puncture needle 1G is different from the endoscope puncture needle 1 according to the above embodiment (FIGS. 1-10) in terms of the shape of a blade surface.

[Biopsy System 150G]

The biopsy system 150G is medical equipment that is used to collect tissue in a body during a biopsy. The biopsy system 150G includes an ultrasound endoscope 100 and an endoscope puncture needle 1G (hereinafter, simply referred to as a "puncture needle 1G".). The puncture needle 1G includes an insertion body 2G, an operation unit 8, and a stylet 27.

[Insertion Body 2G]

The insertion body 2G is an elongated member that can be inserted into a channel 107 of the ultrasound endoscope 100. The insertion body 2G includes a needle tube 3G and a sheath 7.

Figure 37:
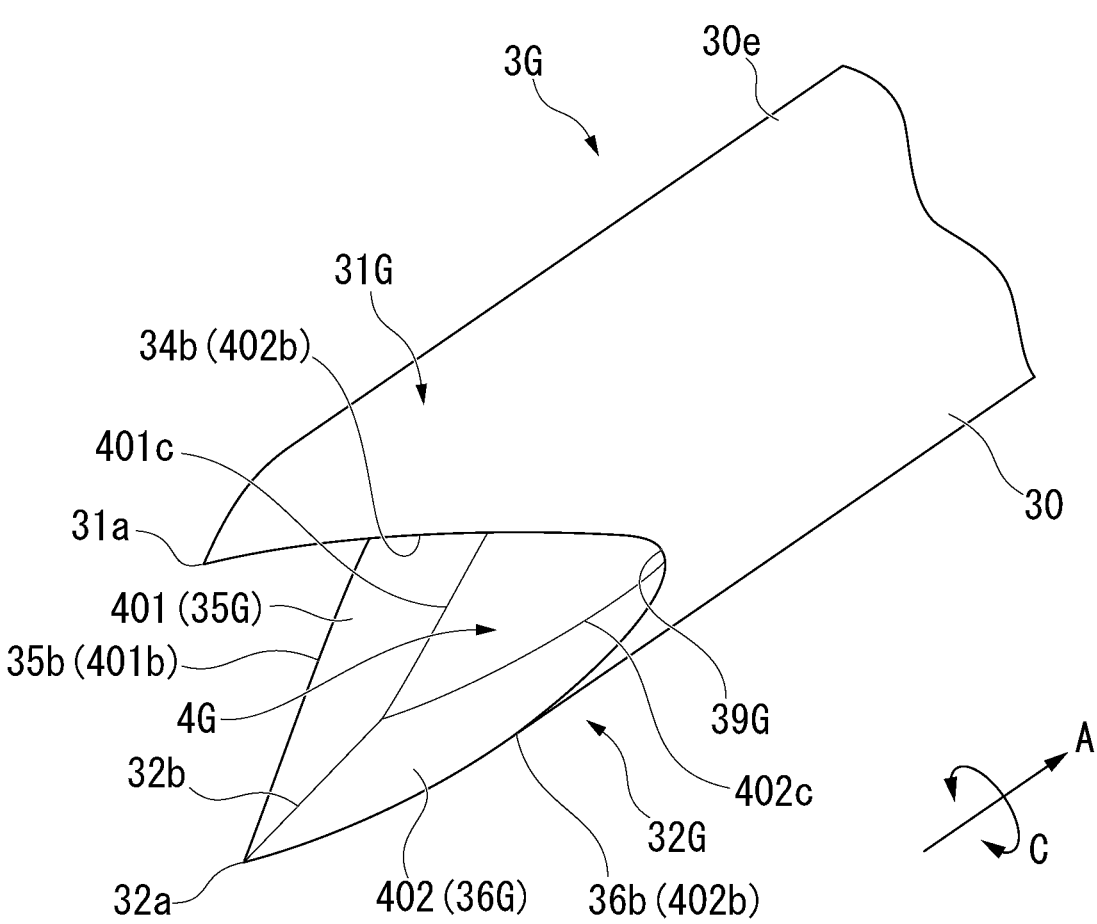
FIG. 37 is a perspective view of a needle tube included in an endoscope puncture needle according to an exemplary embodiment.
Figure 38:
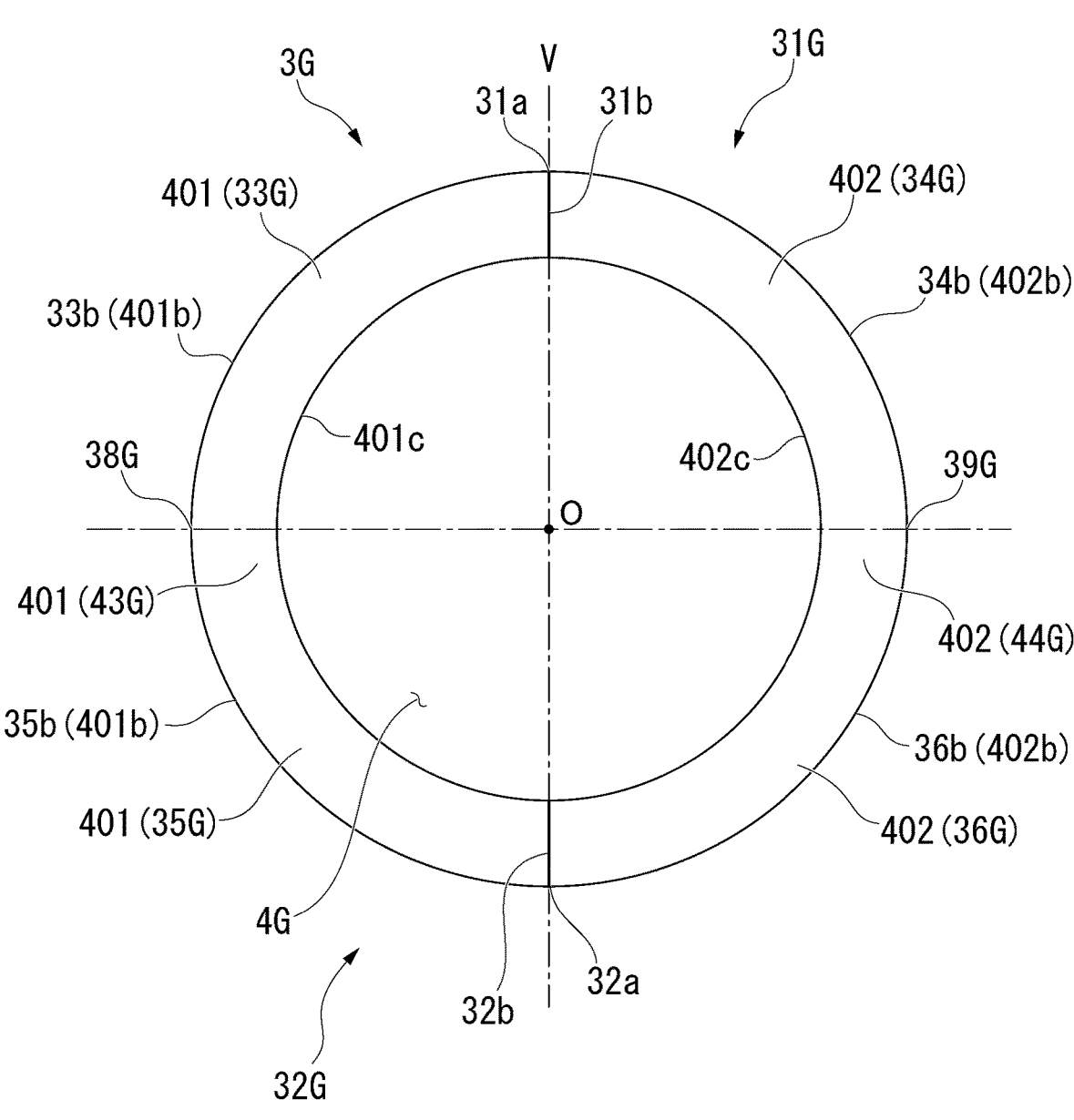
FIG. 38 is a front view of the needle tube.
Figure 39:
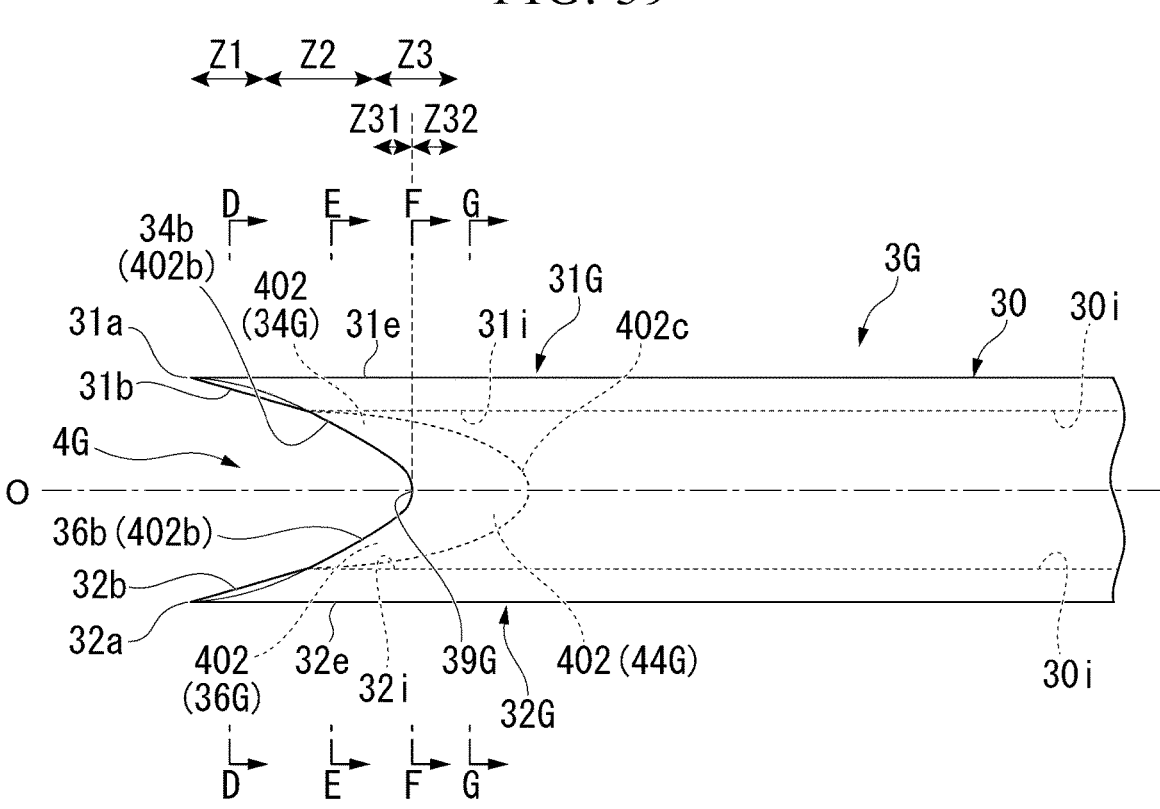
FIG. 39 is a side view of the needle tube.
Figure 40:
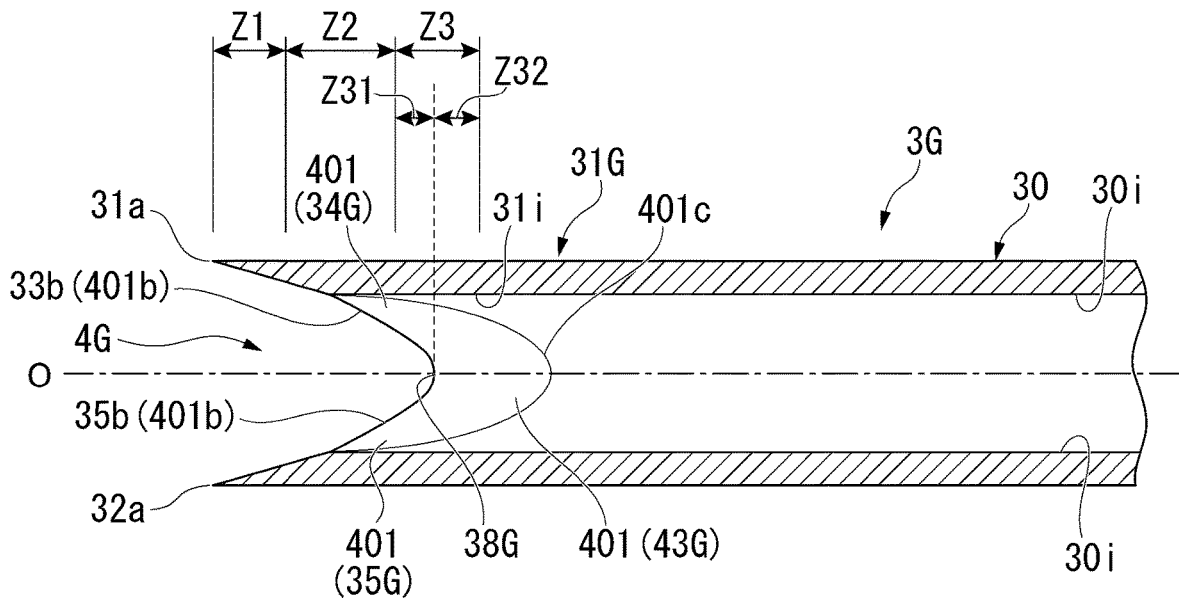
FIG. 40 is a cross-sectional view taken along a central axis of the needle tube and seen in the same direction as FIG. 39.
Figure 41:
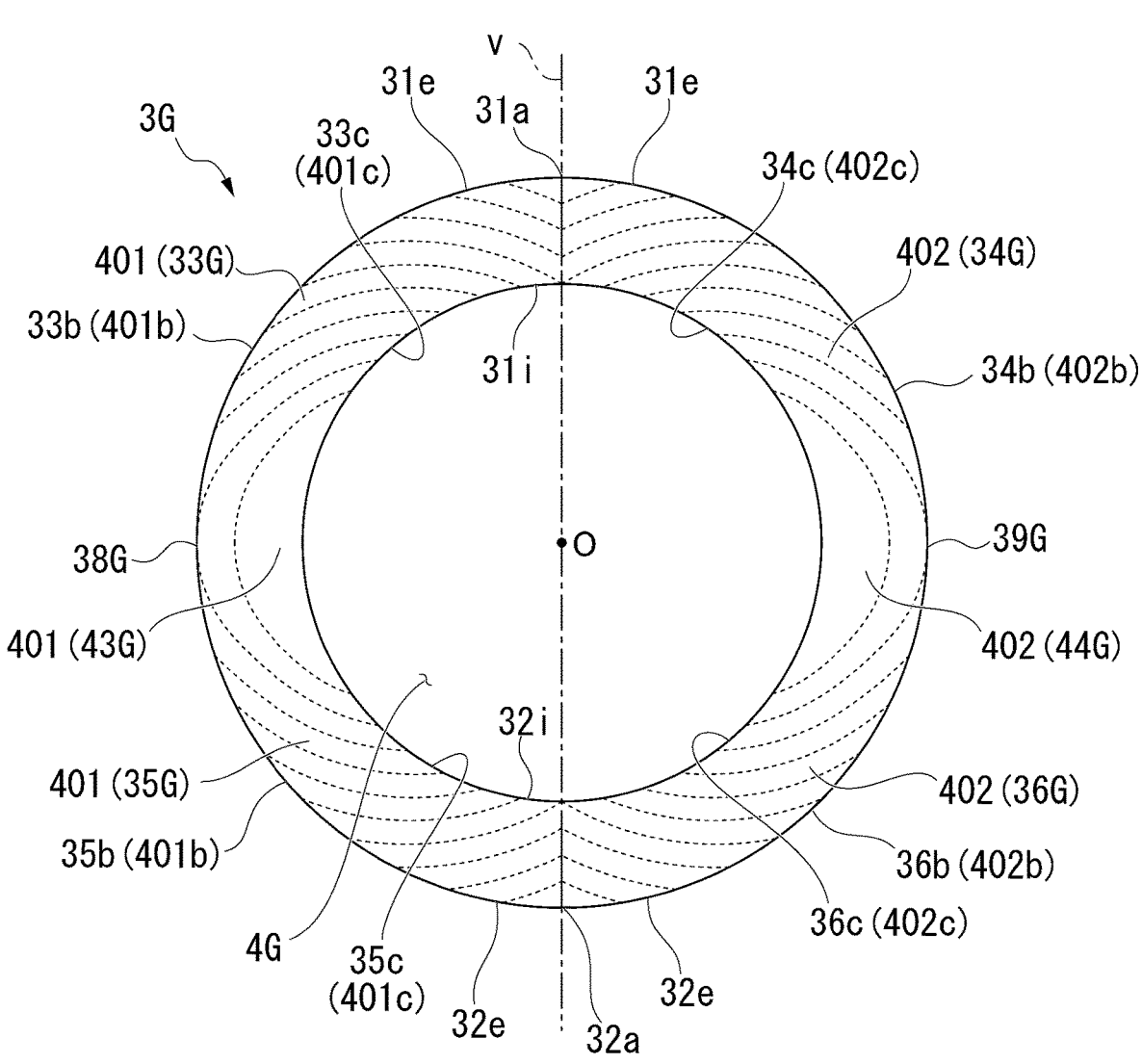
FIG. 41 is a front view of the needle tube seen from a distal end in an axial direction, and is a diagram in which cross sections are arranged at regular intervals in the direction of a longitudinal axis and which schematically shows a change in the orientation of the cross section of each blade surface.
Figure 42:
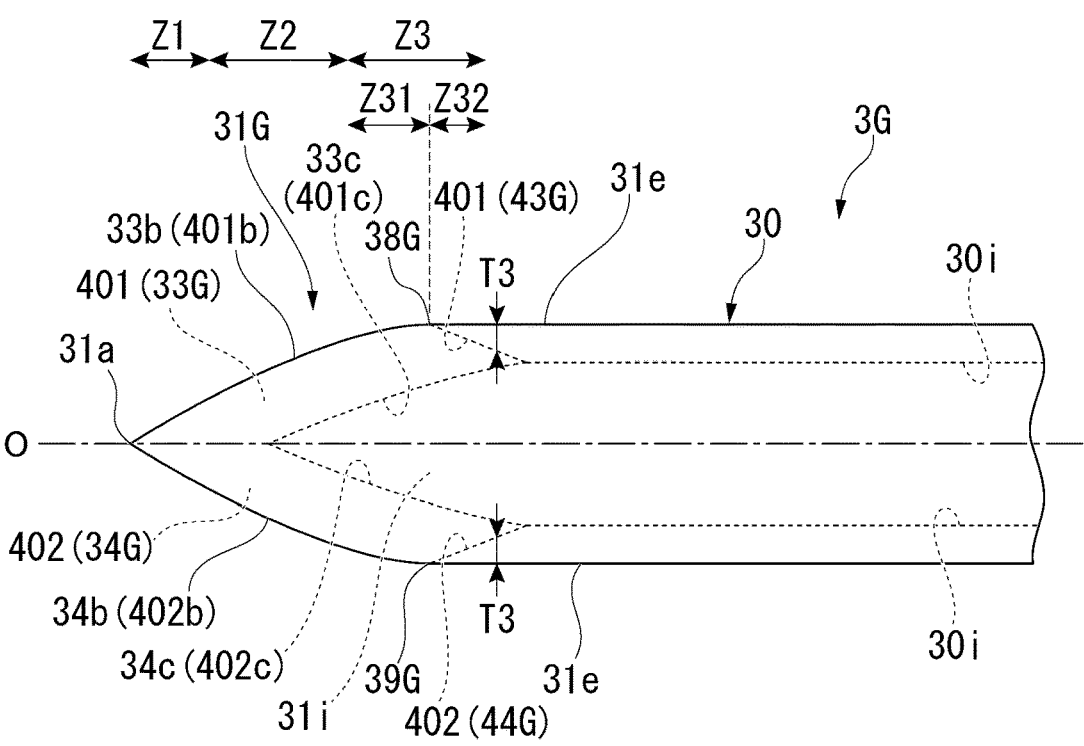
FIG. 42 is a plan view seen in a direction that is horizontal with respect to a straight line V.
Figure 43:
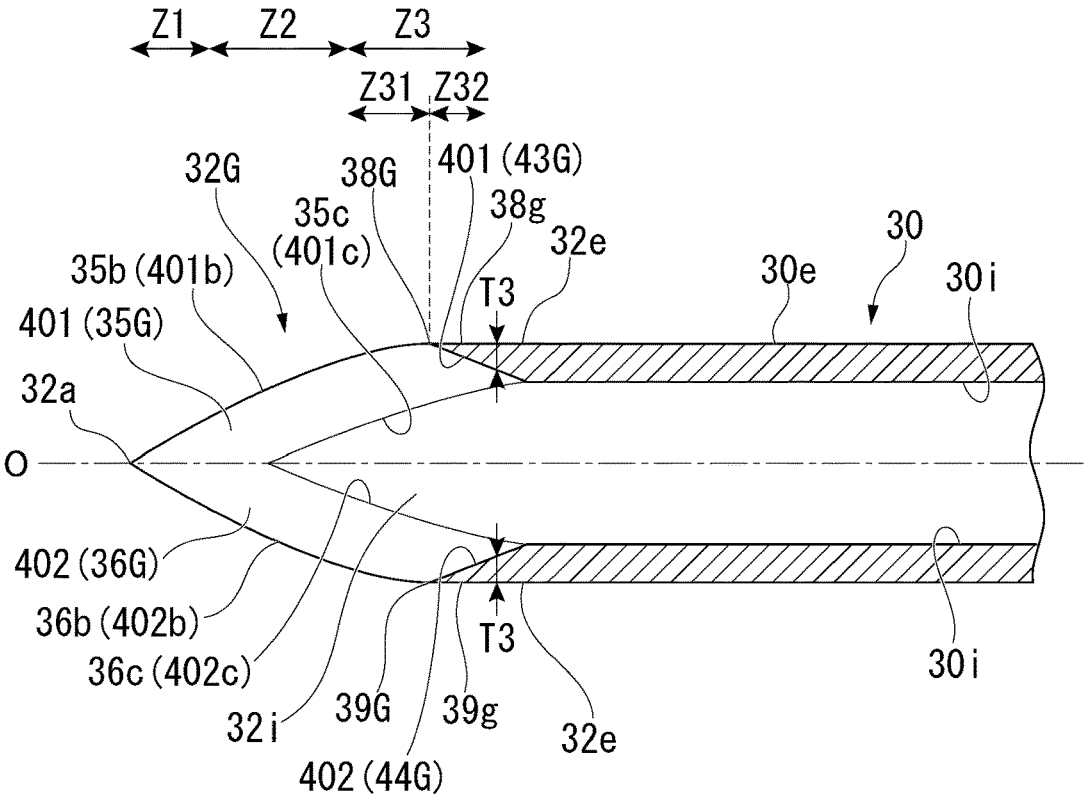
FIG. 43 is a cross-sectional view taken along a central axis and seen in the same direction as FIG. 42.

FIG. 37 is a perspective view of the needle tube 3G. FIG. 38 is a front view of the needle tube 3G. FIG. 39 is a side view of the needle tube 3G. FIG. 40 is a cross-sectional view taken along a central axis O of the needle tube 3E and seen in the same direction as FIG. 39. FIG. 41 is a front view of the needle tube 3G seen from a distal end in an axial direction A, and is a diagram in which cross sections are arranged at regular intervals in the direction of a longitudinal axis and which schematically shows a change in the orientation of the cross section of each blade surface. A one-dot chain line shown in FIG. 41 indicates a line of intersection between cross sections, which are arranged at regular intervals in the axial direction A and are perpendicular to the axial direction A, and a first blade surface 33G, a second blade surface 34G, a third blade surface 35G, and a fourth blade surface 36G. FIG. 42 is a plan view seen in a direction that is horizontal with respect to a straight line V. FIG. 43 is a cross-sectional view taken along the central axis O and seen in the same direction as FIG. 42.

Figure 44:
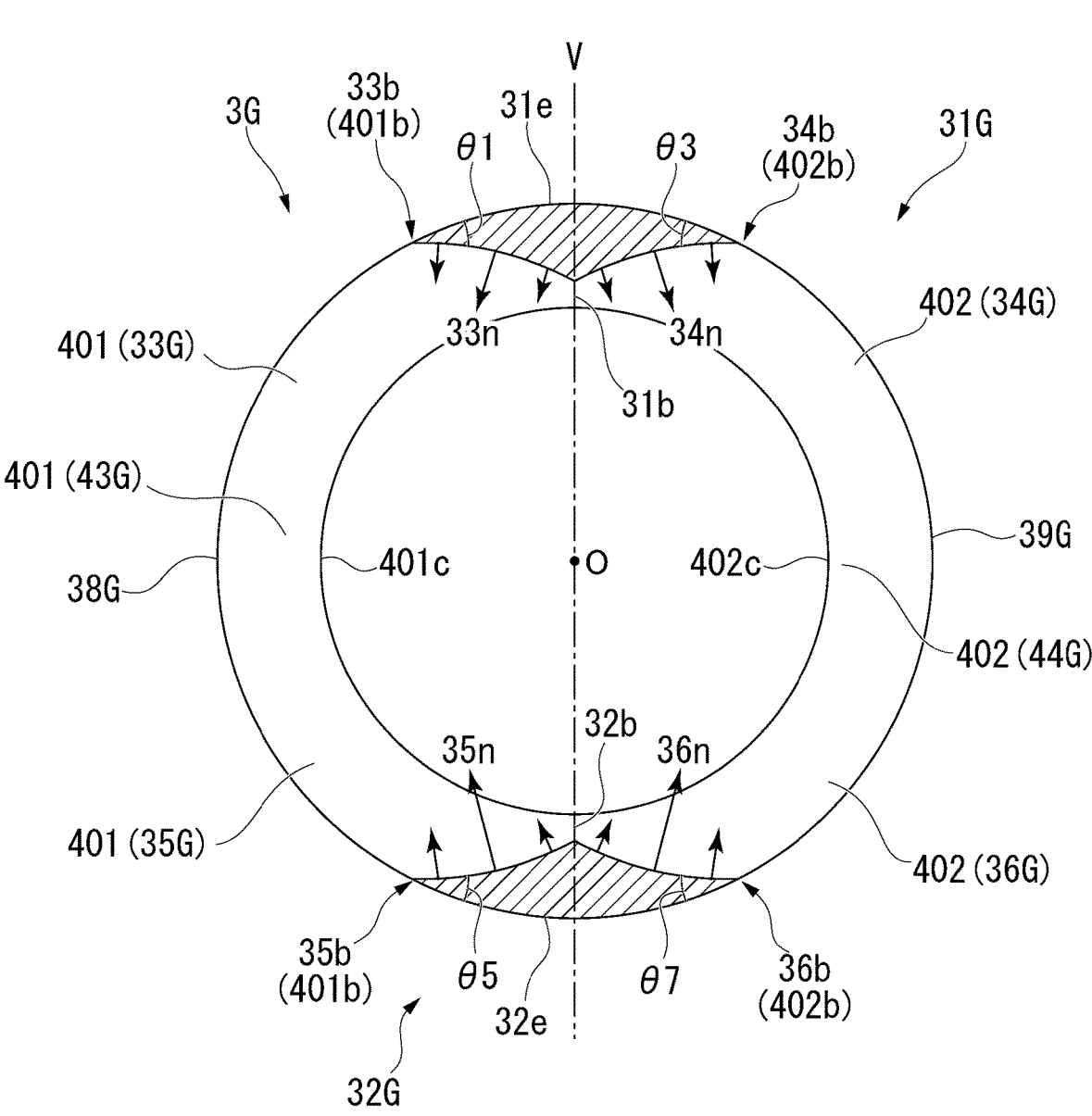
FIG. 44 is a cross-sectional view taken along line D-D of the needle tube shown in FIG. 39.
Figure 45:
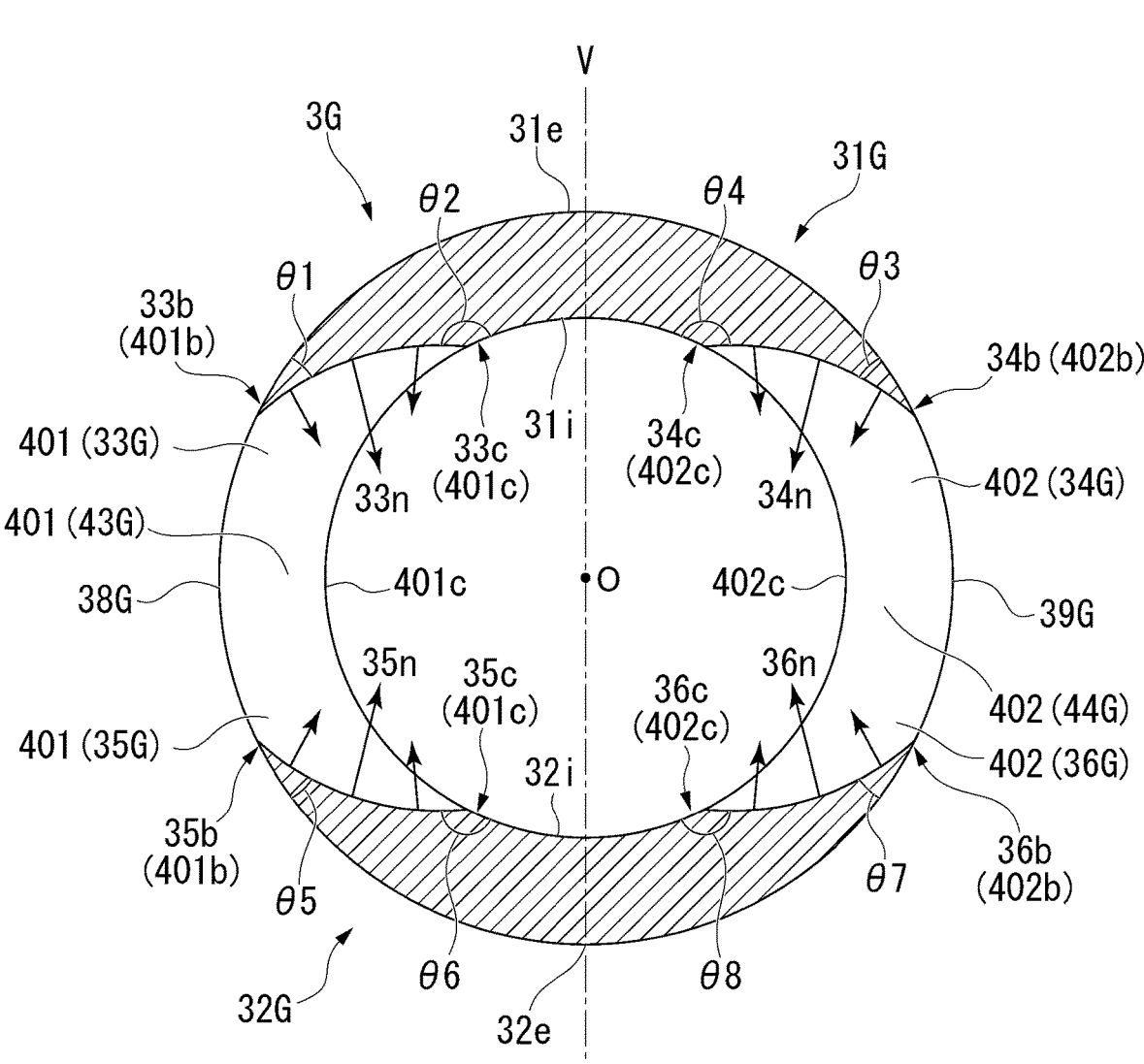
FIG. 45 is a cross-sectional view taken along line E-E of the needle tube shown in FIG. 39.
Figure 46:
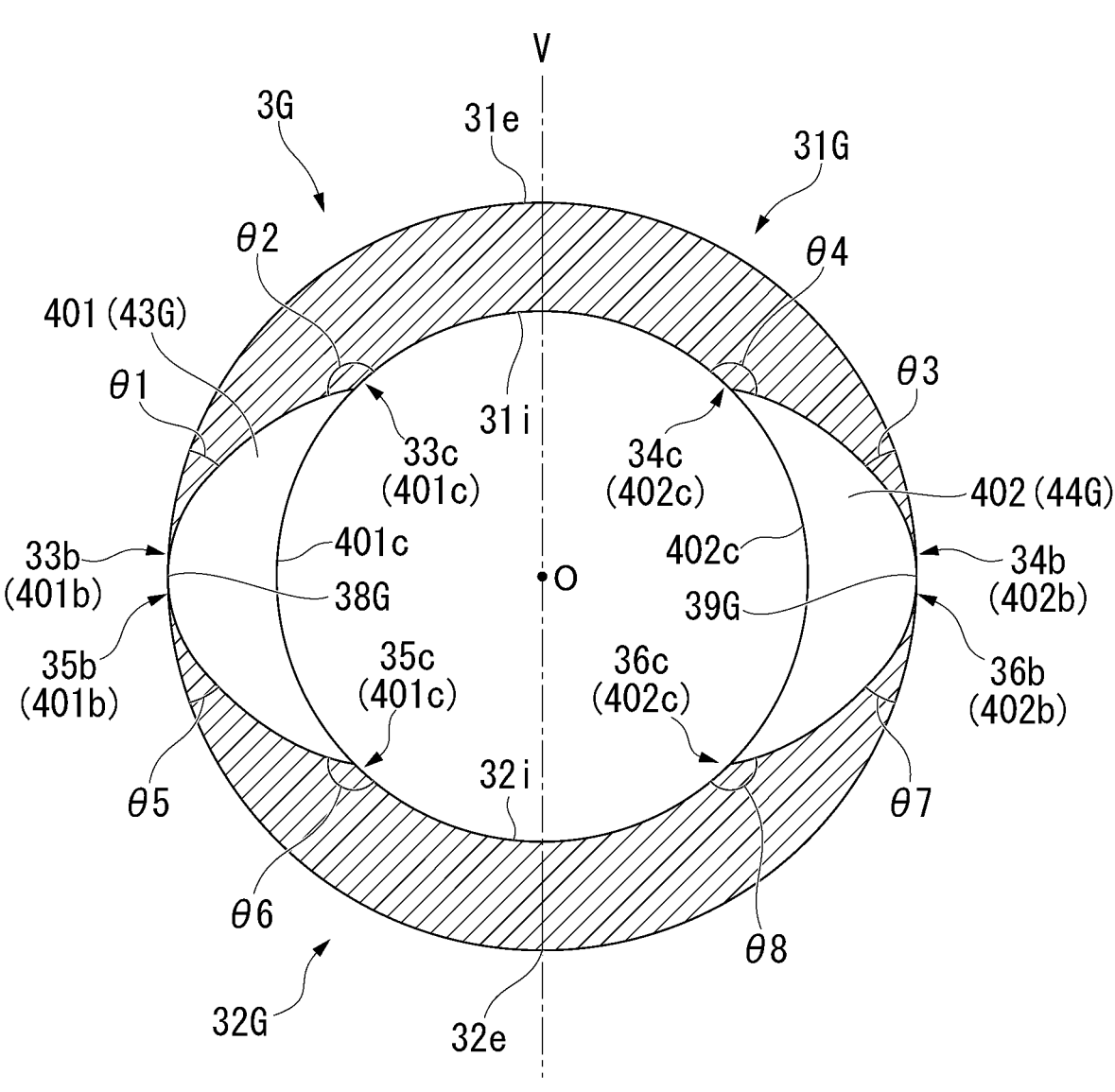
FIG. 46 is a cross-sectional view taken along line F-F of the needle tube shown in FIG. 39.
Figure 47:
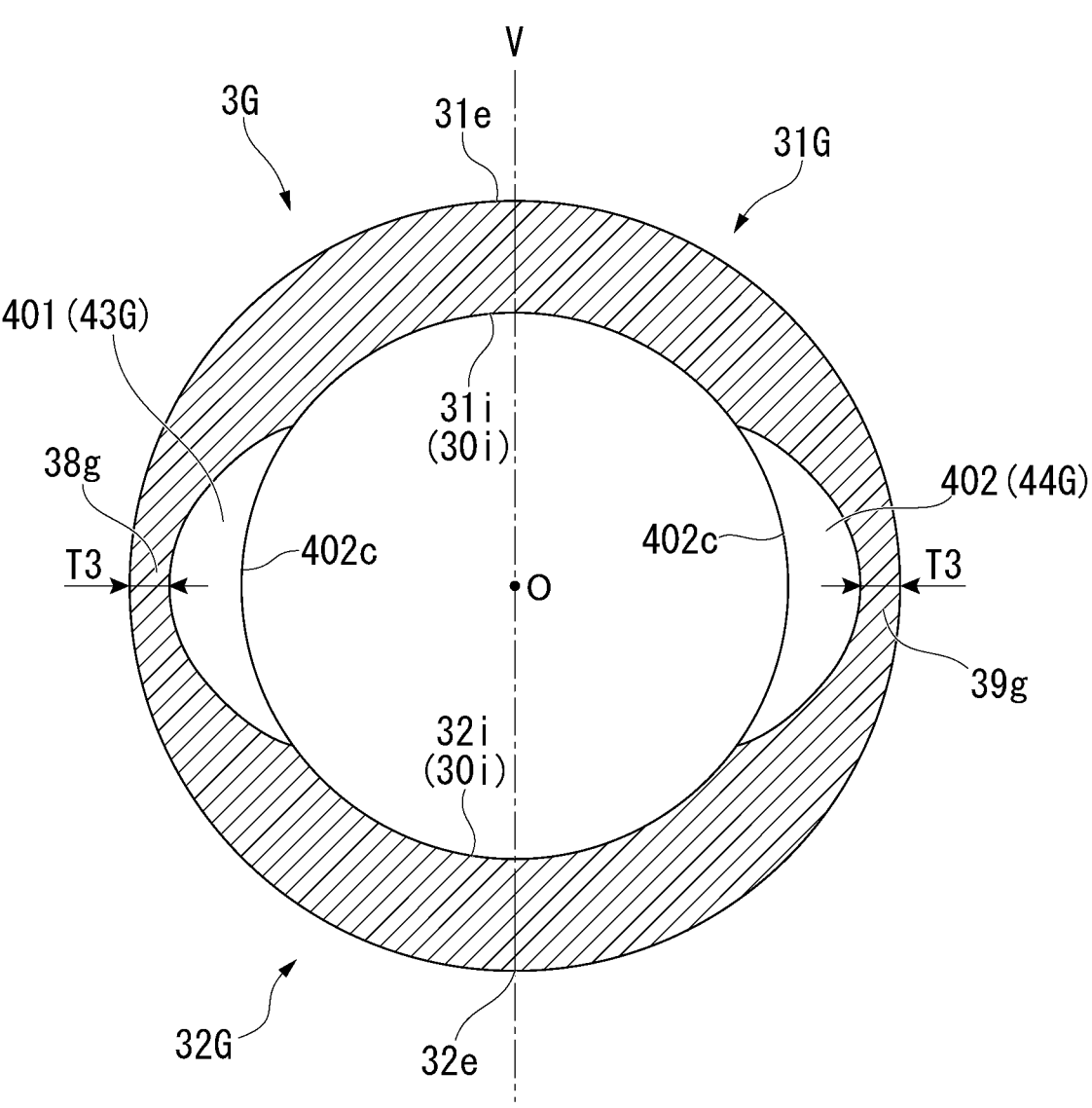
FIG. 47 is a cross-sectional view taken along line G-G of the needle tube shown in FIG. 39.

FIG. 44 is a cross-sectional view taken along line D-D of the needle tube 3G shown in FIG. 39. FIG. 45 is a cross-sectional view taken along line E-E of the needle tube 3G shown in FIG. 39. FIG. 46 is a cross-sectional view taken along line F-F of the needle tube 3G shown in FIG. 39. Line F-F passes through a first proximal end 38G and a second proximal end 39G to be described later. FIG. 47 is a cross-sectional view taken along line G-G of the needle tube 3G shown in FIG. 39.

As shown in FIG. 37, the needle tube 3G includes a tubular portion 30 having a tubular shape, and a first needle tip portion 31G and a second needle tip portion 32G provided at the distal end of the tubular portion 30. The needle tube 3G can be operated to advance and retreat in the sheath 7 by the operation unit 8. An opening 4G, which serves as an entrance through which tissue punctured by the first needle tip portion 31G and the second needle tip portion 32G enters the inside of the needle tube 3G, is formed at the distal end of the needle tube 3G. The first needle tip portion 31G and the second needle tip portion 32G of the needle tube 3G can protrude and retract from an opening formed at the distal end portion of the sheath 7.

As shown in FIGS. 37 to 43, the first needle tip portion 31G includes a first outer edge 33b and a second outer edge 34b that are formed along an outer peripheral surface 31e of the first needle tip portion 31G. The first outer edge 33b and the second outer edge 34b extend toward a sharp first needle tip 31a. In a front view seen in a direction along the axial direction A of the needle tube 3G (tubular portion 30), the first outer edge 33b and the second outer edge 34b have shapes symmetric with respect to the straight line V passing through the first needle tip 31a and a second needle tip 32a as shown in FIG. 38. For example, a part of the tubular portion 30 is cut off, so that the first outer edge 33b and the second outer edge 34b are formed.

The outer peripheral surface 31e of the first needle tip portion 31G is a curved surface continuous with an outer peripheral surface 30e of the tubular portion 30, and has the same diameter and curvature as the outer peripheral surface 30e. Further, an inner peripheral surface 31i of the first needle tip portion 31G is a curved surface continuous with an inner peripheral surface 30i of the tubular portion 30, and has the same diameter and curvature as the inner peripheral surface 30i.

As shown in FIGS. 37 to 43, the second needle tip portion 32G includes a third outer edge 35b and a fourth outer edge 36b that are formed along the outer peripheral surface 31e of the first needle tip portion 31G. The third outer edge 35b and the fourth outer edge 36b extend toward the sharp second needle tip 32a. The first needle tip 31a and the second needle tip 32a are disposed at positions symmetric with respect to the central axis O extending in the axial direction A of the needle tube 3G. In a front view seen in a direction along the axial direction A of the needle tube 3G, the third outer edge 35b and the fourth outer edge 36b have shapes symmetric with respect to the straight line V passing through the first needle tip 31a and the second needle tip 32a as shown in FIG. 38. For example, a part of the tubular portion 30 is cut off, so that the third outer edge 35b and the fourth outer edge 36b are formed.

An outer peripheral surface 32e of the second needle tip portion 32G is a curved surface continuous with the outer peripheral surface 30e of the tubular portion 30, and has the same diameter and curvature as the outer peripheral surface 30e. Further, an inner peripheral surface 32l of the second needle tip portion 32G is a curved surface continuous with the inner peripheral surface 30i of the tubular portion 30, and has the same diameter and curvature as the inner peripheral surface 30i.

As shown in FIGS. 37 to 43, the proximal end of the first outer edge 33b and the proximal end of the third outer edge 35b are connected to each other at the first proximal end 38G. The proximal end of the second outer edge 34b and the proximal end of the fourth outer edge 36b are connected to each other at the second proximal end 39G. As shown in FIGS. 39 and 40, in a side view seen in a direction orthogonal to the central axis O and the straight line V, the first proximal end 38G and the second proximal end 39G are formed at positions symmetric with respect to the central axis O extending in the axial direction A of the needle tube 3G.

As shown in FIGS. 39 and 40, a distal end region Z1 that includes the first needle tip 31a and the second needle tip 32a, a proximal end region 23 that includes the first proximal end 38G and the second proximal end 39G, and an intermediate region Z2 that is positioned between the distal end region Z1 and the proximal end region Z3 and is connected to the distal end region Z1 and the proximal end region 23 are defined at the first needle tip portion 31G and the second needle tip portion 32G. Further, a region of the proximal end region 23, which is positioned closer to the distal end side than the first proximal end 38G and the second proximal end 39G in the axial direction A, is defined as a first proximal end region Z31 and a region of the proximal end region Z3, which is positioned closer to the proximal end side than the first proximal end 38G and the second proximal end 39G in the axial direction A, is defined as a second proximal end region Z32.

(First Continuous Blade Surface 401 and Second Continuous Blade Surface 402)

As shown in FIGS. 37 and 38, the first needle tip portion 31G and the second needle tip portion 32G include a first continuous blade surface 401 and a second continuous blade surface 402.

The first continuous blade surface 401 is formed on the inner peripheral surface 31i of the first needle tip portion 31G and the inner peripheral surface 32l of the second needle tip portion 32G, and has the shape of a continuous curved surface. The first continuous blade surface 401 extends over the first needle tip portion 31G and the second needle tip portion 32G. Specifically, as shown in FIGS. 38 and 40, the first continuous blade surface 401 extends toward the proximal end side of the needle tube 3G from the first needle tip 31a. Further, the first continuous blade surface 401 extends toward the proximal end side of the needle tube 3G from the second needle tip 32a. The proximal end of the first continuous blade surface 401 is positioned closer to the proximal end side of the needle tube 3G than the first proximal end 38G of the edge of the opening 4G.

As shown in FIG. 37, the first continuous blade surface 401 includes a first continuous blade surface-outer edge 401b that is a line of intersection between the first continuous blade surface 401 and the outer peripheral surface 31e of the first needle tip portion 31G and the outer peripheral surface 32e of the second needle tip portion 32G. The proximal end of the first continuous blade surface-outer edge 401b coincides with the first proximal end 38G. As shown in FIGS. 40 and 42, a thickness T3 between the first continuous blade surface 401 and the outer peripheral surface 31e of the first needle tip portion 31G is reduced toward the first proximal end 38G from the proximal end of a first continuous blade surface-inner edge 401c (the proximal end of the first continuous blade surface 401). As shown in FIGS. 40 and 43, a thickness T3 between the first continuous blade surface 401 and the outer peripheral surface 32e of the second needle tip portion 32G is reduced toward the first proximal end 38G from the proximal end of the first continuous blade surface-inner edge 401c (the proximal end of the first continuous blade surface 401). The first continuous blade surface-inner edge 401c is a line of intersection between the first continuous blade surface 401 and the inner peripheral surfaces 31i and 32i, and is positioned closer to the inside of the needle tube 3G in a radial direction than the first outer edge 33b and the third outer edge 35b.

As shown in FIGS. 39 and 40, in a side view seen in a direction orthogonal to the central axis O and the straight line V, the first continuous blade surface-inner edge 401c extends toward the proximal end side of the needle tube 3G from the proximal end of a first distal end line 31b of intersection extending from the first needle tip 31a. Further, the first continuous blade surface-inner edge 401c extends toward the proximal end side of the needle tube 3G from the proximal end of a second distal end line 32b of intersection extending from the second needle tip 32a. The proximal end of the first continuous blade surface-inner edge 401c is positioned closer to the proximal end side of the needle tube 3G than the first proximal end 38G, and a portion of the first continuous blade surface-inner edge 401c extending toward the proximal end side of the needle tube 3G from the proximal end of the first distal end line 31b of intersection and a portion of the first continuous blade surface-inner edge 401c extending toward the proximal end side of the needle tube 3G from the proximal end of the second distal end line 32b of intersection are connected to each other at the proximal end of the first continuous blade surface-inner edge 401c.

As shown in FIG. 40, the first continuous blade surface 401 includes a first blade surface 33G that abuts on the first outer edge 33b and is closer to the distal end side than the first proximal end 38G, a third blade surface 35G that abuts on the third outer edge 35b and is closer to the distal end side than the first proximal end 38G, and a seventh blade surface 43G that is closer to the proximal end side than the first proximal end 38G. The first blade surface 33G and the seventh blade surface 43G have the shape of a continuously connected curved surface, and are preferably continuous with each other without a level difference between the first blade surface 33G and the seventh blade surface 43G. The third blade surface 35G and the seventh blade surface 43G have the shape of a continuously connected curved surface, and are preferably continuous with each other without a level difference between the third blade surface 35G and the seventh blade surface 43G.

The second continuous blade surface 402 is formed on the inner peripheral surface 31i of the first needle tip portion 31G and the inner peripheral surface 32l of the second needle tip portion 32G, and has the shape of a continuous curved surface. The second continuous blade surface 402 extends over the first needle tip portion 31G and the second needle tip portion 32G. Specifically, as shown in FIGS. 38 and 39, the second continuous blade surface 402 extends toward the proximal end side of the needle tube 3G from the first needle tip 31a. Further, the second continuous blade surface 402 extends toward the proximal end side of the needle tube 3G from the second needle tip 32a. The proximal end of the second continuous blade surface 402 is positioned closer to the proximal end side of the needle tube 3G than the second proximal end 39G of the edge of the opening 4G.

As shown in FIG. 37, the second continuous blade surface 402 includes a second continuous blade surface-outer edge 402b that is a line of intersection between the second continuous blade surface 402 and the outer peripheral surface 31e of the first needle tip portion 31G and the outer peripheral surface 32e of the second needle tip portion 32G. The proximal end of the second continuous blade surface-outer edge 402b coincides with the second proximal end 39G. As shown in FIGS. 39 and 42, a thickness T3 between the second continuous blade surface 402 and the outer peripheral surface 31e of the first needle tip portion 31G is reduced toward the second proximal end 39G from the proximal end of a second continuous blade surface-inner edge 402c (the proximal end of the second continuous blade surface 402). As shown in FIGS. 39 and 43, a thickness T3 between the second continuous blade surface 402 and the outer peripheral surface 32e of the second needle tip portion 32G is reduced toward the second proximal end 39G from the proximal end of the second continuous blade surface-inner edge 402c (the proximal end of the second continuous blade surface 402). The second continuous blade surface-inner edge 402c is a line of intersection between the second continuous blade surface 402 and the inner peripheral surfaces 31i and 32i, and is positioned closer to the inside of the needle tube 3G in a radial direction than the second outer edge 34b and the fourth outer edge 36b.

As shown in FIG. 39, in a side view seen in a direction orthogonal to the central axis O and the straight line V, the second continuous blade surface-inner edge 402c extends toward the proximal end side of the needle tube 3G from the proximal end of the first distal end line 31b of intersection extending from the first needle tip 31a. Further, the second continuous blade surface-inner edge 402c extends toward the proximal end side of the needle tube 3G from the proximal end of the second distal end line 32b of intersection extending from the second needle tip 32a. The proximal end of the second continuous blade surface-inner edge 402c is positioned closer to the proximal end side of the needle tube 3G than the second proximal end 39G, and a portion of the second continuous blade surface-inner edge 402c extending toward the proximal end side of the needle tube 3G from the proximal end of the first distal end line 31b of intersection and a portion of the second continuous blade surface-inner edge 402c extending toward the proximal end side of the needle tube 3G from the proximal end of the second distal end line 32b of intersection are connected to each other at the proximal end of the second continuous blade surface-inner edge 402c.

As shown in FIG. 39, the second continuous blade surface 402 includes a second blade surface 34G that abuts on the second outer edge 34b and is closer to the distal end side than the second proximal end 39G, a fourth blade surface 36G that abuts on the fourth outer edge 36*b* and is closer to the distal end side than the second proximal end 39G, and an eighth blade surface 44G that is closer to the proximal end side than the second proximal end 39G. The second blade surface 34G and the eighth blade surface 44G have the shape of a continuously connected curved surface, and are preferably continuous with each other without a level difference between the second blade surface 34G and the eighth blade surface 44G. The fourth blade surface 36G and the eighth blade surface 44G have the shape of a continuous curved surface, and are preferably continuous with each other without a level difference between the fourth blade surface 36G and the eighth blade surface 44G.

In a front view seen in a direction along the axial direction A of the needle tube 3G, the first continuous blade surface 401 and the second continuous blade surface 402 have shapes symmetric with respect to the straight line V as shown in FIGS. 38 and 41.

As shown in FIG. 38, the line of intersection (first distal end line 31*b* of intersection) between the first blade surface 33G and the second blade surface 34G extends up to the first needle tip 31*a* from the distal end of the inner peripheral surface 31*i* of the first needle tip portion 31G. The first distal end line 31*b* of intersection is positioned on the straight line V in a front view seen in a direction along the axial direction A of the needle tube 3G.

As shown in FIG. 38, the line of intersection (second distal end line 32*b* of intersection) between the third blade surface 35G and the fourth blade surface 36G extends up to the first needle tip 31*a* from the distal end of the inner peripheral surface 31*i* of the second needle tip portion 32G. The second distal end line 32*b* of intersection is positioned on the straight line V in a front view seen in a direction along the axial direction A of the needle tube 3G.

As shown in FIGS. 37 and 41, the first needle tip portion 31G and the second needle tip portion 32G form the opening 4G that is surrounded by the first blade surface 33G, the second blade surface 34G, the third blade surface 35G, and the fourth blade surface 36G. The opening 4G communicates with the internal space of the tubular portion 30 having a tubular shape.

As shown in FIG. 41, the first blade surface 33G, the second blade surface 34G, the third blade surface 35G, and the fourth blade surface 36G are curved surfaces, and have the same curvature in a front view seen in a direction along the axial direction A of the needle tube 3G.

(First Blade Surface 33G)

The first blade surface 33G is formed of a curved surface. As shown in FIGS. 44 to 46, in a front view seen in a direction along the axial direction A of the needle tube 3G, the ridge line of the first blade surface 33G extends in an arc shape recessed toward the outer peripheral surface 31*e*.

As shown in FIG. 44, in a front view seen in a direction along the axial direction A of the needle tube 3G, a normal vector 33*n* of the first blade surface 33G in the distal end region z1 is directed to the third blade surface 35G in the distal end region Z1 at any position on the curved surface as compared to a direction orthogonal to the straight line V.

As shown in FIG. 45, a normal vector 33*n* of the first blade surface 33G in the intermediate region Z2 is also directed to the third blade surface 35G in the intermediate region Z2 as compared to the direction orthogonal to the straight line V as in the distal end region z1.

The first outer edge 33*b* is a line of intersection (first outer line 33*b* of intersection) at which the first blade surface 33G (first continuous blade surface 401) and the outer peripheral surface 31*e* intersect with each other, and includes an edge in the circumferential direction of the tubular portion 30. The first outer edge 33*b* is a part of the first continuous blade surface-outer edge 401*b*. As shown in FIGS. 44 to 46, an angle θ1 formed between the first blade surface 33G (first continuous blade surface 401) and the outer peripheral surface 31*e* at the first outer edge 33*b* (first continuous blade surface-outer edge 401*b*) is an acute angle from the distal end region Z1 to the first proximal end region Z31 (the first proximal end 38G of the edge of the opening 4G) in a front view seen in a direction along the axial direction A of the needle tube 3G.

A line of intersection (first inner line 33*c* of intersection) at which the first blade surface 33G and the inner peripheral surface 31*i* intersect with each other is a first inner edge 33*c* including an edge in the circumferential direction of the tubular portion 30. The first inner edge 33*c* is a part of the first continuous blade surface-inner edge 401*c*. As shown in FIGS. 44 to 46, an angle θ2 formed between the first blade surface 33G (first continuous blade surface 401) and the inner peripheral surface 31*i* at the first inner edge 33*c* (first continuous blade surface-inner edge 401*c*) is an obtuse angle from the distal end region Z1 to the first proximal end region Z31 (the first proximal end 38G of the edge of the opening 4G) in a front view seen in a direction along the axial direction A of the needle tube 3G.

(Second Blade Surface 34G)

The second blade surface 34G is formed of a curved surface. As shown in FIGS. 44 to 46, in a front view seen in a direction along the axial direction A of the needle tube 3G, the ridge line of the second blade surface 34G extends in an arc shape recessed toward the outer peripheral surface 31*e*.

As shown in FIG. 44, in a front view seen in a direction along the axial direction A of the needle tube 3G, a normal vector 34*n* of the second blade surface 34G in the distal end region Z1 is directed to the fourth blade surface 36G in the distal end region Z1 at any position on the curved surface as compared to a direction orthogonal to the straight line V.

As shown in FIG. 45, a normal vector 34*n* of the second blade surface 34G in the intermediate region 22 is also directed to the fourth blade surface 36G in the intermediate region Z2 as compared to the direction orthogonal to the straight line V as in the distal end region z1.

The second outer edge 34*b* is a line of intersection (second outer line 34*b* of intersection) at which the second blade surface 34G (second continuous blade surface 402) and the outer peripheral surface 31*e* intersect with each other, and includes an edge in the circumferential direction of the tubular portion 30. The second outer edge 34*b* is a part of the second continuous blade surface-outer edge 402*b*. As shown in FIGS. 44 to 46, an angle θ3 formed between the second blade surface 34G (second continuous blade surface 402) and the outer peripheral surface 31*e* at the second outer edge 34*b* (second continuous blade surface-outer edge 402*b*) is an acute angle from the distal end region Z1 to the first proximal end region Z31 (the second proximal end 39G of the edge of the opening 4G) in a front view seen in a direction along the axial direction of the needle tube 3G.

A line of intersection (second inner line 34*c* of intersection) at which the second blade surface 34G and the inner peripheral surface 31*i* intersect with each other is a second inner edge 34*c* including an edge in the circumferential direction of the tubular portion 30. The second inner edge 34*c* is a part of the second continuous blade surface-inner edge 402*c*. As shown in FIGS. 44 to 46, an angle θ4 formed between the second blade surface 34G (second continuous blade surface 402) and the inner peripheral surface 31*i* at the second inner edge 34c (second continuous blade surface-inner edge 402c) is an obtuse angle from the distal end region z1 to the first proximal end region Z31 (the second proximal end 39G of the edge of the opening 4G) in a front view seen in a direction along the axial direction A of the needle tube 3G.

(Third Blade Surface 35G)

The third blade surface 35G is formed of a curved surface. As shown in FIGS. 44 to 46, in a front view seen in a direction along the axial direction A of the needle tube 3G, the ridge line of the third blade surface 35G extends in an arc shape released toward the outer peripheral surface 32e.

As shown in FIG. 44, in a front view seen in a direction along the axial direction A of the needle tube 3G, a normal vector 35n of the third blade surface 35G in the distal end region 21 is directed to the first blade surface 33G in the distal end region Z1 at any position on the curved surface as compared to a direction orthogonal to the straight line V.

As shown in FIG. 45, a normal vector 35n of the third blade surface 35G in the intermediate region Z2 is also directed to the first blade surface 33G in the intermediate region Z2 as compared to the direction orthogonal to the straight line V as in the distal end region Z1.

The third outer edge 35b is a line of intersection (third outer line 35b of intersection) at which the third blade surface 35G (first continuous blade surface 401) and the outer peripheral surface 32e intersect with each other, and includes an edge in the circumferential direction of the tubular portion 30. The third outer edge 35b is a part of the first continuous blade surface-outer edge 401b. As shown in FIGS. 44 to 46, an angle θ5 formed between the third blade surface 35G (first continuous blade surface 401) and the outer peripheral surface 32e at the third outer edge 35b (first continuous blade surface-outer edge 401b) is an acute angle from the distal end region Z1 to the first proximal end region Z31 (the first proximal end 38G of the edge of the opening 4G) in a front view seen in a direction along the axial direction A of the needle tube 3G.

A line of intersection (third inner line 35c of intersection) at which the third blade surface 35G and the inner peripheral surface 32i intersect with each other is a third inner edge 35c including an edge in the circumferential direction of the tubular portion 30. The third inner edge 35c is a part of the first continuous blade surface-inner edge 401c. As shown in FIGS. 44 to 46, an angle θ6 formed between the third blade surface 35G (first continuous blade surface 401) and the inner peripheral surface 32i at the third inner edge 35c (first continuous blade surface-inner edge 401c) is an obtuse angle from the distal end region z1 to the first proximal end region Z31 (the first proximal end 38G of the edge of the opening 4G) in a front view seen in a direction along the axial direction A of the needle tube 3G.

(Fourth Blade Surface 36G)

The fourth blade surface 36G is formed of a curved surface. As shown in FIGS. 44 to 46, in a front view seen in a direction along the axial direction A of the needle tube 3G, the ridge line of the fourth blade surface 36G extends in an arc shape released toward the outer peripheral surface 32e.

As shown in FIG. 44, in a front view seen in a direction along the axial direction A of the needle tube 3G, a normal vector 36n of the fourth blade surface 36G in the distal end region Z1 is directed to the second blade surface 34G in the distal end region Z1 at any position on the curved surface as compared to a direction orthogonal to the straight line V.

As shown in FIG. 45, a normal vector 36n of the fourth blade surface 36G in the intermediate region Z2 is also directed to the second blade surface 34G in the intermediate region Z2 as compared to the direction orthogonal to the straight line V as in the distal end region Z1.

The fourth outer edge 36b is a line of intersection (fourth outer line 36b of intersection) at which the fourth blade surface 36G (second continuous blade surface 402) and the outer peripheral surface 32e intersect with each other, and includes an edge in the circumferential direction of the tubular portion 30. The fourth outer edge 36b is a part of the second continuous blade surface-outer edge 402b. As shown in FIGS. 44 to 46, an angle θ7 formed between the fourth blade surface 36G (second continuous blade surface 402) and the outer peripheral surface 32e at the fourth outer edge 36b (second continuous blade surface-outer edge 402b) is an acute angle from the distal end region Z1 to the first proximal end region Z31 (the second proximal end 39G of the edge of the opening 4G) in a front view seen in a direction along the axial direction of the needle tube 3G.

A line of intersection (fourth inner line 36c of intersection) at which the fourth blade surface 36G and the inner peripheral surface 32i intersect with each other is a fourth inner edge 36c including an edge in the circumferential direction of the tubular portion 30. The fourth inner edge 36c is a part of the second continuous blade surface-inner edge 402c. As shown in FIGS. 44 to 46, an angle θ8 formed between the fourth blade surface 36G (second continuous blade surface 402) and the inner peripheral surface 32i at the fourth inner edge 36c (second continuous blade surface-inner edge 402c) is an obtuse angle from the distal end region Z1 to the first proximal end region Z31 (the second proximal end 39G of the edge of the opening 4G) in a front view seen in a direction along the axial direction A of the needle tube 3G.

(Seventh Blade Surface 43G)

The seventh blade surface 43G is a blade surface that is formed closer to the proximal end side than the first proximal end 38G. The seventh blade surface 43G forms a part of the inner peripheral surface 31i of the first needle tip portion 31G and the inner peripheral surface 32i of the second needle tip portion 32G. The seventh blade surface 43G has the shape of a curved surface continuously connected to the first blade surface 33G and the third blade surface 35G, and is preferably continuous between the first blade surface 33G and the seventh blade surface 43G and between the third blade surface 35G and the seventh blade surface 43G without a level difference.

As shown in FIGS. 39 and 47, the curvature of a curve formed by the seventh blade surface 43G is larger than the curvature of the inner peripheral surface 30i of the tubular portion 30 in a cross section perpendicular to the axial direction A.

As shown in FIG. 42, a thickness T3 between the seventh blade surface 43G (first continuous blade surface 401) and the outer peripheral surface 31e of the first needle tip portion 31E is reduced toward the first proximal end 38G from the proximal end of the seventh blade surface 43G (the proximal end of the first continuous blade surface 401). Further, as shown in FIG. 43, a thickness T3 between the seventh blade surface 43G (first continuous blade surface 401) and the outer peripheral surface 32e of the second needle tip portion 32E is reduced toward the first proximal end 38G from the proximal end of the seventh blade surface 43G (the proximal end of the first continuous blade surface 401).

As shown in FIGS. 42 and 43, a first proximal end edge 38g of which the distal end is the first proximal end 38G is formed in the second proximal end region Z32. The first proximal end edge 38g is a sharp blade that is formed by the seventh blade surface 43G and the outer peripheral surfaces 31*e* and 32*e*. The thickness T3 at the first proximal end 38G is set to be small, so that a resistance force, which is applied to the first proximal end 38G from tissue in a case where the body tissue is punctured by the needle tube 3G, can be reduced. Further, distal end angles formed between the seventh blade surface 43G and the outer peripheral surfaces 31*e* and 32*e* are set to be small at the first proximal end 38G, so that the first proximal end edge 38*g* is formed.

(Eighth Blade Surface 44G)

The eighth blade surface 44G is a blade surface that is formed closer to the proximal end side than the second proximal end 39G. The eighth blade surface 44G forms a part of the inner peripheral surface 31*i* of the first needle tip portion 31G and the inner peripheral surface 32*i* of the second needle tip portion 32G. The eighth blade surface 44G has the shape of a curved surface continuously connected to the second blade surface 34G and the fourth blade surface 36G, and is preferably continuous between the second blade surface 34G and the eighth blade surface 44G and between the fourth blade surface 36G and the eighth blade surface 44G without a level difference.

As shown in FIGS. 39 and 47, the curvature of a curve formed by the eighth blade surface 44G is larger than the curvature of the inner peripheral surface 30*i* of the tubular portion 30 in a cross section perpendicular to the axial direction A.

As shown in FIG. 42, a thickness T3 between the eighth blade surface 44G (second continuous blade surface 402) and the outer peripheral surface 31*e* of the first needle tip portion 31E is reduced toward the second proximal end 39G from the proximal end of the eighth blade surface 44G (the proximal end of the second continuous blade surface 402). Further, as shown in FIG. 43, a thickness T3 between the eighth blade surface 44G (second continuous blade surface 402) and the outer peripheral surface 32*e* of the second needle tip portion 32E is reduced toward the second proximal end 39G from the proximal end of the eighth blade surface 44G (the proximal end of the second continuous blade surface 402).

As shown in FIGS. 42 and 43, a second proximal end edge 39*g* of which the distal end is the second proximal end 39G is formed in the second proximal end region Z32. The second proximal end edge 39*g* is a sharp blade that is formed by the eighth blade surface 44G and the outer peripheral surfaces 31*e* and 32*e*. The thickness T3 at the second proximal end 39G is set to be small, so that a resistance force, which is applied to the second proximal end 39G from tissue in a case where the body tissue is punctured by the needle tube 3G, can be reduced. Further, distal end angles formed between the eighth blade surface 44G and the outer peripheral surfaces 31*e* and 32*e* are set to be small at the second proximal end 39G, so that the second proximal end edge 39*g* is formed.

According to the biopsy system 150G including the puncture needle 1G according to this embodiment, not only the first outer edge 33*b*, the second outer edge 34*b*, the third outer edge 35*b*, and the fourth outer edge 36*b* but also the first proximal end edge 38*g* and the second proximal end edge 39*g* cut into body tissue. Accordingly, it is easy to collect the body tissue (a sample required for diagnosis).

According to the biopsy system 150G including the puncture needle 1G according to this embodiment, punctureability into body tissue is high (the puncture needle 1G easily cuts into the body tissue) and it is easy to collect the cut-out body tissue (a sample required for diagnosis) into the puncture needle 1G. Since the first proximal end 38G and the second proximal end 39G of the needle tube 3G are thinner and sharper than those of the needle tube 3 of the above embodiment (FIGS. 1-10), the needle tube 3G has higher punctureability and collectability. Further, since the first outer edge 33*b*, the second outer edge 34*b*, the third outer edge 35*b*, and the fourth outer edge 36*b* of the needle tube 3G are acute angles in the distal end region Z1, the intermediate region Z2, and the first proximal end region Z31, the needle tube 3G has higher punctureability.

Figure 48:
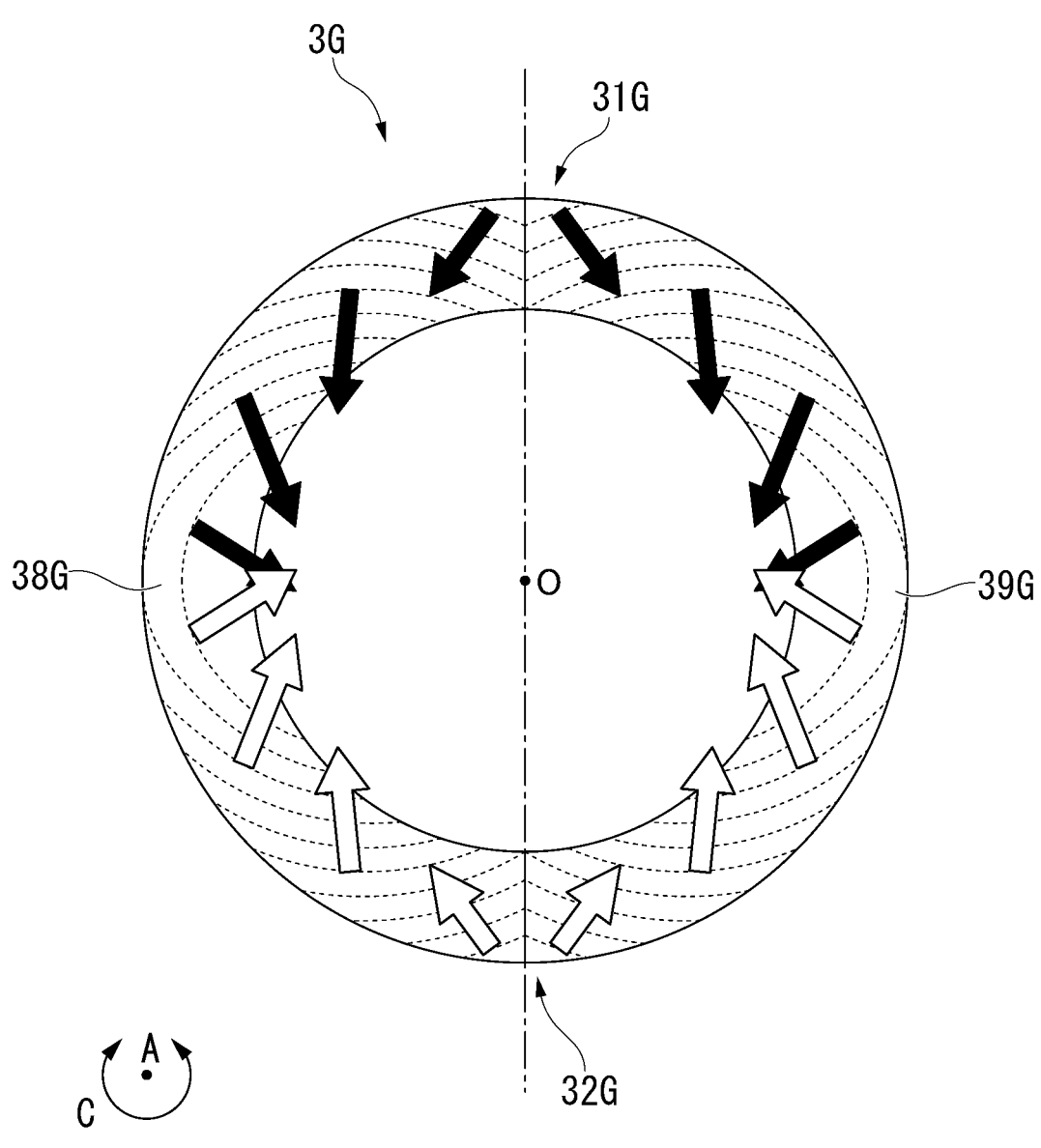
FIG. 48 is a diagram in which normals to blade surfaces, such as a first blade surface, are displayed by arrows in a cross section perpendicular to an axial direction in the diagram shown in FIG. 41.

FIG. 48 is a diagram in which normals to blade surfaces, such as the first blade surface 33G, are displayed by arrows in a cross section perpendicular to the axial direction A in the diagram shown in FIG. 41. In the needle tube 3G, the normals to the blade surfaces are directed to directions, which further approach the central axis O, from the distal end toward the proximal end as compared to the circumferential direction C of the tubular portion 30. As a result, the collectability of the needle tube 3G is higher than that of the needle tube 3 of the above embodiment (FIGS. 1-10).

This embodiment has been described in detail above with reference to the drawings, but specific configuration is not limited to this embodiment and also includes design changes and the like without departing from the scope of the present disclosure. Further, components shown in the above-mentioned embodiment and a modification example can be appropriately combined.

A biopsy system 150H including an endoscope puncture needle 1H according to another exemplary embodiment of the present disclosure will be described with reference to FIGS. 49 to 50. In the following description, components common to the already described components will be denoted by the same reference numerals and the repeated description thereof will be omitted. The endoscope puncture needle 1H is different from the endoscope puncture needle 1 according to the above embodiment (FIGS. 1-10) in terms of a number of the needle tip portions included in the needle tube.

[Biopsy System 150H]

The biopsy system 150H is the medical equipment that is used to collect tissue in a body during a biopsy. The biopsy system 150H includes the ultrasound endoscope 100 and an endoscope puncture needle 1H (hereinafter, simply referred to as a "puncture needle 1H"). The puncture needle 1H includes an insertion body 2H, the operation unit 8, and the stylet 27.

[Insertion Body 2H]

The insertion body 2H is an elongated member that can be inserted into the channel 107 of the ultrasound endoscope 100. The insertion body 2H includes a needle tube 3H and the sheath 7.

Figure 49:
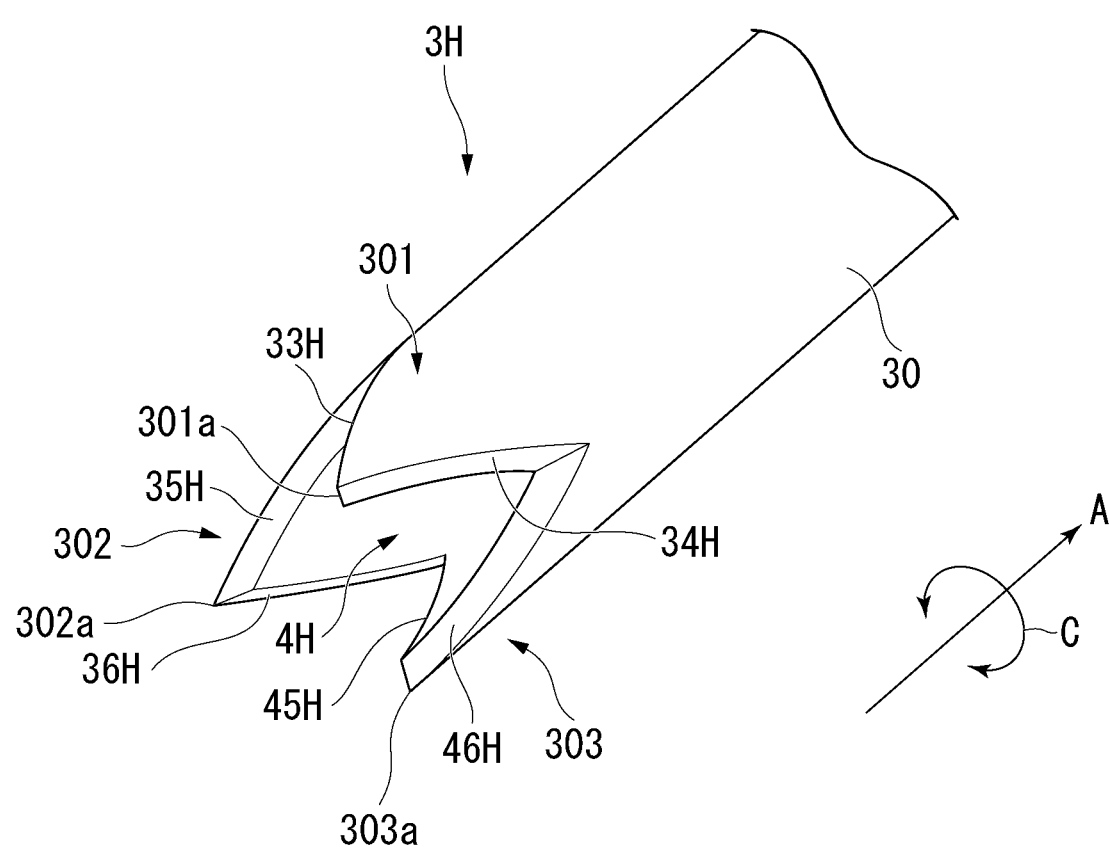
FIG. 49 is a perspective view of a needle tube included in an endoscope puncture needle according to an exemplary embodiment.

FIG. 49 is a perspective view of the needle tube 3H. FIG. 50 is a cross-sectional view of the needle tube 3H in the distal end region z1.

As shown in FIG. 49, the needle tube 3H includes the tubular portion 30 having a tubular shape, and a first needle tip portion 301, a second needle tip portion 302, and a third needle tip portion 303 provided at the distal end of the tubular portion 30. The needle tube 3H can be operated to advance and retreat in the sheath 7 by the operation unit 8. An opening 4H, which serves as an entrance through which tissue punctured by the first needle tip portion 301, the second needle tip portion 302, and the third needle tip portion 303 enters the inside of the needle tube 3H, is formed at the distal end of the needle tube 3H. The first needle tip portion 301, the second needle tip portion 302, and the third needle tip portion 303 of the needle tube 3H can protrude and retract from an opening formed at the distal end portion of the sheath 7.

The first needle tip portion 301 includes a first blade surface 33H and a second blade surface 34H, and the first blade surface 33H and the second blade surface 34H extend toward a sharp first needle tip 301*a*. An inner peripheral surface 31*i* of the first needle tip portion 301 is a curved surface continuous with the inner peripheral surface 30*i* of the tubular portion 30, and has the same diameter and curvature as the inner peripheral surface 30*i*.

The second needle tip portion 302 includes a third blade surface 35H and a fourth blade surface 36H, and the third blade surface 35H and the fourth blade surface 36H extend toward a sharp second needle tip 302*a*. An inner peripheral surface 32*i* of the second needle tip portion 302 is a curved surface continuous with the inner peripheral surface 30*i* of the tubular portion 30, and has the same diameter and curvature as the inner peripheral surface 30*i*.

The third needle tip portion 303 includes a ninth blade surface 45H and a tenth blade surface 46H, and the ninth blade surface 45H and the tenth blade surface 46H extend toward a sharp third needle tip 303*a*. An inner peripheral surface 33*i* of the third needle tip portion 303 is a curved surface continuous with the inner peripheral surface 30*i* of the tubular portion 30, and has the same diameter and curvature as the inner peripheral surface 30*i*.

Figure 50:
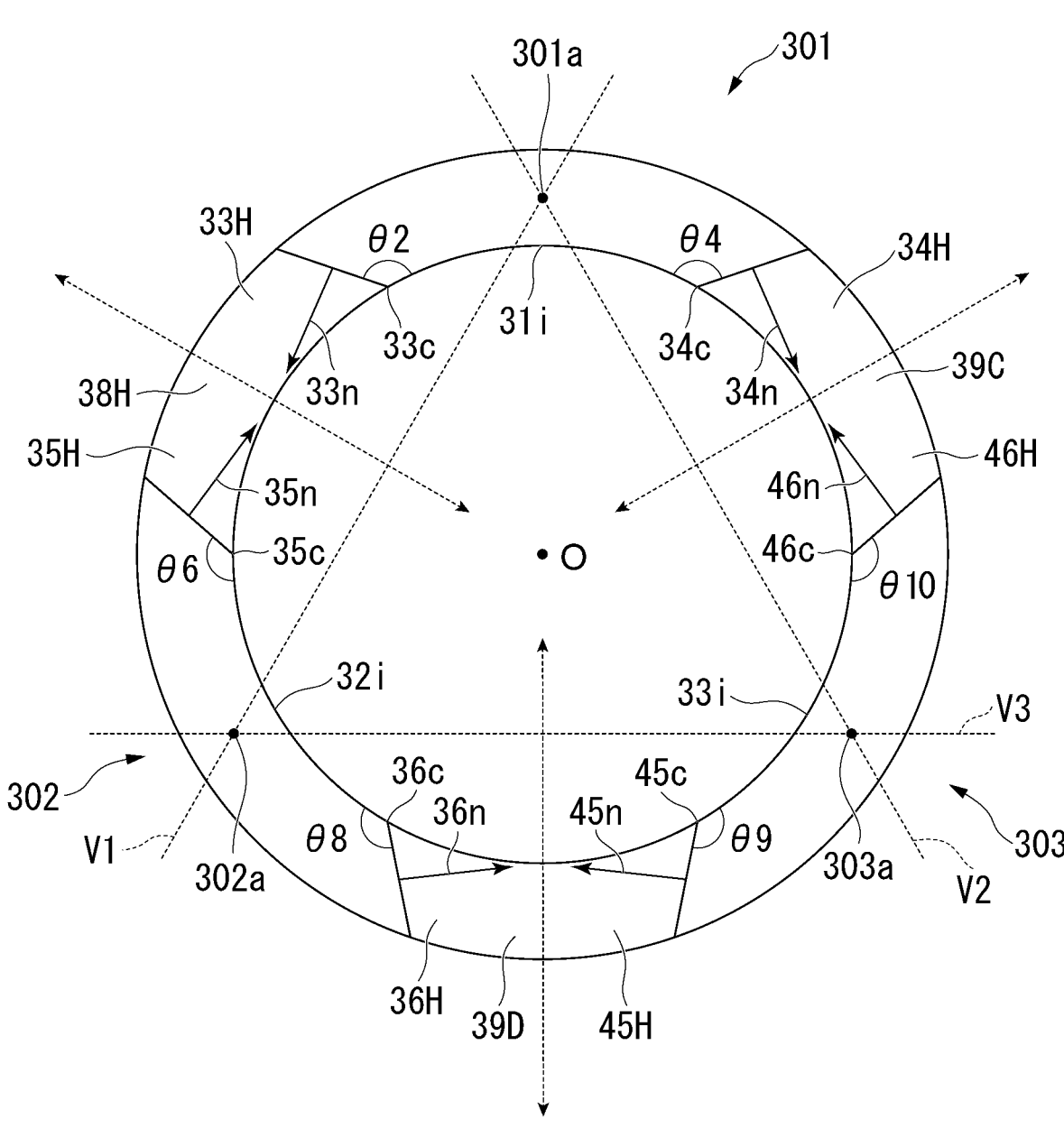
FIG. 50 is a cross-sectional view of the needle tube.

As shown in FIG. 49 and FIG. 50, the first needle tip portion 301, the second needle tip portion 302, and the third needle tip portion 303 form the opening 4H that is surrounded by the first blade surface 33H, the second blade surface 34H, the third blade surface 35H, the fourth blade surface 36H, the ninth blade surface 45H, and the tenth blade surface 46H. The opening 4H communicates with the internal space of the tubular portion 30 having a tubular shape.

The first blade surface 33H and the third blade surface 35H are connected to each other at a first proximal end 38H of the edge of the opening 4H. The second blade surface 34H and the tenth blade surface 46H are connected to each other at a third proximal end 39C of the edge of the opening 4H. The fourth blade surface 36H and the ninth blade surface 45H are connected to each other at a fourth proximal end 39D of the edge of the opening 4H.

(First Blade Surface 33H and Second Blade Surface 34H of First Needle Tip Portion 301)

As shown in FIG. 49 and FIG. 50, a line of intersection (first inner line 33*c* of intersection) between the first blade surface 33H and the inner peripheral surface 31*i* of the first needle tip portion 301 defines a part of the contour of the opening 4H. A line of intersection (second inner line 34*c* of intersection) between the second blade surface 34H and the inner peripheral surface 31*i* of the first needle tip portion 31 defines a part of the contour of the opening 4H.

As shown in FIG. 50, in a front view seen in a direction along the axial direction A of the needle tube 3H (tubular portion 30), the normal vector 33*n* of the first blade surface 33H in the distal end region Z1 is directed to the third blade surface 35H in the distal end region Z1 as compared to a direction orthogonal to the straight line V1 passing through the first needle tip 301*a* and the second needle tip 302*a*. Likewise, in the same front view, the normal vector 34*n* of the second blade surface 34H in the distal end region Z1 is directed to the tenth blade surface 46H in the distal end region Z1 as compared to the direction orthogonal to the straight line V2 passing through the first needle tip 301*a* and the third needle tip 303*a*.

Preferably, as shown in FIG. 50, the normal vector 33*n* of the first blade surface 33H and the normal vector 34*n* of the second blade surface 34H are directed to a direction, which approaches the central axis O, in the distal end region Z1 as compared to the circumferential direction C of the tubular portion 30.

A line of intersection (first inner line 33*c* of intersection) at which the first blade surface 33H and the inner peripheral surface 31*i* intersect with each other is a first inner edge 33*c* including an edge in the circumferential direction of the tubular portion 30. As shown in FIG. 50, an angle θ2 formed between the first blade surface 33H and the inner peripheral surface 31*i* at the first inner edge 33*c* is an obtuse angle in the distal end region Z1 in the front view seen in a direction along the axial direction A of the needle tube 3H.

A line of intersection (second inner line 34*c* of intersection) at which the second blade surface 34H and the inner peripheral surface 31*i* intersect with each other is a second inner edge 34*c* including an edge in the circumferential direction of the tubular portion 30. As shown in FIG. 50, an angle θ4 formed between the second blade surface 34H and the inner peripheral surface 31*i* at the second inner edge 34*c* is an obtuse angle in the distal end region Z1 in the front view seen in a direction along the axial direction A of the needle tube 3H.

(Third Blade Surface 35H and Fourth Blade Surface 36H of Second Needle Tip Portion 302)

As shown in FIG. 49 and FIG. 50, a line of intersection (third inner line 35*c* of intersection) between the third blade surface 35H and the inner peripheral surface 32*l* of the second needle tip portion 302 defines a part of the contour of the opening 4H. A line of intersection (fourth inner line 36*c* of intersection) between the fourth blade surface 36H and the inner peripheral surface 32*i* of the second needle tip portion 302 defines a part of the contour of the opening 4H.

As shown in FIG. 50, in a front view seen in a direction along the axial direction A of the needle tube 3H, the normal vector 35*n* of the third blade surface 35H in the distal end region Z1 is directed to the first blade surface 33H in the distal end region Z1 as compared to a direction orthogonal to the straight line V1 passing through the first needle tip 301*a* and the second needle tip 302*a*. Likewise, in the same front view, the normal vector 36*n* of the fourth blade surface 36H in the distal end region Z1 is directed to the ninth blade surface 45H in the distal end region Z1 as compared to the direction orthogonal to the straight line V3 passing through the second needle tip 302*a* and the third needle tip 303*a*.

Preferably, as shown in FIG. 50, the normal vector 35*n* of the third blade surface 35H and the normal vector 36*n* of the fourth blade surface 36H are directed to a direction, which approaches the central axis O, in the distal end region Z1 as compared to the circumferential direction C of the tubular portion 30.

A line of intersection (third inner line 35*c* of intersection) at which the third blade surface 35H and the inner peripheral surface 32*i* intersect with each other is a third inner edge 35*c* including an edge in the circumferential direction of the tubular portion 30. As shown in FIG. 50, an angle θ6 formed between the third blade surface 35H and the inner peripheral surface 31*i* at the third inner edge 35*c* is an obtuse angle in the distal end region 21 in the front view seen in a direction along the axial direction A of the needle tube 3H.

A line of intersection (fourth inner line 36*c* of intersection) at which the fourth blade surface 36H and the inner peripheral surface 32*i* intersect with each other is a fourth inner edge 36*c* including an edge in the circumferential direction of the tubular portion 30. As shown in FIG. 50, an angle θ8 formed between the fourth blade surface 36H and the inner peripheral surface 31*i* at the fourth inner edge 36*c* is an obtuse angle in the distal end region Z1 in the front view seen in a direction along the axial direction A of the needle tube 3H.

(Ninth Blade Surface 45H and Tenth Blade Surface 46H of Third Needle Tip Portion 303)

As shown in FIG. 49 and FIG. 50, a line of intersection (third inner line 35c of intersection) between the ninth blade surface 45H and the inner peripheral surface 33i of the third needle tip portion 303 defines a part of the contour of the opening 4H. A line of intersection (fourth inner line 36c of intersection) between the ninth blade surface 46H and the inner peripheral surface 33i of the third needle tip portion 303 defines a part of the contour of the opening 4H.

As shown in FIG. 50, in a front view seen in a direction along the axial direction A of the needle tube 3H, the normal vector 45n of the ninth blade surface 45H in the distal end region Z1 is directed to the fourth blade surface 36H in the distal end region Z1 as compared to a direction orthogonal to the straight line V3 passing through the second needle tip 302a and the third needle tip 303a. Likewise, in the same front view, the normal vector 46n of the tenth blade surface 46H in the distal end region Z1 is directed to the second blade surface 34H in the distal end region 21 as compared to the direction orthogonal to the straight line V2 passing through the first needle tip 301a and the third needle tip 303a.

Preferably, as shown in FIG. 50, the normal vector 45n of the ninth blade surface 45H and the normal vector 46n of the tenth blade surface 46H are directed to a direction, which approaches the central axis O, in the distal end region Z1 as compared to the circumferential direction C of the tubular portion 30.

A line of intersection (ninth inner line 45c of intersection) at which the ninth blade surface 45H and the inner peripheral surface 33i intersect with each other is a ninth inner edge 45c including an edge in the circumferential direction of the tubular portion 30. As shown in FIG. 50, an angle θ9 formed between the ninth blade surface 45H and the inner peripheral surface 33i at the ninth inner edge 45c is an obtuse angle in the distal end region Z1 in the front view seen in a direction along the axial direction A of the needle tube 3H.

A line of intersection (tenth inner line 46c of intersection) at which the tenth blade surface 46H and the inner peripheral surface 33i intersect with each other is a tenth inner edge 46c including an edge in the circumferential direction of the tubular portion 30. As shown in FIG. 50, an angle θ10 formed between the tenth blade surface 46H and the inner peripheral surface 33i at the tenth inner edge 46c is an obtuse angle in the distal end region Z1 in the front view seen in a direction along the axial direction A of the needle tube 3H.

According to the biopsy system 150H including the puncture needle 1G according to the present embodiment, punctureability into body tissue is high (the puncture needle 1G easily cuts into the body tissue) and it is easy to collect the cut-out body tissue (a sample required for diagnosis) into the puncture needle 1H.

The present embodiment has been described in detail above with reference to the drawings, but specific configuration is not limited to this embodiment and also includes design changes and the like without departing from the scope of the present disclosure. Further, components shown in the above-mentioned embodiment and a modification example can be appropriately combined.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation portion. The present disclosure is not limited by the above description, but only by the appended claims.

What is claimed is:

1. An endoscope puncture needle comprising:
a tubular portion having a tubular shape and extending along an axial direction from a proximal end to a distal end at which an opening to an internal space in the tubular portion is formed;
a first needle tip portion that is provided at a distal end portion of the tubular portion and includes:
a first needle tip at a distal end thereof, and
a first blade surface and a second blade surface extending toward the first needle tip; and
a second needle tip portion that is provided at the distal end portion of the tubular portion and includes:
a second needle tip at a distal end thereof, and
a third blade surface and a fourth blade surface extending toward the second needle tip,
wherein:
the first blade surface, the second blade surface, the third blade surface, and the fourth blade surface form an edge of the opening to the internal space in the tubular portion,
in the first needle tip portion and the second needle tip portion, as seen from a front view along the axial direction of the tubular portion, the first blade surface faces in a first facing direction that extends orthogonally from the first blade surface so as to approach the third blade surface, and the third blade surface faces in a third facing direction that extends orthogonally from the third blade surface so as to approach the first blade surface,
the first facing direction and the third facing direction are nonparallel to a straight line passing through the first needle tip and the second needle tip,
as seen from the front view along the axial direction, the second blade surface faces in a second facing direction that extends orthogonally from the second blade surface so as to approach the fourth blade surface, and the fourth blade surface faces in a fourth facing direction that extends orthogonally from the fourth blade surface so as to approach the second blade surface, and
the second facing direction and the fourth facing direction are nonparallel to the straight line passing through the first needle tip and the second needle tip.

2. The endoscope puncture needle according to claim 1, wherein the first needle tip portion and the second needle tip portion further include a distal end region, a proximal end region, and an intermediate region that is positioned between the distal end region and the proximal end region.

3. The endoscope puncture needle according to claim 2, wherein in the front view, the first facing direction of the first blade surface and the third facing direction of the third blade surface in the intermediate region form an acute angle with respect to the straight line passing through the first needle tip and the second needle tip, and the second facing direction of the second blade surface and the fourth facing direction of the fourth blade surface in the intermediate region form an acute angle with respect to the straight line passing through the first needle tip and the second needle tip.

4. The endoscope puncture needle according to claim 2, wherein the first needle tip portion includes:

a first outer edge formed by the first blade surface and an outer peripheral surface of the first needle tip portion, an angle between the first blade surface and the outer peripheral surface of the first needle tip portion being an acute angle in the distal end region and being an obtuse angle in the intermediate region, and a second outer edge formed by the second blade surface and the outer peripheral surface of the first needle tip portion, an angle between the second blade surface and the outer peripheral surface of the first needle tip portion being an acute angle in the distal end region and being an obtuse angle in the intermediate region, and the second needle tip portion includes:

a third outer edge formed by the third blade surface and an outer peripheral surface of the second needle tip portion, an angle between the third blade surface and the outer peripheral surface of the second needle tip portion being an acute angle in the distal end region and being an obtuse angle in the intermediate region, and a fourth outer edge formed by the fourth blade surface and the outer peripheral surface of the second needle tip portion, an angle between the fourth blade surface and the outer peripheral surface of the second needle tip portion being an acute angle in the distal end region and being an obtuse angle in the intermediate region.

5. The endoscope puncture needle according to claim 2, wherein the proximal end region includes a first proximal end at which the first blade surface and the third blade surface are connected to each other, and a second proximal end at which the second blade surface and the fourth blade surface are connected to each other, from the first needle tip up to the first proximal end, the first facing direction of the first blade surface and the third facing direction of the third blade surface are directed more towards a central axis of the tubular portion than a circumferential direction of the tubular portion, and from the second needle tip up to the second proximal end, the second facing direction of the second blade surface and the fourth facing direction of the fourth blade surface are directed more towards the central axis of the tubular portion than the circumferential direction of the tubular portion.

6. The endoscope puncture needle according to claim 2, wherein the first needle tip portion includes:

a first outer edge formed by the first blade surface and an outer peripheral surface of the first needle tip portion, an angle between the first blade surface and the outer peripheral surface of the first needle tip portion being an acute angle in the intermediate region, and a second outer edge formed by the second blade surface and the outer peripheral surface of the first needle tip portion, an angle between the second blade surface and the outer peripheral surface of the first needle tip portion being an acute angle in the intermediate region, and the second needle tip portion includes:

a third outer edge formed by the third blade surface and an outer peripheral surface of the second needle tip portion, an angle between the third blade surface and the outer peripheral surface of the second needle tip portion being an acute angle in the intermediate region, and a fourth outer edge formed by the fourth blade surface and the outer peripheral surface of the second needle tip portion, an angle between the fourth blade surface and the outer peripheral surface of the second needle tip portion being an acute angle in the intermediate region.

7. The endoscope puncture needle according to claim 2, wherein the first needle tip portion includes:

a first inner edge formed by the first blade surface and an inner peripheral surface of the first needle tip portion, an angle between the first blade surface and the inner peripheral surface of the first needle tip portion being an obtuse angle in the intermediate region, and a second inner edge formed by the second blade surface and the inner peripheral surface of the first needle tip portion, an angle between the second blade surface and the inner peripheral surface of the first needle tip portion being an obtuse angle in the intermediate region, and the second needle tip portion includes:

a third inner edge formed by the third blade surface and an inner peripheral surface of the second needle tip portion, an angle between the third blade surface and the inner peripheral surface of the second needle tip portion being an obtuse angle in the intermediate region, and a fourth inner edge formed by the fourth blade surface and the inner peripheral surface of the second needle tip portion, an angle between the fourth blade surface and the inner peripheral surface of the second needle tip portion being an obtuse angle in the intermediate region.

8. The endoscope puncture needle according to claim 2, wherein the proximal end region includes a first proximal end at which the first blade surface and the third blade surface are connected to each other, and a second proximal end at which the second blade surface and the fourth blade surface are connected to each other, the first needle tip portion and the second needle tip portion further include a fifth blade surface and a sixth blade surface, the fifth blade surface includes:

a first outer intersection between the fifth blade surface and a first outer edge that is formed by the first blade surface and an outer peripheral surface of the first needle tip portion, and a third outer intersection between the fifth blade surface and a third outer edge that is formed by the third blade surface and an outer peripheral surface of the second needle tip portion, and the sixth blade surface includes:

a second outer intersection between the sixth blade surface and a second outer edge that is formed by the second blade surface and the outer peripheral surface of the first needle tip portion, and a fourth outer intersection between the sixth blade surface and a fourth outer edge that is formed by the fourth blade surface and the outer peripheral surface of the second needle tip portion.

9. The endoscope puncture needle according to claim 8, wherein
the fifth blade surface and the sixth blade surface are inclined surfaces that are inclined with respect to a central axis of the tubular portion, and
distances between: (i) each of the fifth blade surface and the sixth blade surface and (ii) the central axis are reduced toward the first needle tip and the second needle tip from the proximal end of the tubular portion.

10. The endoscope puncture needle according to claim 8, wherein
a thickness between the fifth blade surface and an inner peripheral surface of the first needle tip portion is reduced toward the first proximal end from a proximal end of the fifth blade surface,
a thickness between the fifth blade surface and an inner peripheral surface of the second needle tip portion is reduced toward the first proximal end from the proximal end of the fifth blade surface,
a thickness between the sixth blade surface and the inner peripheral surface of the first needle tip portion is reduced toward the second proximal end from a proximal end of the sixth blade surface, and
a thickness between the sixth blade surface and the inner peripheral surface of the second needle tip portion is reduced toward the second proximal end from the proximal end of the sixth blade surface.

11. The endoscope puncture needle according to claim 2, wherein
the proximal end region includes a first proximal end at which the first blade surface and the third blade surface are connected to each other, and a second proximal end at which the second blade surface and the fourth blade surface are connected to each other,
the first needle tip portion and the second needle tip portion further include a seventh blade surface and an eighth blade surface,
the seventh blade surface includes:
a first inner intersection between the seventh blade surface and a first inner edge that is formed by the first blade surface and an inner peripheral surface of the first needle tip portion, and
a third inner intersection between the seventh blade surface and a third inner edge that is formed by the third blade surface and an inner peripheral surface of the second needle tip portion, and
the eighth blade surface includes:
a second inner intersection between the eighth blade surface and a second inner edge that is formed by the second blade surface and the inner peripheral surface of the first needle tip portion, and
a fourth inner intersection between the eighth blade surface and a fourth inner edge that is formed by the fourth blade surface and the inner peripheral surface of the second needle tip portion.

12. The endoscope puncture needle according to claim 11, wherein
the seventh blade surface is a curved surface that is formed on the inner peripheral surface of the first needle tip portion and the inner peripheral surface of the second needle tip portion, and the eighth blade surface is a curved surface that is formed on the inner peripheral surface of the first needle tip portion and the inner peripheral surface of the second needle tip portion.

13. The endoscope puncture needle according to claim 11, wherein
a thickness between the seventh blade surface and an outer peripheral surface of the first needle tip portion is reduced toward the first proximal end from a proximal end of the seventh blade surface,
a thickness between the seventh blade surface and an outer peripheral surface of the second needle tip portion is reduced toward the first proximal end from the proximal end of the seventh blade surface,
a thickness between the eighth blade surface and the outer peripheral surface of the first needle tip portion is reduced toward the second proximal end from a proximal end of the eighth blade surface, and
a thickness between the eighth blade surface and the outer peripheral surface of the second needle tip portion is reduced toward the second proximal end from the proximal end of the eighth blade surface.

14. The endoscope puncture needle according to claim 1, wherein
the first needle tip portion includes:
a first inner edge formed by the first blade surface and an inner peripheral surface of the first needle tip portion, an angle between the first blade surface and the inner peripheral surface of the first needle tip portion being an obtuse angle in a distal end region, and
a second inner edge formed by the second blade surface and the inner peripheral surface of the first needle tip portion, an angle between the second blade surface and the inner peripheral surface of the first needle tip portion being an obtuse angle in the distal end region, and
the second needle tip portion includes:
a third inner edge formed by the third blade surface and an inner peripheral surface of the second needle tip portion, an angle between the third blade surface and the inner peripheral surface of the second needle tip portion being an obtuse angle in the distal end region, and
a fourth inner edge formed by the fourth blade surface and the inner peripheral surface of the second needle tip portion, an angle between the fourth blade surface and the inner peripheral surface of the second needle tip portion being an obtuse angle in the distal end region.

15. The endoscope puncture needle according to claim 1, wherein the first needle tip and the second needle tip are arranged symmetrically with respect to a central axis of the tubular portion in the front view.

16. The endoscope puncture needle according to claim 1, wherein the first blade surface and the second blade surface have symmetric shapes with respect to the straight line passing through the first needle tip and the second needle tip in the front view.

17. The endoscope puncture needle according to claim 1, wherein the third blade surface and the fourth blade surface have symmetric shapes with respect to the straight line passing through the first needle tip and the second needle tip in the front view.

18. The endoscope puncture needle according to claim 1, further comprising:

a first continuous blade surface that includes the first blade surface and the third blade surface and forms a shape of a continuously curved surface;

a second continuous blade surface that includes the second blade surface and the fourth blade surface and forms a shape of a continuously curved surface;

a first continuous blade surface-outer edge that is a line of intersection between: (i) the first continuous blade surface and (ii) each of an outer peripheral surface of the first needle tip portion and an outer peripheral surface of the second needle tip portion; and a second continuous blade surface-outer edge that is a line of intersection between: (i) the second continuous blade surface and (ii) each of the outer peripheral surface of the first needle tip portion and the outer peripheral surface of the second needle tip portion, wherein an angle formed between the first continuous blade surface and the outer peripheral surface of the first needle tip portion at the first continuous blade surface-outer edge is an acute angle from a distal end region to a first proximal end of the edge of the opening, an angle formed between the first continuous blade surface and the outer peripheral surface of the second needle tip portion at the first continuous blade surface-outer edge is an acute angle from the distal end region to the first proximal end of the edge of the opening, an angle formed between the second continuous blade surface and the outer peripheral surface of the first needle tip portion at the second continuous blade surface-outer edge is an acute angle from the distal end region to a second proximal end of the edge of the opening, and an angle formed between the second continuous blade surface and the outer peripheral surface of the second needle tip portion at the second continuous blade surface-outer edge is an acute angle from the distal end region to the second proximal end of the edge of the opening.

19. The endoscope puncture needle according to claim 18, wherein a thickness between the first continuous blade surface and the outer peripheral surface of the first needle tip portion is reduced toward the first proximal end from a proximal end of the first continuous blade surface, a thickness between the first continuous blade surface and the outer peripheral surface of the second needle tip portion is reduced toward the first proximal end from the proximal end of the first continuous blade surface, a thickness between the second continuous blade surface and the outer peripheral surface of the first needle tip portion is reduced toward the second proximal end from a proximal end of the second continuous blade surface, and a thickness between the second continuous blade surface and the outer peripheral surface of the second needle tip portion is reduced toward the second proximal end from the proximal end of the second continuous blade surface.

20. The endoscope puncture needle according to claim 18, wherein the first continuous blade surface and the second continuous blade surface have symmetrical shapes with respect to the straight line passing through the first needle tip and the second needle tip in the front view.

21. The endoscope puncture needle according to claim 18, wherein the first blade surface, the second blade surface, the third blade surface, and the fourth blade surface are curved surfaces having a same curvature from the front view.

* * * * *